(12) United States Patent
Moskowitz et al.

(10) Patent No.: US 12,378,523 B2
(45) Date of Patent: Aug. 5, 2025

(54) PLATELETS AS DELIVERY AGENTS

(71) Applicant: Cellphire, Inc., Rockville, MD (US)

(72) Inventors: Keith Andrew Moskowitz, Westfield, IN (US); Amber Nicole Lee, Montgomery Village, MD (US); Rafael Jorda, Merignac (FR)

(73) Assignee: Cellphire, Inc., Rockville, MD (US)

( * ) Notice: Subject to any disclaimer, the term of this patent is extended or adjusted under 35 U.S.C. 154(b) by 0 days.

(21) Appl. No.: 18/361,772

(22) Filed: Jul. 28, 2023

(65) Prior Publication Data

US 2023/0383258 A1 Nov. 30, 2023

Related U.S. Application Data

(63) Continuation of application No. 16/697,401, filed on Nov. 27, 2019, now Pat. No. 11,767,511.

(60) Provisional application No. 62/828,043, filed on Apr. 2, 2019, provisional application No. 62/775,141, filed on Dec. 4, 2018, provisional application No. 62/773,931, filed on Nov. 30, 2018.

(51) Int. Cl.
| | |
|---|---|
| C07H 21/02 | (2006.01) |
| C12N 5/078 | (2010.01) |
| C12N 15/113 | (2010.01) |
| C12N 15/85 | (2006.01) |

(52) U.S. Cl.
CPC .......... C12N 5/0644 (2013.01); C12N 15/113 (2013.01); C12N 15/85 (2013.01); *C12N 2310/14* (2013.01); *C12N 2310/141* (2013.01); *C12N 2510/00* (2013.01)

(58) Field of Classification Search
CPC .......................... C12N 15/113; C12N 2310/14
See application file for complete search history.

(56) References Cited

U.S. PATENT DOCUMENTS

| | | |
|---|---|---|
| 3,928,566 A | 12/1975 | Briggs et al. |
| 3,932,943 A | 1/1976 | Briggs et al. |
| 4,059,967 A | 11/1977 | Rowe et al. |
| 4,157,383 A | 6/1979 | Johanssen et al. |
| 4,455,299 A | 6/1984 | Grode |
| 4,481,189 A | 11/1984 | Prince |
| 4,670,013 A | 6/1987 | Barnes et al. |
| 4,865,871 A | 9/1989 | Livesey et al. |
| 4,994,367 A | 2/1991 | Bode et al. |
| 5,059,518 A | 10/1991 | Kortright et al. |
| 5,213,814 A | 5/1993 | Goodrich, Jr. et al. |
| 5,332,578 A | 7/1994 | Chao |
| 5,364,756 A | 11/1994 | Livesey et al. |
| 5,423,738 A | 6/1995 | Robinson et al. |
| 5,571,801 A | 11/1996 | Segall et al. |
| 5,622,867 A | 4/1997 | Livesey et al. |
| 5,656,498 A | 8/1997 | Iijima et al. |
| 5,656,598 A | 8/1997 | Dunstan et al. |
| 5,723,281 A | 3/1998 | Segall et al. |
| 5,736,313 A | 4/1998 | Spargo et al. |
| 5,759,542 A | 6/1998 | Gurewich |
| 5,800,978 A | 9/1998 | Goodrich, Jr. et al. |
| 5,817,381 A | 10/1998 | Chen et al. |
| 5,827,741 A | 10/1998 | Beattie et al. |
| 5,919,614 A | 7/1999 | Livesey et al. |
| 5,958,670 A | 9/1999 | Goodrich, Jr. et al. |
| 5,993,804 A | 11/1999 | Read et al. |
| 6,127,111 A | 10/2000 | Braun |
| 6,211,575 B1 | 4/2001 | Hansford |
| 6,221,575 B1 | 4/2001 | Roser et al. |
| 6,372,423 B1 | 4/2002 | Braun |
| 6,596,296 B1 | 7/2003 | Nelson et al. |
| 6,653,062 B1 | 11/2003 | DePablo et al. |
| 6,723,497 B2 | 4/2004 | Wolkers et al. |
| 6,770,478 B2 | 8/2004 | Crowe et al. |
| 6,833,236 B1 | 12/2004 | Stienstra |
| 6,858,222 B2 | 2/2005 | Nelson et al. |
| 7,033,603 B2 | 4/2006 | Nelson et al. |
| 7,169,606 B2 | 1/2007 | DePablo et al. |
| 7,514,095 B2 | 4/2009 | Nelson et al. |
| 7,811,558 B2 | 10/2010 | Ho et al. |
| 8,097,403 B2 | 1/2012 | Ho et al. |
| 8,486,617 B2 | 7/2013 | Ho et al. |
| 8,486,619 B2 | 7/2013 | Miller et al. |
| 8,529,961 B2 | 9/2013 | Campbell et al. |
| 8,877,060 B2 | 11/2014 | Sehgal |
| 8,900,209 B2 | 12/2014 | Rosati |

(Continued)

FOREIGN PATENT DOCUMENTS

| | | |
|---|---|---|
| CA | 1261259 A | 9/1989 |
| CA | 2097063 C | 6/1992 |

(Continued)

OTHER PUBLICATIONS

Bannai et al. (Transfusion, 25, 1, 1985, 57-59).*
Fitzpatrick et al. (Transfusion, 2013, 53, 100S-106S).*
Tang, et. al., "Targeted repair of heart injury by stem cells fused with platelet nanovesicles", Nature Biomedical Engineering, vol. 2, No. 1, May 30, 2018, pp. 17-26, DOI:10.1038/s41551-017-0182-x.
Tans et al., "Comparison of anticoagulant and procoagulant activities of stimulated platelets and platelet-derived microparticles", Blood, Jun. 15, 1991, vol. 77, Issue 12, pp. 2641-2648, doi.org/10.1182/blood.V77.12.2641.2641.

(Continued)

*Primary Examiner* — Amy Rose Hudson

(74) *Attorney, Agent, or Firm* — Double Helix Law; Emanuel Vacchiano

(57) ABSTRACT

Provided herein are RNA agent-loaded platelets, methods of preparing RNA agent-loaded platelets, and methods of using RNA agent-loaded platelets. In some embodiments, methods of loading RNA agents into platelets include treating platelets with a RNA agent, a cationic transfection reagent, and a loading buffer that can include a salt, a base, a loading agent, and optionally at least one organic solvent.

20 Claims, 18 Drawing Sheets

(56) References Cited

U.S. PATENT DOCUMENTS

| | | |
|---|---|---|
| 9,402,866 B2 | 8/2016 | Radwanski et al. |
| 9,545,379 B2 | 1/2017 | Liu et al. |
| 9,863,699 B2 | 1/2018 | Corbin et al. |
| 9,878,011 B2 | 1/2018 | Landrigan et al. |
| 9,950,035 B2 | 4/2018 | Binder et al. |
| 10,400,017 B2 | 9/2019 | Higgins et al. |
| 10,441,634 B2 | 10/2019 | Landrigan et al. |
| 10,539,367 B2 | 1/2020 | Corbin et al. |
| 10,793,327 B2 | 10/2020 | Weimer et al. |
| 10,843,100 B2 | 11/2020 | Khan et al. |
| 10,969,171 B2 | 4/2021 | Corbin et al. |
| 10,976,105 B2 | 4/2021 | Corbin et al. |
| 11,052,045 B2 | 7/2021 | Liu et al. |
| 11,529,587 B2 | 12/2022 | Montgomery et al. |
| 11,701,388 B2 | 7/2023 | Moskowitz et al. |
| 11,752,468 B2 | 9/2023 | Montgomery et al. |
| 11,767,511 B2 | 9/2023 | Moskowitz et al. |
| 11,813,572 B2 | 11/2023 | Montgomery et al. |
| 12,208,122 B2 | 1/2025 | Moskowitz et al. |
| 2001/0019819 A1 | 9/2001 | Wolkers et al. |
| 2001/0028880 A1 | 10/2001 | Fisher et al. |
| 2001/0046487 A1 | 11/2001 | Roser et al. |
| 2002/0009500 A1 | 1/2002 | Wolkers et al. |
| 2002/0076445 A1 | 6/2002 | Crowe et al. |
| 2003/0022333 A1 | 1/2003 | Bronshtein |
| 2003/0073238 A1 | 4/2003 | Dzekunov et al. |
| 2003/0148449 A1 | 8/2003 | Kuliopulos et al. |
| 2003/0157475 A1 | 8/2003 | Schenk |
| 2004/0136974 A1 | 7/2004 | Crowe et al. |
| 2004/0147024 A1 | 7/2004 | Crowe et al. |
| 2004/0152964 A1 | 8/2004 | Crowe et al. |
| 2004/0185524 A1 | 9/2004 | Crowe et al. |
| 2004/0265293 A1* | 12/2004 | Crowe .................. A61K 35/19 435/2 |
| 2005/0028559 A1 | 2/2005 | Hiromatsu et al. |
| 2005/0048460 A1 | 3/2005 | Crowe et al. |
| 2005/0074402 A1 | 4/2005 | Cagnolini et al. |
| 2005/0181978 A1 | 8/2005 | Rojkjaer et al. |
| 2005/0191286 A1 | 9/2005 | Gandy |
| 2005/0222029 A1 | 10/2005 | Bartel et al. |
| 2006/0034809 A1 | 2/2006 | Ho et al. |
| 2006/0035383 A1 | 2/2006 | Ho et al. |
| 2006/0051731 A1 | 3/2006 | Ho et al. |
| 2006/0223050 A1 | 10/2006 | Crowe et al. |
| 2007/0087061 A1 | 4/2007 | Drake et al. |
| 2007/0166389 A1 | 7/2007 | Bakaltcheva |
| 2007/0178104 A1 | 8/2007 | Awdalla |
| 2007/0243137 A1 | 10/2007 | Hainfeld |
| 2007/0243178 A1 | 10/2007 | Ho et al. |
| 2007/0248612 A1 | 10/2007 | Wilson |
| 2007/0249047 A1 | 10/2007 | McKenna et al. |
| 2008/0064628 A1 | 3/2008 | Goodall et al. |
| 2008/0145834 A1 | 6/2008 | Ho et al. |
| 2008/0286366 A1 | 11/2008 | Fischer et al. |
| 2008/0299212 A1 | 12/2008 | Kim et al. |
| 2009/0035289 A1 | 2/2009 | Wagner et al. |
| 2009/0111118 A1 | 4/2009 | Mylvaganam et al. |
| 2009/0175905 A1 | 7/2009 | Tseng et al. |
| 2009/0299212 A1 | 12/2009 | Principe et al. |
| 2010/0055067 A1 | 3/2010 | Park |
| 2010/0135969 A1 | 6/2010 | Mishra |
| 2010/0159023 A1 | 6/2010 | Bjornstrup et al. |
| 2010/0190717 A1 | 7/2010 | Bevec et al. |
| 2010/0196461 A1 | 8/2010 | Simpkins |
| 2010/0267928 A1 | 10/2010 | Heckl |
| 2010/0273141 A1 | 10/2010 | Bakaltcheva et al. |
| 2011/0008804 A1 | 1/2011 | Kain et al. |
| 2011/0027257 A1 | 2/2011 | Burnouf et al. |
| 2011/0183311 A1 | 7/2011 | Ho et al. |
| 2011/0189151 A1 | 8/2011 | Stossel et al. |
| 2012/0009221 A1 | 1/2012 | Hoerr et al. |
| 2012/0028236 A1 | 2/2012 | Sehgal |
| 2012/0095085 A1 | 4/2012 | Layzer et al. |
| 2012/0100522 A1 | 4/2012 | Saghbini et al. |
| 2012/0125847 A1 | 5/2012 | Sehgal |
| 2012/0141434 A1 | 6/2012 | Peled et al. |
| 2012/0156306 A1 | 6/2012 | Weissman et al. |
| 2012/0264815 A1 | 10/2012 | Sullenger et al. |
| 2012/0276581 A1 | 11/2012 | Arav et al. |
| 2012/0321722 A1 | 12/2012 | Liu et al. |
| 2013/0059380 A1 | 3/2013 | Ho et al. |
| 2013/0061849 A1 | 3/2013 | Lemper |
| 2013/0122107 A1 | 5/2013 | Bakaltcheva |
| 2013/0195959 A1 | 8/2013 | Patel |
| 2013/0210903 A1 | 8/2013 | Sullenger et al. |
| 2014/0037750 A1 | 2/2014 | Radwanski et al. |
| 2014/0065120 A1 | 3/2014 | Nichols et al. |
| 2014/0329323 A1 | 11/2014 | Nygaard et al. |
| 2014/0330226 A1 | 11/2014 | Coffey |
| 2014/0356948 A1 | 12/2014 | Jeon et al. |
| 2015/0064259 A1 | 3/2015 | Simpkins |
| 2015/0306212 A1 | 10/2015 | Kahvejian et al. |
| 2015/0313943 A1 | 11/2015 | Kishikawa et al. |
| 2015/0313944 A1 | 11/2015 | Feng et al. |
| 2015/0361453 A1 | 12/2015 | Gresele et al. |
| 2016/0082044 A1 | 3/2016 | Liu et al. |
| 2016/0206783 A1 | 7/2016 | Dietz et al. |
| 2016/0219870 A1 | 8/2016 | Wang et al. |
| 2016/0231338 A1 | 8/2016 | Aster et al. |
| 2016/0235781 A1 | 8/2016 | Emanuele |
| 2016/0324897 A1 | 11/2016 | Ingber et al. |
| 2017/0198335 A1 | 7/2017 | Muller et al. |
| 2017/0274012 A1 | 9/2017 | Bode et al. |
| 2017/0333593 A1 | 11/2017 | Willard et al. |
| 2018/0009874 A1 | 1/2018 | Wilcox et al. |
| 2018/0070581 A1 | 3/2018 | Tarrand et al. |
| 2018/0092348 A1 | 4/2018 | She et al. |
| 2018/0169027 A1 | 6/2018 | Zhang et al. |
| 2018/0169139 A1 | 6/2018 | Feuerstein et al. |
| 2018/0235894 A1 | 8/2018 | Gu et al. |
| 2018/0311176 A1 | 11/2018 | Ozsolak et al. |
| 2018/0312903 A1 | 11/2018 | Grölz et al. |
| 2019/0008143 A1 | 1/2019 | Dee et al. |
| 2019/0076478 A1 | 3/2019 | Hale et al. |
| 2019/0192564 A1 | 6/2019 | Hijazi et al. |
| 2020/0046771 A1 | 2/2020 | Kuhn et al. |
| 2020/0060262 A1 | 2/2020 | Stolla |
| 2020/0076455 A1 | 3/2020 | Sharf |
| 2020/0078407 A1 | 3/2020 | Bhattacharya et al. |
| 2020/0093853 A1 | 3/2020 | Feuerstein et al. |
| 2020/0206143 A1 | 7/2020 | Moskowitz et al. |
| 2020/0208109 A1 | 7/2020 | Moskowitz et al. |
| 2020/0208110 A1 | 7/2020 | Lee et al. |
| 2020/0224164 A1 | 7/2020 | Moskowitz et al. |
| 2020/0281980 A1 | 9/2020 | Willard et al. |
| 2020/0291356 A1 | 9/2020 | Jorda et al. |
| 2020/0346167 A1 | 11/2020 | Montgomery et al. |
| 2021/0046120 A1 | 2/2021 | Moskowitz et al. |
| 2021/0046121 A1 | 2/2021 | Moskowitz et al. |
| 2021/0069240 A1 | 3/2021 | Jorda et al. |
| 2021/0100846 A1 | 4/2021 | Lee et al. |
| 2021/0180016 A1 | 6/2021 | Moskowitz et al. |
| 2021/0189341 A1 | 6/2021 | Sheik et al. |
| 2021/0299179 A1 | 9/2021 | Moskowitz et al. |
| 2021/0308066 A1 | 10/2021 | Moskowitz et al. |
| 2021/0308185 A1 | 10/2021 | Moskowitz et al. |
| 2021/0315935 A1 | 10/2021 | Moskowitz et al. |
| 2021/0353680 A1 | 11/2021 | Bhattacharya et al. |
| 2021/0368782 A1 | 12/2021 | Dee et al. |
| 2022/0168353 A1 | 6/2022 | Moskowitz et al. |
| 2022/0211029 A1 | 7/2022 | Moskowitz et al. |
| 2022/0273724 A1 | 9/2022 | Moskowitz et al. |
| 2022/0279777 A1 | 9/2022 | Moskowitz et al. |
| 2023/0112136 A1 | 4/2023 | Jorda et al. |
| 2023/0149467 A1 | 5/2023 | Montgomery et al. |
| 2023/0149468 A1 | 5/2023 | Antebi et al. |
| 2023/0158455 A1 | 5/2023 | Montgomery et al. |
| 2023/0226493 A1 | 7/2023 | Montgomery et al. |
| 2023/0248771 A1 | 8/2023 | Moskowitz et al. |
| 2023/0248772 A1 | 8/2023 | Willard |
| 2023/0285465 A1 | 9/2023 | Moskowitz et al. |
| 2023/0346839 A1 | 11/2023 | Bhattacharya et al. |
| 2023/0356150 A1 | 11/2023 | Montgomery et al. |
| 2024/0066065 A1 | 2/2024 | Moskowitz et al. |

(56) References Cited

U.S. PATENT DOCUMENTS

| | | |
|---|---|---|
| 2024/0139252 A1 | 5/2024 | Moskowitz et al. |
| 2024/0254443 A1 | 8/2024 | Sheik et al. |
| 2024/0277771 A1 | 8/2024 | Moskowitz et al. |
| 2024/0307453 A1 | 9/2024 | Moskowitz et al. |
| 2024/0408141 A1 | 12/2024 | Moskowitz et al. |
| 2025/0000908 A1 | 1/2025 | Moskowitz et al. |

FOREIGN PATENT DOCUMENTS

| | | | |
|---|---|---|---|
| CA | 2136848 A1 | 12/1993 | |
| CA | 2393315 A1 | 6/2001 | |
| CA | 2840568 A1 | 1/2013 | |
| CA | 3053041 A1 | 2/2020 | |
| CN | 101072506 A | 11/2007 | |
| CN | 103524613 A | 1/2014 | |
| CN | 103907595 A | 7/2014 | |
| CN | 108715834 A | 10/2018 | |
| CN | 109942687 A | 6/2019 | |
| EP | 0397890 A1 | 11/1990 | |
| EP | 0815866 A2 | 1/1998 | |
| EP | 0967862 B1 | 1/2000 | |
| EP | 1374890 A2 | 1/2004 | |
| EP | 1652538 A2 | 5/2006 | |
| EP | 1784639 A2 | 5/2007 | |
| EP | 3681518 A1 | 7/2020 | |
| EP | 3307283 B1 | 9/2020 | |
| EP | 3551198 B1 | 2/2022 | |
| JP | H08109136 A | 4/1996 | |
| JP | 2005053841 A | 3/2005 | |
| JP | 2008509924 A | 4/2008 | |
| JP | 2012143554 A | 8/2012 | |
| WO | 1990005461 A1 | 5/1990 | |
| WO | 9012581 A1 | 11/1990 | |
| WO | 1991017655 A1 | 11/1991 | |
| WO | 1992008349 A1 | 5/1992 | |
| WO | 1993000806 A1 | 1/1993 | |
| WO | 1993023997 A1 | 12/1993 | |
| WO | 9428950 A1 | 12/1994 | |
| WO | 1998034478 A1 | 8/1998 | |
| WO | 1999055346 A1 | 11/1999 | |
| WO | 2001007921 A2 | 2/2001 | |
| WO | 2001058266 A1 | 8/2001 | |
| WO | 2003014305 A2 | 2/2003 | |
| WO | 2003039582 A1 | 5/2003 | |
| WO | 2003090839 A1 | 11/2003 | |
| WO | 2004050896 A2 | 6/2004 | |
| WO | 2004078187 A1 | 9/2004 | |
| WO | 2005002499 A2 | 1/2005 | |
| WO | 2005020893 A2 | 3/2005 | |
| WO | 2005021706 A2 | 3/2005 | |
| WO | 2005077299 A1 | 8/2005 | |
| WO | 2005002499 A3 | 11/2005 | |
| WO | 2006020773 A2 | 2/2006 | |
| WO | 2006020773 A3 | 2/2006 | |
| WO | 2006059329 A1 | 6/2006 | |
| WO | 2004050896 A3 | 12/2006 | |
| WO | 2010046949 A1 | 4/2010 | |
| WO | 2011020107 A2 | 2/2011 | |
| WO | 2011020107 A3 | 10/2011 | |
| WO | 2011149110 A1 | 12/2011 | |
| WO | 2012018484 A2 | 4/2012 | |
| WO | 2012074637 A2 | 6/2012 | |
| WO | 2014051537 A1 | 4/2014 | |
| WO | 2014055949 A1 | 4/2014 | |
| WO | 2014066142 A1 | 5/2014 | |
| WO | 2014084263 A1 | 6/2014 | |
| WO | WO-2014118817 A2 * | 8/2014 | ............. A61K 35/19 |
| WO | 2014118817 A3 | 10/2014 | |
| WO | 2015073587 A2 | 5/2015 | |
| WO | 2015191632 A1 | 12/2015 | |
| WO | 2016014854 A1 | 1/2016 | |
| WO | 2016057041 A1 | 4/2016 | |
| WO | 2016077682 A1 | 5/2016 | |
| WO | 2016141325 A1 | 9/2016 | |
| WO | 2016201081 A1 | 12/2016 | |
| WO | 2016205144 A1 | 12/2016 | |
| WO | 2017040238 A1 | 3/2017 | |
| WO | 2017123539 A1 | 7/2017 | |
| WO | 2018084228 A1 | 5/2018 | |
| WO | 2018106250 A1 | 6/2018 | |
| WO | 2019055683 A1 | 3/2019 | |
| WO | 2020023905 A1 | 1/2020 | |
| WO | 2020056009 A1 | 3/2020 | |
| WO | 2020112963 A1 | 6/2020 | |
| WO | 2020113035 A1 | 6/2020 | |
| WO | 2020113090 A1 | 6/2020 | |
| WO | 2020113101 A1 | 6/2020 | |
| WO | 2020165152 A1 | 8/2020 | |
| WO | 2020186193 A1 | 9/2020 | |
| WO | 2020219557 A1 | 10/2020 | |
| WO | 2020227149 A1 | 11/2020 | |
| WO | 2021011857 A1 | 1/2021 | |
| WO | 2021034716 A1 | 2/2021 | |
| WO | 2021034719 A1 | 2/2021 | |
| WO | 2021046409 A1 | 3/2021 | |
| WO | 2021108538 A1 | 6/2021 | |
| WO | 2021108539 A1 | 6/2021 | |
| WO | 2021158622 A1 | 8/2021 | |
| WO | 2021158625 A1 | 8/2021 | |
| WO | 2021158645 A1 | 8/2021 | |
| WO | 2021158646 A1 | 8/2021 | |
| WO | 2021232015 A1 | 11/2021 | |
| WO | 2022103861 A1 | 5/2022 | |
| WO | 2022178177 A1 | 8/2022 | |
| WO | 2022178191 A1 | 8/2022 | |
| WO | 2022178177 A4 | 10/2022 | |
| WO | 2023081804 A1 | 5/2023 | |
| WO | 2023220694 A1 | 11/2023 | |
| WO | 2023220739 A1 | 11/2023 | |
| WO | 2024192173 A1 | 9/2024 | |
| WO | 2024249704 A1 | 12/2024 | |

OTHER PUBLICATIONS

Taune, et al., "Whole blood coagulation assays ROTEM and T-TAS to monitor dabigatran t dabigatran treatment," Thrombosis Research, 2017, 153(30):76-82.

thrombinoscope.com [online], "Thrombin Calibrator," retrieved on Feb. 18, 2021, retrieved from URL , 2 pages.

Török et al., "Preservation of Trehalose-Loaded Red Blood Cells by Lyophilization", Cell Preservation Technology, vol. 3, No. 2, Jul. 11, 2005, pp. 96-11, doi.org/10.1089/cpt.2005.3.96.

Trivedi, et. al., "Freeze-Dried Platelets Promote Clot Formation, Attenuate Endothelial Cell Permeability, And Decrease Pulmonary Vascular Leak in a Murine Model of Hemorrhagic Shock", The Journal of Trauma and Acute Care Surgery, vol. 90, Issue 2, Feb. 1, 2021, pp. 203-214, doi: 10.1097/TA.0000000000002984.

Tsai etal, "Increased risk of bleeding in patients on clopidogrel therapy after drug-eluting stents implantation: insights from the HMO Research Network-Stent Registry (HMORN-stent)", Circulation Cardiovascular Interventions, vol. 3, Issue 3, Jun. 1, 2010, pp. 230-235, DOI: 10.1161/Circinterventions.109.919001.

Tsegaye et al., "Platelet activation suppresses HIV-1 infection of T cells," Retrovirology, 2013, 10:48:00.

T-TAS.info [online], Publications, 2019, retrieved on Aug. 28, 2019, retrieved from URL, 8 pages.

Ullah et al., "A Review on Malarial Parasite", World Journal of Zoology, vol. 10, No. 4, 2015, pp. 285-290, DOI:10.5829/idosi.wjz. 2015.10.4.95268, XP055785474.

Undas et al., "Antithrombotic properties of aspirin and resistance to aspirin: beyond strictly antiplatelet actions", Blood, vol. 109, No. 6, Mar. 15, 2007, pp. 2285-2292, DOI: 10.1182/blood-2006-01-010645.

Valentini et al., "Use of CD9 and CD61 for the characterization of AML-M7 by flow cytometry in a dog," Veterinary Comparative Oncology, Aug. 31, 2011, vol. 10, No. 4, pp. 312-318, DOI: 10.1111/j.1476-5829.2011.00290.x.

Valeri et al., "Freezing human platelets with 6 percent dimethyl sulfoxide with removal of the supernatant solution before freezing and storage at −80° C. without post thaw processing" Transfusion, vol. 45 (12), Dec. 2005, pp. 1890-1898, DOI: 10.1111/j.1537-2995. 2005.00647.x.

(56) References Cited

OTHER PUBLICATIONS

Valeri et al., "Survival of baboon biotin-X-N-hydroxysuccinimide and 11 IIn-oxine-labelled autologous fresh and lyophilized reconstituted platelets," Vox Sanguinis, 2005, 88:122-129.

Van Der Meer et al, Platelet preservation: Agitation and containers, Transfusion and Apheresis Science, vol. 44, Issue 3, Jun. 2011, pp. 297-304, //doi.org/10.1016/j.transci.2011.03.005.

Van Der Meijden et al., "Platelet- and erythrocyte-derived microparticles trigger thrombin generation via factor XIIa", Journal of Thrombosis and Haemostasis, vol. 10, Issue 7, Apr. 26, 2012, pp. 1355-1362, doi.org/10.1111/j.1538-7836.2012.04758.x.

Vibhudutta et al., "Trehalose Stabilized Freeze Dried Human Platelets, Thrombosomes, Reduce Blood Loss in Thrombocytopenic Rabbit Ear Bleed Model by as Much as 89.5%", Cellphire, Inc., www.bodevet.com, Mar. 2017, 1 page, Poster P-0454.

Vibhudutta et al., "Trehalose Stabilized Freeze Dried Human Platelets, Thrombosomes, Persist in Circulation 24 Hours After Infusion and Are Non-Immunogenic in New Zealand White Rabbits", International Society of Blood Transfusion Vox Sanguinis, vol. 99, Suppl. 1, 2010, p. 262, Abstract P-0454.

Vibhudutta et al., "Trehalose Stabilized Freeze Dried Human Platelets, Thrombosomes, Persist In Circulation 24 Hours After Infusion and Are Non-Immunogenic in New Zealand White Rabbits", Cellphire, Inc., 1 page, Poster P-0454.

Vibhudutta et al., "Trehalose Stabilized Freeze Dried Human Platelets, Thrombosomes, Reduce Blood Loss in Thrombocytopenic Rabbit Ear Bleed Model by as Much as 89.5%", International Society of Blood Transfusion Vox Sanguinis, vol. 99, Suppl. 1, 2010, p. 261, Abstract P-0452.

Viswanathan et al., "Clopidogrel Alters Thrombus Quantity and Quality in Patients With Type II Diabetes Mellitus and Stable Coronary Artery Disease", Journal of the American College of Cardiology, vol. 61, No. 10, Mar. 2013, E1154, 1 page.

Vlieghe et al., "Synthetic therapeutic peptides: science and market," Drug Discovery Today, 2010, 15:40-56.

Volz et al., "Inhibition of platelet GPVI induces intratumor hemorrhage and increases efficacy of chemotherapy in mice," Blood, 2019, 133(25):2696-2706.

Wajon et al., "Intraoperative Plateletpheresis and Autologous Platelet Gel Do Not Reduce Chest Tube Drainage or Allogeneic Blood Transfusion After Reoperative Coronary Artery Bypass Graft", Anesth. Analg;., 2001, 93:536-542.

Wang et al., "Commonly used dietary supplements on coagulation function during surgery," Medicines, 2015, 2:157-185.

Wang et al., "Solubility and Molecular Interactions of Trimetazidine Hydrochloride in 12 Monosolvents and Solvent Mixtures of Methanol + (Ethanol, N,N-Dimethylformamide or Ethyl Acetate)", Journal of Chemical Engineering Data, Folume 63, Sep. 6, 2018, pp. 3704-3714, doi.org/10.1021/acs.jced.8b00235.

Wei et al., "ICAM-5/Telencephalin Is a Functional Entry Receptor for Enterovirus D68", Cell Host Microbe, vol. 20, Issue 5, Nov. 9, 2016, pp. 631-641, doi: 10.1016/j.chom.2016.09.013.

Whitman et al., "Design of the Cryptics Trail: A Randomized Controlled Trial Comparing Cryopreserved to Liquid Stored Platelets in Patients Undergoing Cardiac Surgery", Journal of Thoracic and Cardiovascular Surgery, 2022, doi.org/10.1016/j.xjon.2022.11.003.

Whitney et al. "Ratiometric Activatable Cell-Penetrating Peptides Provide Rapid In Vivo Readout of Thrombin Activation", Angewandte Chemie International Edition, vol. 52, Jan. 2, 2013, Issue 1, pp. 325-330, doi: 10.1002/anie.201205721.

Wickramasinghe, "Washing Cryopreserved Blood Products Using Hollow Fibres", Food and Bioproducts Processing, vol. 77, Issue 4, Dec. 1999, pp. 287-292, DOI:org/10.1205/096030899532574.

Wikström et al., "Viability of freeze dried microencapsulated human retinal pigment epithelial cells", European Journal of Pharmaceutical Sciences, vol. 47, Issue 2, Sep. 29, 2012, pp. 520-526, doi: 10.1016/j.ejps.2012.06.014.

Wilkerson et al., "Platelet size, platelet surface-associated IgG, and reticulated platelets in dogs with immune-mediated thrombocytopenia," Veterinary Clinical Pathology, 2001, 30(3):141-149.

Wilson et al., "A simple rapid method for layering blood on Ficoll-Isopaque gradients," Journal of Immunological Methods, 1975, 9(1): 67-68.

Wolkers et al., "Human Platelets Loaded with Trehalose Survive Freeze-Drying", Cryobiology, vol. 42, 2001, pp. 79-87.

WPI Database No. An 2014-E98028 / CN103524613, Jan. 22, 2014: 2 pages.

Wright et al., "Doxorubicin delivery via novel lyophilized/reconstituted platelet-product has anti-cancer activity", Hematology & Transfusion International Journal, vol. 9, Issue 3, 2021, pp. 41-51.

Xu et al., "Doxorubicin-loaded platelets as a smart drug delivery system: An improved therapy for lymphoma", Scientific Reports vol. 7, Article No. 42632, Feb. 15, 2017, 15 pages.

Xu et al., "EACA Loaded Platelets Sustain Clots More Efficiently Than Free EACA", Cellphire, Inc., Jul. 2021, 1 page, Poster.

Xu et al., "EACA Loaded Platelets Sustain Clots More Efficiently Then Free EACA", Cellphire, Inc., 2021. 2 page.

Xu et al., "Human Platelet Derived Lyophilized Hemostatic Retains Hemostatic Properties Heparin Complexation with Protamine", Cellphire, Inc. Jul. 2022, 1 page, Poster.

Xu et al., "Thrombosomes as a Treatment Option for Low-Dose Heparin Reversal", Cellphire Therapeutics, Inc., Rockville, MD, 2020 Annual Meeting, 3 pages.

Yarovoi et al., "Factor VIII ectopically expressed in platelets: efficacy in hemophilia A treatment", Blood 102(12): 4006-4013, 2003.

Zafar et. al., "Badimon Perfusion Chamber: An Ex Vivo Model of Thrombosis", Methods Molecular Biology, vol. 1816, 2018, pp. 161-171, doi: 10.1007/978-1-4939-8597-5_12.

Zhang et al., "Coupling of liquid chromatography with mass spectrometry by desorption electrospray ionization (DESI)", Chemical Communications, Issue 14, Feb. 28, 2011, pp. 4171-4173, doi.org/10.1039/C0CC05736C.

Zhou et al., "Freeze-drying of human platelets: influence of saccharide, freezing rate and cell concentration", Cryoletters, vol. 28, No. 3, May/Jun. 2007, pp. 187-196.

Zhou et al., "Hemostatic and Thrombogenic Properties of Lyophilized Human Platelets", CellPhire, Inc. Jul. 2021, 1 page, Poster.

Zhou et al., "Loading Trehalose into Red Blood Cells by Improved Hypotonic Method," Cell Preservation Technology, 2008, 6(2):119-122.

Zhou et al., "Lyophilized Human Platelets Promote Coagulation in Humanized Mouse VWF Transgenic Models of Hemostasis and Thrombosis", Cellphire, Inc., 2021, 1 page.

"Cryoprotein," The American Heritage® Stedman's Medical Dictionary. Houghton Mifflin Company. Mar. 24, 2010 . . . .

"Expose," http://dictionary.reference.com/browse/expose, accessed Jul. 18, 2009.

"Platelet," The American Heritage® Dictionary of the English Language, Fourth Edition. Houghton Mifflin Company, 2004. Mar. 23, 2010 . . . .

"Rounding," Dictionary.com. Dictionary.com Unabridged (v 1.1 ). Random House, Inc. http://dictionary.reference.com/browse/rounding (accessed: Oct. 27, 2008).

2.palomar.edu [online], "The Five Kingdoms of Life," Feb. 1998, retrieved on May 17, 2021, retrieved from URL ; 18 pages.

Abdelgawwad, et al., "Transfusion of plateletes loaded with recombinant ADAMTS13 is efficacious for inhibiting arterial thrombosis in mice and in human," Arterioscler. Thromb. Vas. Biol., 2018, 38(11):2731-2743.

Abreu-Blanco et al., "Therapeutic effect of Lyophilized human platelets in an in vitro surrogate model of Bernard-Soulier syndrome and in patient samples", Cellphire, Inc., Oct. 14-17, 2023, 2 pages, abstract.

Abreu-Blanco et al., "Therapeutic effect of Lyophilized human platelets in an in vitro surrogate model of Bernard-Soulier syndrome and in patient samples", Cellphire, Inc., Association for the Advancement of Blood & Biotherapies, Oct. 14-17, 2023, 1 page, poster.

(56) References Cited

OTHER PUBLICATIONS

Adams, Ducry et al. ed., "The principles of freeze-drying," DNA Repair Protocols, Methods in Molecular Biology, Humana Press, Clifton, N.J., vol. 368, Chapter 2, 2007, pp. 15-38, doi:10.1007/978-1-59745-362-2_2.

Agam et al. "Passive Participation of Fixed Platelets in Aggregation Facilitated by Covalently Bound Fibrinogen" Blood 61:1, pp. 186-191, 1983.

Ahmadzada, et al., "Fundamentals of siRNA and miRNA therapeutics and a review of targeted nanoparticle delivery systems in breast cancer," Biophysical Reviews, 2018, 10:69-86.

Al Ghaithi et al., "Evaluation of the Total Thrombus-Formation System (T-TAS): application to human and mouse blood analysis", Platelets, vol. 30, Issue 7, Oct. 26, 2018, pp. 893-900, doi: 10.1080/09537104.2018.1535704.

Alexander et at., "A Prospective, Multicenter, Randomized, Open-Label, Phase 2, Parallel, Dose Ranging Multidose Study of Thrombosomes® vs Liquid Stored Platelets (LSP) in Bleeding Thrombocytopenia Patients", Celphire Therapeutics, Inc., NCT04631211, Statistical Analysis Plan, Apr. 2, 2024, 22 pages.

Alquwaizani, et.al., "Anticoagulants: A Review of the Pharmacology, Dosing, and Complications", Current Emergency and Hospital Medicine Reports, vol. 1, No. 2, Apr. 21, 2013, pp. 83-97, DOI: 10.1007/s40138-013-0014-6.

Anonymous, "Bridging Anticoagulation", Circulation, vol. 125, Issue 12, Mar. 27, 2012, pp. e496-e498, doi.org/10.1161/Circulationaha.111.084517.

Appleman et al., "Cryopreservation of canine platelets," Journal of Veterinary Internal Medicine, vol. 23, Issue 1, Jan. 2009, pp. 138-145, doi: 10.1111/j.1939-1676.2008.0225.x.

Arav et. al., "Freeze drying (lyophilization) of red blood cells", Journal of Trauma, May 2011, vol. 70, No. 5, pp. S61-S64, DOI: 10.1097/TA.0b013e31821a6083.

Arnold et al., "The preparation and clinical administration of lyophilized platelet material to children with acute leukemia and aplastic anemia," The Journal of Pediatrics, 1956, 49(5):517-522.

Arruda, "The search for the origin of factor VIII synthesis and its impact on therapeutic strategies for hemophilia A", Haematologica vol. 100, Issue 7, Jul. 2015, pp. 849-850, doi: 10.3324/haematol.2015.129858.

Baroletti et al., "Heparin-Induced Thrombocytopenia", Circulation, vol. 114, Issue 8, Aug. 22, 2006, pp. e355-e356, doi.org/10.1161/Circulationaha.106.632653.

Barroso et. al., "Safety Evaluation of a Lyophilized Platelet Derived Hemostatic Product", Transfusion, vol. 58 (12), Dec. 2018, pp. 2969-2977, DOI: 10.1111/trf.14972.

Böck et al., "Cryopreservation of human platelets with dimethyl sulfoxide: changes in biochemistry and cell function", Transfusion, vol. 35, No. 11, Nov.-Dec. 1995, pp. 921-924, doi: 10.1046/j.1537-2995.1995.351196110896.x.

Bohoněk, Miloš. "Cryopreservation of Platelets: Advances and Current Practice." Cryopreservation Biotechnology in Biomedical and Biological Sciences, Chapter 4. IntechOpen, Dec. 7, 2018, pp. 47-70.

Booth et al., "Lyophilized human platelets are superior to apheresis or fresh-drawn platelets in their ability to accelerate thrombin production", Research and Practice in Thrombosis and Haemostasis, 2022, 1 page, ISTH 2022 Congress, https://abstracts.isth.org/abstract/lyophilized-human-platelets-are-superior-to-apheresis-or-fresh-drawn-platelets-in-their-ability-to-accelerate-thrombin-production/., Abstract PB0154.

Booth et al., "Lyophilized human platelets are superior to apheresis or fresh-drawn platelets in their ability to accelerate thrombin production", Research and Practice in Thrombosis and Haemostasisc, 2022, ISTH2022 Congress Jul. 2022, 1 page, Poster PB0154.

Bullok et al., "Permeation Peptide Conjugates for In Vivo Molecular Imaging Applications", Molecular Imaging, Jan.-Mar. 2006, vol. 5, Issue 1, pp. 1-15.

Bynum et al., "Evaluation of a lyophilized platelet-derived hemostatic product," Transfusion, 2019, 49:1490-1498.

Cap et. al., "Trauma Induced Coagulopathy", Chapter 22: Platelet Transfusion, Springer International Publishing, 2016, pp. 347-376.

Cellphire, Inc. "A Prospective, Multicenter, Randomized, Open-Label Phase 2, Parallel, Dose Ranging Multidose Study of Thrombosomes® vs Liquid Stored Platelets (LSP) in Bleeding Thrombocytopenic Patients" Cellphire Therapeutics, Inc, IND 017156, Informed Consent Form and HIPAA Authorization, Protocol Version 1, NCT04631211, Nov. 10, 2020, ICF Version 2.0, pp. 1-17.

Charkhkar et al., "Amyloid beta modulation of neuronal network activity in vitro", Brain Research, vol. 1629, Dec. 2015, pp. 1-9, doi: 10.1016/j.brainres.2015.09.036.

Chassot et al., "Perioperative Antiplatelet Therapy", American Family Physician, vol. 82, No. 12, Dec. 15, 2010, pp. 1484-1489.

Chelliah et. al., "P-selectin antagonism reduces thrombus formation in humans", Journal of Thrombosis and Haemostasis, vol. 7, No. 11, Nov. 2009, pp. 1915-1919. doi: 10.1111/j.1538-7836.2009.03587.x.

Chen et al., "Advance of molecular imaging technology and targeted imaging agent in imaging and therapy," Biomed. Res. Int., 2014, 819324, 12 pages.

Chen et al., "Expanding the Potential of Doxorubicin-Loaded Cryopreserved Platelets for Targeted Cancer Drug Delivery", Cellphire, Inc., 21st International Drug Delivery and Nanomedicines Symposium, Sep. 15-17, 2023, 1 page, poster.

Chen et al., "Modifying murine von Willebrand factor AI domain for in vivo assessment of human platelet therapies," Nature biotechnology, Jan. 2008, 26(1):114-119.

Chen et al., "Stabilizaton of peptides against proteolysis through disulfide-bridged conjugation with synthetic aromatics," Org. Biomol. Chem., 2017, 15(8):1921-1929.

Chen et al., "Stabilized Platelets: A Drug Delivery System for Potential Human Hepatocellular Carcinoma Therapy", Research and Practice in Thrombosis and Haemostasis, 2023, ISTH 2023, Montréal, Jun. 24-28, 2023, 1 page, Poster PB0731.

Christenson et al., "Autologous fibrin glue reinforced by platelets in surgery of ascending aorta", Thorac. Cardiovasc. Surg., vol. 52, p. 225-229, 2004.

Christopher et al., "MicroRNA therapeutics: discovering novel targets and developing specific therapy," Perspect. Clin. Res., 2016, 7(2):68-74.

Cid et at., "24-h continuous infusion of platelets for patients with platelet transfusion refractoriness", British Journal of Haematology, vol. 181, No. 3, Mar. 14, 2017, pp. 386-389, doi.org/10.1111/bjh.14572.

Clemmons et al., "Acquisition and aggregation of canine blood platelets: basic mechanisms of function and differences because of breed origin," Americanjournal of veterinary research, Jan. 1, 1984, 45(1):137-144.

Cogswell et al., "Amyloid-Related Imaging Abnormalities with Emerging Alzheimer Disease Therapeutics: Detection and Reporting Recommendations for Clinical Practice", American Journal of Neuroradiology, vol. 43, Issue 9, Sep. 2022, pp. E19-E35, doi: 10.3174/ajnr.A7586.

Colman, "Are hemostasis and thrombosis two sides of the same coin?", Journal of Experimental Medicine, Mar. 20, 2006, vol. 203, No. 3, pp. 493-495, doi: 10.1084/jem.20060217.

Comont et al., "Platelet transfusion refractoriness in patients with acute myeloid leukemia treated by intensive chemotherapy", Leukemia Research, vol. 61, Oct. 2017, pp. 62-67, doi: 10.1016/j.leukres.2017.08.015.

Cowles, "Anticoagulant effect of aspirin goes beyond platelet aggregation", Hematology/Oncology, May 1, 2007, 3 pages.

Cox, et al., "Platelets and the innate immune system: mechanisms of bacterial-induced platelet activation," Journal of Thrombosis and Haemostasis, 2011, 9:1097-1107.

Crowe et al., "Freeze-dried platelets: Moving towards clinical use", Cryobiology, vol. 66, Issue 3, Jun. 2013, p. 348, Abstract, doi.org/10.1016/j.cryobiol.2013.02.028.

Crowe et. al., "Stabilization of Dry Mammalian Cells: Lessons from Nature", Integrative and Comparative Biology, vol. 45, Issue 5, Nov. 2005, pp. 810-820, https://doi.org/10.1093/icb/45.5.810.

(56) References Cited

OTHER PUBLICATIONS

Crowe et. al., "Stabilization of membranes in human platelets freeze-dried with trehalose", Chemistry and Physics of Lipids, vol. 122, Issues 1-2, Jan. 2003, pp. 41-52, https://doi.org/10.1016/S0009-3084(02)00177-9.
Daidone, "Usefulness of the Total Thrombus-formation Analysis System (T-TAS) in the diagnosis and characterization of von Willebrand disease," Haemophillia, 2016, 22:949-956.
Kuhn et al., "Assessing Circulation Persistence of Human Platelet Products in a NOD-SCID Mouse Model", Research and Practice in Thrombosis and Haemostasis, 2022, ISTH 2022 Congress Jul. 2022, 1 page, Poster PB0874.
Kuhn et al., "Assessing Circulation Persistence of Human Platelet Products in a NOD-SCID Mouse Model", Research and Practice in Thrombosis and Haemostasis, 2022, 2 pages, ISTH 2022 Congress, https://abstracts.isth.org/abstract/assessing-circulation-persistence-of-human-platelet-products-in-a-nod-scid-mouse-model/, Abstract PB0874.
Kuhn et al., "Mechanism of Action of a Freeze-dried Platelet-derived Hemostatic Product", Cellphire, Inc. Cellular Therapeutics in Trauma and Critical Care, May 8-11, 2023, 1 page, poster.
Kuhn et al., "Mechanisms of action of an investigational new freeze-dried platelet-derived hemostatic product", Journal of Thrombosis and Haemostasis, Dec. 9, 2023, 4 pages, doi.org/10.1016/j.jtha.2023.11.022, Abstract.
Lam et al., "siRNA versus miRNA as therapeutics for gene silencing," Molecular Therapy—Nucleic Acids, 2015, 4:e252.
Lannan et al., "Breaking the Mold: Transcription Factors in the Anucleate Platelet and Platelet-Derived Microparticles," Front Imunnol., 2015, 6:48, 17 pages.
Lassila et. al., "Dynamic Monitoring of Platelet Deposition on Severely Damaged Vessel Wall in Flowing Blood. Effects of Different Stenoses on Thrombus Growth", Arteriosclerosis, vol. 10, No. 2, Mar.-Apr. 1990, pp. 306-315, doi: 10.1161/01.atv.10.2.306.
Lee et al., "High Efficiency Transfection and Preservation of Platelets with Tumor Suppressing Short RNA", Research and Practice in Thrombosis and Haemostasis, Jul. 2020, 1 page, ISTH 2020 Congress, Poster PB1724.
Lee et al., "High Efficiency Transfection and Preservation of Platelets with Tumor Suppressing Short RNA", Research and Practice in Thrombosis and Haemostasis, 2020; 4 (Suppl 1). 2 pages, ISTH 2020 Congress, https://abstracts.isth.org/abstract/high-efficiency-transfection-and-preservation-of-platelets-with-tumor-suppressing-short-rna/, Abstract PB1724.
Lee et al., "Lyophilized Human Platelets Exhibit Adhesive Interactions with *Staphylococcus aureus*", Research adn Practice in Thrombosis and Haemostasis, 2020, 1 page, Poster PB1816.
Lee et al., "Lyophilized Human Platelets Exhibit Adhesive Interactions with *Staphylococcus aureus*", Research and Practice in Thrombosis and Haemostasis, 2020; 4 (Suppl 1), 2 pages, ISTH 2020 Congress, https://abstracts.isth.org/abstract/lyophilized-human-platelets-exhibit-adhesive-interactions-with-staphylococcus-aureus/., Abstract PB1816.
Lee et al., "Novel treatment modalities: New platelet preparations and subsitutes," British journal of haematology, Sep. 2001, 114(3):496-505.
Li et al., "Extended antiplatelet therapy with clopidogrel alone versus clopidogrel plus aspirin after completion of 9- to 12-month dual antiplatelet therapy for acute coronary syndrome patients with both high bleeding and ischemic risk. Rationale and design of the OPT-BIRISK double-blinded, placebo-controlled randomized trial", American Hear Journal, vol. 228, Oct. 2020, pp. 1-7, https://doi.org/10.1016/j.ahj.2020.07.005.
Lo et al., "Development of a multi-compartment microfiltration device for particle fractionation" 16th International Conference on Miniaturized Systems for Chemistry and Life Sciences, MicroTAS 2012—Okinawa, Japan, Oct. 28, 2012-Nov. 1, 2012, 3 pages.
Lucking et. al., "Characterisation and reproducibility of a human ex vivo model of thrombosis", Thrombosis Research, vol. 126, No. 5, Nov. 2010, pp. 431-435, doi: 10.1016/j.thromres.2010.06.030.

Luo et al., "Construction and in vitro studies of magnetic-apoferritin nanocages conjugated with KGDS peptide targeted at activated platelets for the MRI diagnosis of thrombus," Journal of Nanoparticle Research, vol. 21, Issue 8, Aug. 2019, pp. 1-12.
Mailer et al., "Commentary on "Pharmacological profile of asundexian, a novel, orally bioavailable inhibitor of factor XIa": Small molecule factor XIa inhibitor asundexian allows for safer anticoagulation", Journal of Thrombosis and Haemostasis, vol. 20, Issue 6, Jun. 2022, pp. 1309-1311, https://doi.org/10.1111/jth.15722.
Makielski et al., "Development and implementation of a novel immune thrombocytopenia bleeding score for dogs," J. Vet. Intern. Med., 2018, 32(3):1-10.
Marder, "Bleeding Complications of Thrombolytic Treatment", American Journal of Hospital Pharmacy, vol. 47, Suppl 2, Sep. 1990, pages S15-S19.
Marris, "The war against wounds", Nature, Mar. 21, 2007, Issue 446, pp. 369-371.
Mathews et al., "Development of Lyophilized Platelet-Derived Extracellular Vesicles for Multiple Indications", Cellphire, Inc., Oct. 2020, 1 page, Poster.
Mathews et al., "Development of Lyophilized Platelet-Derived Extracellular Vesicles for Multiple Indications", Chellphire, Inc., 2020, 1 page, Abstract.
Mazzucco et al., "The use of autologous platelet gel to treat difficult-to-heal wounds: a pilot study," Transfusion, 2004, 44:1013-1018.
McCarrel, et. al., "Temporal Growth Factor Release from Platelet-Rich Plasma, Trehalose Lyophilized Platelets, and Bone Marrow Aspirate and Their Effect on Tendon and Ligament Gene Expression" Journal of Orthopaedic Research : Official Publication of the Orthopaedic Research Society, vol. 27(8), Aug. 1, 2009, pp. 1033-1042, DOI: 10.1002/jor.20853.
MedWow, "Manufacturer Specifications—CS-2000 Plus, Baxter," Apr. 19, 2011, retrieved on Sep. 26, 2019 from http://www.medwow.com/med/apheresis-machine/baxter/cs-3000-plus/5782.model-spec, 2 pages.
Mehendale, et. al., "Platelet Enrichment From Whole Blood in a Clog-Free Microfluidic Radial Pillar Device (RAPID)", Biomedical Microdevices, bioRxiv, Oct. 4, 2017, DOI: https://doi.org/10.1101/197749.
Mehendale, et. at., "Platelet Enrichment in a Continuous and Clog-Free Microfluidic Filter With Sunflower Head Geometry", 20th International Conference on Miniaturized Systems for Chemistry and Life Sciences, Dublin, Ireland, Oct. 9-13, 2016, pp. 272-273.
Meisel et. al., "A Simplified Direct Lipid Mixing Lipoplex Preparation: Comparison of Liposomal-, Dimethylsulfoxide-, and Ethanol-Based Methods", Scientific Reports, vol. 6, Article 27662, Jun. 21, 2016, 12 pages, doi: 10.1038/srep27662.
Merten et al., "Platelet Microparticles Promote Platelet Interaction with Subendothelial Matrix in a Glycoprotein lib/IIIa Dependent Mechanism", Circulation, 1999, 99:2577-2582.
Miajlovic et al., "Both complement- and fibrinogen-dependent mechanisms contribute to platelet aggregation mediated by *Staphylococcus aureus* clumping factor B," Infection and Immunity, 2007, 75(7):3335-3343.
Midgett et al., "Combination of freeze-dry microscopy, differential scanning calorimetry, and electron microscopy analysis as a guide for lyophilization cycle optimization to enhance Thrombosomes function", Cryobiology, vol. 63, Issue 3, 2011, p. 320, Abstract, doi:10.1016/j.cryobiol.2011.09.054.
Mihatov et al., "Individualizing Dual Antiplatelet Therapy (DAPT) Duration Based on Bleeding Risk, Ischemic Risk, or Both: An Analysis From the DAPT Study", Cardiovascular Revascularization Medicine, vol. 41, Aug. 2022, pp. 105-112, https://doi.org/10.1016/j.carrev.2022.01.006.
Millipore Sigma, "Dulbecco's Modified Eagle's Medium (DMEM)Formulation", Merck KGaA, Sigma-Aldrich Solutions, 2023, 15 pages, retreived from https://www.sigmaaldrich.com/US/en/technical-documents/technical-article/cell-culture-and-cell-culture-analysis/mammalian-cell-culture/dulbecco-modified-eagle-medium-formulation.

(56) References Cited

OTHER PUBLICATIONS

Mishra et al., "Cell-penetrating peptides and peptide nucleic acid-coupled MRI contrast agents: evaluation of cellular delivery and target binding." Bioconjugate Chemistry, vol. 20, Issue 10, Oct. 21, 2009, pp. 1860-1868, doi:10.1021/bc9000454.
Mokobi, "Types of Plant Cell—Definition, Structure, Functions, Diagrams," microbenotes.com [online], Feb. 25, 2020, retrieved May 17, 2021, retrieved from URL , 31 pages.
Montague, "Strategies to Improve Haemostasis in Trauma: Evaluation of Thrombosomes in the Presence of Native Platelet Dysfunction", vol. 100, Issue Suppl 3, 2014, pp. A91-A92, DOI:10.1136/heartjnl-2014-306118.158.
Montecinos et al., "Selective targeting of bioengineered platelets to prostate cancer vasculature: new paradigm for the therapeutic modalities," 2015, 19(7):1530-1537.
Morris et al., "A peptide carrier for the delivery of biologically active proteins into mammalian cells," Nature Biotechnoloe:v, 2001, 19:1173-1176.
Morrison et al., "Storage of apheresis platelet concentrates after manual replacement of >95% of plasma with PAS 5", Vox Sanguinis, vol. 107; Issue 3, May 7, 2014, pp. 247-253, XP055759704, doi:10.1111/vox.12157.
Moskowitz et al., "A Freeze-Dried Platelet-Derived Hemostatic Agent is Partially Resistant to Fibrinolysis In Vitro", Cellphire Therapeutics, Military Health System Research Symposium, (MHSRS-24-11499), Aug. 2024, 1 page, poster.
Moskowitz et al., "A Freeze-Dried Platelet-Derived Hemostatic Agent is Partially Resistant to Fibrinolysis In Vitro", Cellphire Therapeutics, Military Health System Research Symposium, (MHSRS-24-11499), Aug. 2024, 2 pages, abstract.
Moskowitz et al., "A Prospective, Multicenter, Randomized, Open-Label,Phase 2, Parallel, Dose Ranging Multidose Study of Thrombosomes® vs Liquid Stored Platelets (LSP) in Bleeding Thrombocytopenic Patients with Hematological Malignancies", Cellphire Therapeutics, Inc., presented at Association for the Advancement of Blood & Biotherapies Oct. 19, 2024, 22 pages.
Moskowitz et al., "Cryopreserved Platelets Prepared by Novel Allogenic Pooling and Post-thaw Processes are Stable at Elevated Temperatures", Cellphire, Therapeutics, Military Health System Reserach Symposium, (MHSRS-24-11477), Aug. 2024, 1 page, poster.
Moskowitz et al., "Freeze Dried Platelet Derivatives (Thrombosomes®) Retain Hemostatic Properties During Heparin Complexation with Protamine", Research and Practice in Thrombosis and Haemostasis, 2022, 2 pages, ISTH 2022 Congress, https://abstracts.isth.org/abstract/freeze-dried-platelet-derivatives-thrombosomes-retain-hemostatic-properties-during-heparin-complexation-with-protamine/., Abstract PB0880.
Moskowitz et al., "Freeze-Dried Platelets Decrease Bleeding in Refractory Thrombocytopenic Patients with Hematological Malignancies", AABB Annual Meeting 2024, abstract submission, 2 pages.
Moskowitz et al., "Hemostatic Properties of Infusible Trehalose-Stabilized Lyophilized Platelet Derivatives", Blood, vol. 104, Issue 11, Nov. 16, 2004, p. 834, doi.org/10.1182/blood.V104.11.834.834, Abstract.
Moskowitz et al., "Natural History of Bleeding, Transfusion, and Antibody Prevalence in a Subset of Hermansky-Pudlak Syndrom patients: Effects of Freeze-Dried Lyophilized Platelet Derived Hemostat Ex Vivo", Trombosis & Hemostasis Summit 2024, Cellphire Therapeutics, Inc. Apr. 5, 2024, 1 page, Abstract.
Moskowitz et al., "Natural History of Bleeding, Transfusion, and Antibody Prevalence in a Subset of Hermansky-Pudlak Syndrom patients: Effects of Freeze-Dried Lyophilized Platelet Derived Hemostat Ex Vivo", Trombosis & Hemostasis Summit 2024, Cellphire Therapeutics, Inc. Apr. 5, 2024, 1 page, Poster.
Moskowitz et al., "Stabilized Platelets: A Drug Delivery System for Potential Human Hepatocellular Carcinoma Therapy", Research and Practice in Thrombosis and Haemostasis, vol. 7 (Suppl. 2) Oct. 2023, pp. 709-710, doi.org/10.1016/j.rpth.2023.101329, Abstract PB0731.
Moskowitz, "Thrombosomes for the Treatment of Bleeding Associated with Aggressive Anticoagulation", Cellphire, Inc., Dec. 2021, 40 pages, Posters.
Human Translation of Chinese patent No. CN103907595 A Published Jul. 9, 2014, Trehalose-containing platelet low temperature preservation solution and application thereof, First Inventor Zhao Shuming.
Machine Language Translation of Chinese Patent No. CN108715834 A Titled [EN], "A Kind of Platelet Lysates Liquid and Preparation Method There of Rich in CD41+, CD81+ Micro-Capsule", Oct. 30, 2018, 10 pages.
Machine Language Translation of Chinese Patent No. CN109942687 A, Shen et at., Titled [EN], "68Ga Marks EACA Modification c-Met Molecular Imaging Probe and Preparation and Application", Jun. 28, 2019, 10 pages.
Machine Language Translation of Japanese Patent JP2012143554 A2 Titled "[EN] Polysulfone-Based Hollow Fiber Membrane, Hollow Fiber Membrane Module for Cleaning Platelet Suspension, and Cleaning Method of Platelet Suspension.", Aug. 2, 2012, 33 pages.
Machine Language Translation of WO2018084228A1: Nagamura et al., Titled [EN], "Solution for Cryopreservation of Animal Cells or Animal Tissues, Cryopreserved Product, and Cryopreservation Method", May 11, 2018, 16 pages.
Machine Language Translation of Yamamoto, "Appropriate use of platelet preparations", Journal of Thrombosis and Hemostasis, vol. 29, No. 6, 2018, pp. 647-650.
Yamamoto, "Appropriate use of platelet preparations", Journal of Thrombosis and Hemostasis, vol. 29, No. 6, 2018, pp. 647-650.
Müller et. al., "Factor XI and XII as antithrombotic targets", Current Opinion in Hematology, vol. 15, No. 5, Sep. 2011, pp. 349-355, doi: 10.1097/MOH.0b013e3283497e61.
Mullin, et.al., "Doxorubicin chemotherapy for presumptive cardiac hemangiosarcoma in dogs", Veterinary and Comparative Oncology, vol. 14, Issue 4, Dec. 18, 2014, 13 pages, doi:10.1111/vco.12131.
Murphy et al., "Platelet transfusions: The problem of refractoriness", Blood Reviews, vol. 4, Issue 1, Mar. 1990, pp. 16-24, doi.org/10.1016/0268-960X(90)90013-I.
NasrEldin, "Effect of cold storage on platelets quality stored in a small containers: Implications for pediatric transfusion", Pediatric Hematology Oncology Journal, vol. 2, Issue 2, Aug. 2017, pp. 29-34, doi.org/10.1016/j.phoj.2017.07.001.
Natan et al., "Freeze-drying of mononuclear cells derived from umbilical cord blood followed by colony formation", PLoS One, Apr. 21, 2009, vol. 4, Issue 4, e5240, 12 pages, DOI: 10.1371/journal.pone.0005240.
Nieuwland et al., "Cell-Derived Microparticles Generated in Patients During Cardiopulmonary Bypass Are Highly Procoagulant", Circulation, 1997, 96:3534-3541.
Novakowski et al., "Delivery of mRNA to platelets using lipid nanoparticles" Scientific Reports, vol. 9, Article 552, Jan. 24, 2019, 11 pages, doi: 10.1038/s41598-018-36910-2.
O'Brien, et al., "Multiple mechanisms for the activation of human platelet aggregation by *Staphylococcus aureus*: roles for the clumping factors ClfA and ClfB, the serine-aspartate repeat protein SdrE and protein A," Molecular Microbiology, 2002, 44(4):1033-1044.
Ogiwara, et al., "Procoagulant Activity of Antifibrinolytic Agents; A Novel Hemostatic Mechanism of Tranexamic Acid and Epsilon-Aminocaproic Acid", Blood, Nov. 19, 2010, vol. 116, Issue 21, Abstract 1151, 3 pages, https://doi.org/10.1182/blood.V116.21.1151.1151.
Ohanian, et. al., "Freeze-Dried Platelets Are a Promising Alternative in Bleeding Thrombocytopenic Patients with Hematological Malignancies", American Journal of Hematology, vol. 97, Issue 3, Mar. 1, 2022, pp. 256-266, doi: 10.1002/ajh.26403.
Oikarinen et al., "Augmentation of the narrow traumatized anterior alveolar ridge to facilitate dental implant placement," Dent. Traumatol., 2003, 19:19-29.
Oliver, "Dry state preservation of nucleated cells: progress and challenge," Cryobiology, Dec. 2011, vol. 63, Issue 3, p. 307, abstract, DOI:10.1016/j.cryobiol.2011.09.007.

(56) References Cited

OTHER PUBLICATIONS

Orser et al., "Loading Platelets with Biological Agents for Enhanced Local Delivery", Cellphire, Inc., May 8, 2019, 14 pages, retrieved from https://www.bodevet.com/wp-content/uploads/2019/07/Loading-Platelets-with-Biological-Agents.pdf.

Pan et al., "Wound healing monitoring using near infrared fluorescent fibrinogen", Biomedical Optics Express, Jul. 27, 2010, vol. 1, Issue 1, pp. 285-294, doi: 10.1364/boe.1.000285.

Pati et al., "Targeting the Endotheliopathy of Trauma in Hemorrhagic Shock and Traumatic Brain Injury with Freeze-Dried Platelets", Defense Technical Information Center, U.S. Army Medical Research and Development Command, Medicine and Medical Research; Biology, Sep. 1, 2020, 22 pages, https://apps.dtic.mil/sti/pdfs/AD1112058.pdf.

Pati et al., "Targeting the Endotheliopathy of Trauma in Hemorrhagic Shock and Traumatic Brain Injury with Freeze-Dried Platelets", Defense Technical Information Center, Sep. 1, 2020, 2 pages, Abstract.

Pemmaraju et al., "Bleeding Risk in Thrombocytopenia Cancer Patients with Venous Thromboembolism (VTE) Receiving Anticoagulation", Blood, vol. 120, Issue 21, Nov. 16, 2012, 3 pages, doi.org/10.1182/blood.V120.21.3408.3408, Abstract 3408.

Pierce et al., "Platelet-derived growth factor and transforming growth factor-beta enhance tissue repair activities by unique mechanisms", J. Cell Biol., 1989, 109:429-440.

Pietramaggiori et al., "Freeze-dried platelet-rich plasma shows beneficial healing properties in chronic wounds", Wound Repair and Regeneration, vol. 14, Issue 5, Sep. 29, 2006, pp. 573-580, doi.org/10.1111/j.1743-6109.2006.00164.x.

Pietramaggiori et al., "Trehalose Lyophilized Platelets for Wound Healing", Wound Repair and Regeneration : Official Publication of the Wound Healing Society [and] the European Tissue Repair Society, vol. 15 (2), Mar. 9, 2007, pp. 213-220. doi:10.1111/j.1524-475X.2007.00207.x.

Powner et al., "Counteracting the Effects of Anticoagulants and Antiplatelet Agents During Neurosurgical Emergencies", Neurosurgery, vol. 57, No. 5, Nov. 2005 pp. 823-831.

Prior et al., "A Sprayable Hemostat Containing Fibrillar Collagen, Bovine Thrombin, and Autologous Plasma", Ann. Thorac. Surg., 1999, 68:479-485.

Read et. al., "Preservation of hemostatic and structural properties of rehydrated lyophilized platelets: potential for long-term storage of dried platelets for transfusion", Proceedings of the National Academy of Sciences of the USA, vol. 92, Jan. 1995, pp. 397-401, DOI: 10.1073/pnas.92.2.397.

Reddoch et al., "Extended Storage of Refrigerated Platelets in Isoplate and Intersol PAS: An Evaluation of Two FDA-Approved Methods of Collection", Blood, vol. 128, Issue 22, Dec. 2, 2016, 3 pages, doi.org/10.1182/blood.V128.22.2631.2631.

Reuss et al., "Intracellular delivery of carbohydrates into mammalian cells through swelling-activated pathways", The Journal of Membrane Biology, vol. 200, Issue 2, Jul. 15, 2004, pp. 67-81, doi: 10.1007/s00232-004-0694-7.

Robson, et. al., "Coronavirus RNA Proofreading: Molecular Basis and Therapeutic Targeting", Molecular Cell, vol. 79, No. 5, Sep. 3, 2020, pp. 710-727, DOI:10.1016/j.molcel.2020.07.027, XP055785471.

Rosing et al., "Impaired factor X and prothrombin activation associated with decreased phospholipid exposure in platelets from a patient with a bleeding disorder", Blood, 1985, 65:1557-1561.

Rowley et al., "Platelet mRNA: the meaning behind the message," Curr. Opin. Hematol., 2012, 19(5):385-391.

Roytman et al., "Amyloid-Related Imaging Abnormalities: An Update", American Journal of Roentgenol, Issue 220, Issue 4, Nov. 2, 2022, pp. 562-574, doi: 10.2214/AJR.22.28461.

Samanbar et al., "Evaluation of the Hemostatic Ability of the New Device 'Total Thrombus Formation Analysis System' (T-TAS) for Thrombocytopenic Patients. Invitro effect of lyophilized human platelets", Research and Preactice in Thrombosis and Haemostasis, Jul. 2022, 1 page, Poster.

Samanbar et al., "Evaluation of the hemostatic ability of the new device Total Thrombus Formation Analysis System (T-TAS) for thrombocytopenic patients. In vitro effect of Thrombosomes®", Research and Practice in Thrombosis and Haemostasis, 2022, 2 pages, ISTH 2022 Congress, https://abstracts.isth.org/abstract/evaluation-of-the-hemostatic-ability-of-the-new-device-total-thrombus-formation-analysis-system-t-tas-for-thrombocytopenic-patients-in-vitro-effect-of-thrombosomes/., Abstract PB0854.

Samanbar et al., "Hemostatic Ability of Thrombosomes® in Blood from Thrombocytopenic Patients Using the Total Thrombus Formation Analysis System (T-TAS) and Confocal Microscopy in Microfluidic Chambers", Blood, Nov. 15, 2022, 140 (Supplement 1), pp. 11242-11243, doi.org/10.1182/blood-2022-169346.

Sane et al., "Bleeding During Thrombolytic Therapy for Acute Myocardial Infarction: Mechanisms and Management", Annals of Internal Medicine, vol. 111, No. 12, Dec. 15, 1989, pp. 1010-1022.

Scheinkönig et al., "Adoption of long-term cultures to evaluate the cryoprotective potential of trehalose for freezing hematopoietic stem cells", Bone Marrow Transplantation, September, vol. 34, Issue 6, Sep. 2004, pp. 531-536, doi: 10.1038/sj.bmt.1704631.

Schoug, et.al., "Differential effects of polymers PVP90 and Ficoll400 on storage stability and viability of Lactobacillus coryniformis Si3 freeze-dried in sucrose", Journal of Applied Microbiology, vol. 108, No. 3, pp. 1032-1040, Feb. 8, 2010.

Serebruany, et al., "Crossreactivity of Human versus Swine Platelet Surface Antigens Is Similar for Glycoproteins Ib and IIIa, but Not for the Glycoprotein IIb/IIIa Complex," Journal of Thrombosis and Thrombolysis, vol. 5, Issue 1, 1998, pp. 37-41, doi: 10.1023/a:1008867930862.

Sheik et al., "Stably Loading Human Platelets with Gadolinium Conjugates to Enhance Magnetic Resonance Imaging", Cellphire, Inc., 2020, 1 page.

Sheik et al., "Stably Loading Human Platelets with Gadolinium Conjugates to Enhance Magnetic Resonance Imaging", Cellphire, Inc., 2020, 3 pages, poster.

Shi et al., "Impact of Anti-amyloid-β Monoclonal Antibodies on the Pathology and Clinical Profile of Alzheimer's Disease: A Focus on Aducanumab and Lecanemab", Frontiers in Aging Nuroscience, vol. 14, Article 870517, Apr. 12, 2022, 11 pages, doi: 10.3389/fnagi.2022.870517.

Sibbing, et. al., "Antiplatelet effects of clopidogrel and bleeding in patients undergoing coronary stent placement", Journal of Thrombosis and Haemostasis, vol. 8, Issue 2, pp. 250-256, DOI: 10.1111/j.1538-7836.2009.03709.x.

Sims et al., "Complement Proteins C5b-9 Cause Release of Membrane Vesicles from the Platelet Surface That Are Emiched in the Membrane Receptor for Coagulation Factor Va and Express Prothrombinase Activiy", J. Biol Chem., 1988, 263:18205-18212.

Sims et al., "Regulatory control of complement on blood platelets. Modulation of platelet procoagulant responses by a membrane inhibitor of the C5b-9 complex", J Biol. Chem., 1989, 264:19228-19235.

Srivastava, et. al., "The rebirth of the contact pathway: a new therapeutic target", Current Opinion in Hematology, vol. 27, No. 5, Sep. 2020, pp. 311-319, doi: 10.1097/MOH.0000000000000603.

Steed, "The role of growth factors in wound healing" Surgical Clinics of North America, vol. 77, No. 3, Jun. 1997, pp. 575-586, doi.org/10.1016/S0039-6109(05)70569-7.

Strober, "Trypan blue exclusion test of cell viability", Current Protocols in Immunology, 1997, A.3B.1-A.3B.2.

Strong, ed., "Indications for Platelet Transfusion Therapy," Transfusion Medicine Bulletin, Vo. 2, No. 2, Jul. 1999, http://www.scbinfo.org/publications/bulletin_v2_n2.htm, pp. 1-6.

Sum et al., "Wound-healing properties of trehalose-stabilized freeze-dried outdated platelets", Transfusion, vol. 47, Issue 4, Apr. 2007, pp. 672-679, doi: 10.1111/j.1537-2995.2007.01170.x.

Swami, et.al., "von Willebrand Disease: A Concise Review and Update for the Practicing Physician", Clinical and Applied Thrombosis/Hemostasis, vol. 23 (8), Nov. 2017, pp. 900-910, DOI: 10.1177/1076029616675969.

Székely et al., "Antifibrinolytics", Heart, Lung and Vessels, 2014, vol. 6, Issue 1, pp. 5-7.

(56) References Cited

OTHER PUBLICATIONS

Tacar et al., "Doxorubicin: an update on anticancer molecular action, toxicity and novel drug delivery systems", The Journal of Pharmacy and Pharmacology vol. 65, Issue 2, Feb. 1, 2013, pp. 157-170, doi.org/10.1111/j.2042-7158.2012.01567.x.

Daly et al., "Hemostatic regulators of tumor angiogenesis: a source of antiangiogenic agents for cancer treatment?" Journal of the National Cancer Institute, 2003, 95(22):1660-1673.

Dee et al., "Trehalose Stabilized Freeze Dried Human Platelets, Thrombosomes, Express Surface Markers, Thromboelastogram (TEG) Values and Size Distribution Similar to Two to Three Day Old Stored Platelets", Cellphire, Inc., P-0453, 2019, 1 page, Poster.

Dee et al., "Trehalose Stabilized Freeze Dried Human Platelets, Thrombosomes, Express Surface Markers, Thromboelastogram (TEG) Values and Size Distribution Similar to Two to Three Day Old Stored Platelets", International Society of Blood Transfusion Vox Sanguinis, vol. 99, Suppl. 1, P-0453, 2010, p. 262, Abstract.

Dennison, "A Simple and Universal Method for Making up Buffer Solutions", Biochem Edu., vol. 16, No. 4, 1988, XP023535876, DOI: 10.1016/0307-4412(88)90123-9.

diapharma.com [online], "DiaPhannaProductList," retrieved on Feb. 18, 2021, retrieved from URL, 4 pages.

Dickerson et al., "Lyophilized Human Platelets Restore Hemostasis in the Presence of the P2Y12 Inhibitors Cangrelor, Ticagrelor and Clopidogre", American Society of Hematology, Blood, vol. 136, Noumer Supplement 1, 3.22 Disorders of Coagulation or Fibrinolysis, Nov. 5, 2020, 6 pages.

Dickerson et al., "Lyophilized Human Platelets Restore Hemostasis in the Presence of the P2Y12 Inhibitors Cangrelor, Ticagrelor and Clopidogrel", Cellphire Therapeutics Inc., Rockville, MD, 7 pages, Poster.

Dickerson et al., "Lyophilized Human Platelets Restore Hemostasis in the Presence of the P2Y12 Inhibitors Cangrelor, Ticagrelor and Clopidogrel", Cellphire, Inc., 2020, 6 pages, Poster.

Dickerson et al., "Lyophilized human platelets support thrombosis unlike normal platelets in the presence of GPIIb/IIIa antagonists", Cellphire, Inc., AS-ISTH-2021-01436, 2021. 2 pages, Abstract.

Dickerson et al., "Lyophilized human platelets support thrombosis unlike normal platelets in the presence of GPIIb/IIIa antagonists", Cellphire Therapeutics, ISth Virtual Congress, Jul. 2021, 1 page, Poster.

Dickerson et al., "Thrombosomes as a Treatment Option for Low-Dose Heparin Reversal", Cellphire, Inc, Oct. 2020. 1 page, Poster.

Dickson et al., "A scalable, micropore, platelet rich plasma separation device." Biomedical Microdevices, vol. 14 (6), Jul. 2012, pp. 1095-1102. DOI:10.1007/s10544-012-9675-2.

Dielis et al., "Coagulation factors and the protein C system as determinants of thrombin generation in a normal population," J. Thromb. Haemost., 2008, 6:125-131.

Diener, "Antiplatelet agents and randomized trials," Review in Neurological Diseases, 2007, 4(4):177-183.

Dinçer et al., "Effect of taurine on wound healing", Amino Acids, vol. 10, Issue 1, Mar. 1996, pp. 59-71, doi:10.1007/BF00806093.

Dong, et al., "Ristocetin-dependent, but not botrocetin-dependent, binding of von Willebrand factor to the platelet glycoprotein Ib-IX-V complex correlates with shear-dependent interactions," Blood, 2001, 97:162-+168.

Dumont et al., "Feasibility evaluation of two novel systems for the automated preparation and extended storage of DMSO cryopreserved platelets", Transfusion, Vlume 63, No. 8, Jun. 26, 2023, pp. 1554-1562, https://doi.org/10.1111/trf.17464.

Dumont, et. al., "A randomized controlled trial evaluating recovery and survival of 6% dimethyl sulfoxide-frozen autologous platelets in healthy volunteers", Transfusion vol. 53(1), Jan. 2013, pp. 128-137.

Duquesnoy, "HLAMatchmaker: a molecularly based algorithm for histocompatibility determination. I. Description of the algorithm", Human Immunology, vol. 63, Issue 5, May 2002, pp. 339-352, doi.org/10.1016/S0198-8859(02)00382-8.

Durbin et al., "Platelet Extracellular Vesicles as a Therapeutic Agent in Hemorrhagic Shock", Oregon Health & Science University Department of Surgery, Division of Trauma, Sep. 20, 2023, 23 pages.

Eikelboom, et. al., "Combined antiplatelet and anticoagulant therapy clinical benefits and risks", Journal of Thrombosis and Haemostasis, vol. 5, Suppl 1, Jul. 2007, pp. 255-263, DOI: 10.1111/j.1538-7836.2007.02499.

Etchill, et. al., "Platelet Transfusion in Critical Care and Surgery: Evidence-Based Review of Contemporary Practice and Future Directions", Shock, vol. 47, No. 5, May 1, 2017, pp. 537-549.

Extended European Search Report in EP Appln. No. 05784165.2, date Mar. 26, 2008.

Extended European Search Report in EP Appln. No. 16808270.9, date Nov. 22, 2018.

Extended European Search Report in EP Appln. No. 16842662.5, date Jul. 26, 2019.

Extended European Search Report in EP Appln. No. 16923314.5, date Jun. 18, 2020.

Extended European Search Report in EP Appln. No. 17738796.6, date Jul. 23, 2019.

Extended European Search Report in EP Appln. No. 18856149.2, date May 26, 2021.

Extended European Search Report in EP Appln. No. 19840600.1 date Mar. 25, 2022.

Extended European Search Report in EP Appln. No. 19860896.0 date Jun. 14, 2023.

Extended European Search Report in EP Appln. No. 19888909.9 date Sep. 28, 2022.

Extended European Search Report in EP Appln. No. 19888994.1 date Nov. 7, 2022.

Extended European Search Report in EP Appln. No. 19891082.0 date Sep. 30, 2022.

Extended European Search Report in EP Appln. No. 20769409.2 date Dec. 6, 2022.

Extended European Search Report in EP Appln. No. 20802506.4 date Jan. 4, 2023.

Extended European Search Report in EP Appln. No. 20855485.7 date Sep. 15, 2023.

Extended European Search Report in EP Appln. No. 20855619.1 dated Sep. 15, 2023.

Extended European Search Report in EP Appln. No. 20894004.9 date Nov. 8, 2023.

Fijnheer et al., "Platelet activation during preparation of platelet concentrates: a comparison of the platelet-rich plasma and the buffv coat methods," Transfusion, 1990, 30(7):634-638.

Fischer et al., "Primary and secondary hemostatic functionalities of rehydrated, lyophilized platelets," 2006, Transfusion, 46:1943-1950.

Fischer et al., "The interaction of factor VIIa with rehydrated, lyophilized platelets", Platelets, vol. 19 (3), May 2008, pp. 182-191, DOI:10.1080/09537100701493794.

Fischer et. al., "Thrombus Formation with Rehydrated, Lyophilized Platelets", Hematology (Amsterdam, Netherlands), vol. 7 (6), Dec. 2002, pp. 359-369, DOI:10.1080/1024533021000047954.

Fitzpatrick et al., "A Novel Lyophilized Platelet Derivative Produces Effective Hemostasis in Uncontrolled Bleeding/Shock Model without Systemic Thrombosis", Blood, vol. 118, Issue 21, Nov. 18, 2011, pp. 719-722, doi.org/10.1182/blood.V118.21.719.719.

Fitzpatrick et al., "A Phase 1, Multi-Center, Open-Label, Dose Escalation Study of Thrombosomes in Bleeding Thrombocytopenia Patients in Three Cohorts", ClinicalTrials.gov ID NCT03394755, updated, Cellphire Therapeutics, Inc, Apr. 13, 2023, 34 pages.

Fitzpatrick et al., "A Phase 1, Multi-Center, Open-Label, Dose Escalation Study of Thrombosomes in Bleeding Thrombocytopenic Patients in Three Cohorts", ClinicalTrials.gov ID NCT03394755, Cellphire Therapeutics, Inc, Jan. 8, 2018, 6 pages.

Fitzpatrick et al., "A Phase 1, Multi-Center, Open-Label, Dose Escalation Study of Thrombosomes in Bleeding Thrombocytopenic Patients in Three Cohorts", Cellphire Therapeutics, Inc., NCT03394755, Statistical Analysis Plan, Jun. 2, 2020, 34 pages.

Fitzpatrick et al., "A Phase I, Multi-Center, Open-Label, Dose Escalation Study of Thrombosomes® in Bleeding Thrombocytopenic

(56) References Cited

OTHER PUBLICATIONS

Patients in Three Cohorts", Cellphire Therapeutics, Inc., NCT03394755, Study Protocol, Jun. 2, 2020, 55 pages.
Fitzpatrick et al., "A Prospective, Multicenter, Randomized, Open-Label, Phase 2, Parallel, Dose Ranging Multidose Study of Thrombosomes® vs Liquid Stored Platelets (LSP) in Bleeding Thrombocytopenic Patients", ClinicalTrials.gov NCT 04631211, Cellphire Therapeutics, Inc., Nov. 10, 2020, 8 pages.
Fitzpatrick et al., "A Prospective, Multicenter, Randomized, Open-Label, Phase 2, Parallel, Dose Ranging Multidose Study of Thrombosomes® vs Liquid Stored Platelets (LSP) in Bleeding Thrombocytopenic Patients", Cellphire Therapeutics, Inc., Clinical Study Protocol, NCT04631211, Mar. 28, 2024, 61 pages.
Fitzpatrick et al., "A Prospective, Multicenter, Randomized, Open-Lavel Phase 2, Parallel, Dose Ranging Multidose Study of Thrombosomes vs Liquid Stored Platelets (LSP) in Bleeding Thrombocytopenic Patients", ClinicalTrials.gov ID NCT04631211, Cellphire Therapeutics, Inc., Apr. 2, 2024, 44 pages.
International Search Report and Written Opinion in International Appln. No. PCT/US2018/050924, mailed Nov. 20, 2018, 18 pages.
International Search Report and Written Opinion in International Appln. No. PCT/US2019/043723, mailed Oct. 9, 2019, 16 pages.
International Search Report and Written Opinion in International Appln. No. PCT/US2019/050624, mailed Nov. 20, 2019, 23 pages.
International Search Report and Written Opinion in International Appln. No. PCT/US2019/063549, mailed Feb. 4, 2020, 10 pages.
International Search Report and Written Opinion in International Appln. No. PCT/US2019/063650, mailed Feb. 27, 2020, 11 pages.
International Search Report and Written Opinion in International Appln. No. PCT/US2019/063736, mailed Feb. 20, 2020, 10 pages.
International Search Report and Written Opinion in International Appln. No. PCT/US2019/063750, mailed Feb. 19, 2020, 10 pages.
International Search Report and Written Opinion in International Appln. No. PCT/US2020/022705, mailed Jul. 29, 2020, 12 pages.
International Search Report and Written Opinion in International Appln. No. PCT/US2020/031172, mailed Aug. 12, 2020, 8 pages.
International Search Report and Written Opinion in International Appln. No. PCT/US2020/042492, mailed Nov. 24, 2020, 9 pages.
International Search Report and Written Opinion in International Appln. No. PCT/US2020/046522, mailed Nov. 10, 2020, 9 Pages.
International Search Report and Written Opinion in International Appln. No. PCT/US2020/046525, mail date Nov. 10, 2020, 10 Pages.
International Search Report and Written Opinion in International Appln. No. PCT/US2020/049489, mail date Feb. 16, 2021, 7 Pages.
International Search Report and Written Opinion in International Appln. No. PCT/US2020/062214, mail date Mar. 17, 2021, 8 pages.
International Search Report and Written Opinion in International Appln. No. PCT/US2020/062216, mailed Feb. 9, 2021, 9 pages.
International Search Report and Written Opinion in International Appln. No. PCT/US2021/016360, mailed May 21, 2021, 13 pages.
International Search Report and Written Opinion in International Appln. No. PCT/US2021/016363, mailed May 18, 2021, 15 pages.
International Search Report and Written Opinion in International Appln. No. PCT/US2021/016389, mailed May 18, 2021, 15 pages.
International Search Report and Written Opinion in International Appln. No. PCT/US2021/016390, mailed May 18, 2021, 13 pages.
International Search Report and Written Opinion in International Appln. No. PCT/US2021/032783, mailed Aug. 24, 2021, 13 pages.
International Search Report and Written Opinion in International Appln. No. PCT/US2021/058814, mailed Mar. 17, 2022, 14 pages.
International Search Report and Written Opinion in International Appln. No. PCT/US2022/016866, mailed Jul. 4, 2022, 18 pages.
International Search Report and Written Opinion in International Appln. No. PCT/US2022/016883, mailed May 11, 2022, 10 pages.
International Search Report and Written Opinion in International Appln. No. PCT/US2023/066904, mailed Sep. 12, 2023, 12 pages.
International Search Report and Written Opinion in International Appln. No. PCT/US2023/066965, mailed Aug. 4, 2023, 10 pages.
International Search Report and Written Opinion in International Appln. No. PCT/US2024/027563, mailed Oct. 4, 2024, 15 pages.
International Search Report and Written Opinion in International Appln. No. PCT/US2024/031785, mailed Sep. 24, 2024, 12 pages.
International Search Report and Written Opinion in International Appln.No. PCT/US2024/019800, mailed Jul. 17, 2024, 16 pages.
Invitation to Pay Additional Fees in PCT Appln. No. PCT/US2020/022705, mailed May 18, 2020, 2 pages.
Ishler et al., "Lyophilized Human Platelets Interact with Fresh Platelets to Promote Hemostasis Under Shear In Vitro", Cellphire, Inc., 2021, 2 page, Abstract.
Ishler et al., "Lyophilized Human Platelets Interact with Fresh Platelets to Promote Hemostasis Under Shear In Vitro", Cellphire, Inc., Jul. 2021, 1 page, Poster PB0990.
Ishler et al., "Lyophilized Human Platelets Show Hemostatic Function Independent of von Willebrand Factor", Research and Practice in Thrombosis and Haemostasis, 2020; 4 (Suppl 1), 2 pages, ISth 2020 Virtual Congress Presentation, Jul. 2020, https://abstracts.isth.org/abstract/lyophilized-human-platelets-show-hemostatic-function-independent-of-von-willebrand-factor/., Abstract PB1533.
Ishler et al., "Lyophilized Platelets Show Hemostatic Function Independent of von Willebrand Factor", Cellphire, Inc., Department of Discovery and Research, ISth 2020 Virtual Congress, PB1533, Jul. 2020, 1 page, Poster.
Ishler et al., "StablePlate RX Canine Promotes in vitro Thromblin Generation and Thrombus Formation Under High Shear," Journal of Veterinary Internal Medicine, 2019 ACVIM Forum Research Abstract Program, p. 2483, Abstract.
Ishler et al., "StablePlate RX® Canine Promotes In Vitro Thrombin Generation and Thrombus Formation Under High Shear", Cellphire, Inc., 2019, 1 page, Poster 2.
Ishler et al., "StablePlate RX® Canine Promotes In Vitro Thrombin Generation and Thrombus Formation Under High Shear", Cellphire, Inc., 2019, 1 page, Poster 1.
Ito et al., "Total Thrombus-formation Analysis System (T-TAS) can predict periprocedural bleeding events in patients undergoing catheter ablation for atrial fibrillation," Journal of American Heart Association, 2015, 5(1):e002744, 12 pages.
Jennings et al., "Antiplatelet and anticoagulant agents: Key differences in mechanisms of action, clinical application, and therapeutic benefit in patients with non-ST-segment-elevation acute coronary syndromes", Current Opinion in Cardiology vol. 23, No. 4, Jul. 2008, pp. 302-308, DOI: 10.1097/HCO.0b013e3283021ad9.
Jennings et al., "The pharmacodynamics of parenteral glycoprotein IIb/IIIa inhibitors", Journal of Interventional Cardiology, vol. 15, No. 1, Feb. 2002, pp. 45-60, DOI: 10.1111/j.1540-8183.2002.tb01034.x.
Johnson et al.,"Platelet microparticles in cryopreserved platelets: Potential mediators of hemostasis", Transfusion and Apheresis Science, vol. 53, Issue 2, Oct. 2015, pp. 146-152, doi.org/10.1016/j.transci.2015.10.011.
Joshi et al., "Lyophilised Reconstituted Human Platelets Increase Thrombus Formation in a Clinical Ex Vivo Model of Deep Arterial Injury", Thrombosis and Haemostasis, vol. 108, No. 1, 2012, pp. 176-182, DOI: 10.1160/TH12-02-0059.
Joshi et al., "Thrombosomes Show Dose-Dependent Increase in Thrombus Formation in a Model of Deep Arterial Injury", Blood, vol. 118, Issue 21, Nov. 18, 2011, 8 pages, doi.org/10.1182/blood.V118.21.2319.2319, Abstract 2319.
Kariko et al., "Phosphate-enhanced transfection of cationic lipid-complexed mRNA and plasmid DNA," Biochim. Biophys. Acta, 1998, 1369(2):320-334.
Kerrigan et al., "Molecular basis for *Staphylococcus aureus* mediated platelet aggregate formation under arterial shear in vitro," Arteriosclerosis Thrombosis and Vascular Biology, 2008, 28(2):334-340.
Kerrigan, "Platelet interactions with bacteria," The non-thrombotic role of platelets in health and disease; Chapter 4, 2015, 65-84.
Kessler, "Bleeding after treatment with rivaroxaban or apixaban", Clinical Advances in Hemotology and Oncology, vol. 17, No. 9, Supplement 15, Sep. 2019, pp. 3-19.

(56) References Cited

OTHER PUBLICATIONS

Kirby et al., "Preparation of liposomes containing Factor VIII for oral treatment of haemophilia," 1984, J. Microencapsul. 1(1): 33-45.

Kirkley et al., "Use of single donor platelets", Blood Reviews, vol. 8, Issue 3, Sep. 1994, pp. 142-147, doi.org/10.1016/0268-960X(94)90074-R.

Kishbaugh et al., "Intervening with Platelet Therapies", National Elephant Herpesvirus Laboratory at the National Zoo, vol. 4, No. 2, 2017, 4 pages.

Kreuger et al., "HLA-matched platelet transfusions are effective only in refractory patients with positive HLA antibody screening", Transfusion, The Journal of American Association of Blood Banks, vol. 59, No. 11, Oct. 11, 2019, pp. 3303-3307, doi.org/10.1111/trf.15530.

Fitzpatrick et al., "Freeze-dried platelets: Advancing towards clinical use", Cryobiology, vol. 67, Issue 3, Dec. 2013, p. 420, doi.org/10.1016/j.cryobiol.2013.09.086, Abstract.

Fitzpatrick et al., "Stabilization and preservation of a platelet derived hemostatic agent, Thrombosomes", Cryobiology, vol. 63, Issue 3, Dec. 2011, p. 306, Abstract, doi:10.1016/j.cryobiol.2011.09.005.

Fitzpatrick, "Novel platelet products under development for the treatment of thrombocytopenia or acute hemorrhage", Transfusion and Apheresis Science, vol. 58, Issue 1, Feb. 2019, pp. 7-11, doi: 10.1016/j.transci.2018.12.010.

Gaertner et al., "Migrating platelets are mechano-scavengers that collect and bundle bacteria," Cell, Nov. 30, 2017, 171(6):1368-1382.

Gao et al., "Development of Optimal Techniques for Cryopreservation of Human Platelets: I. Platelet activation during cold storage (at 22 and 8° C.) and cryopreservation", Cryobiology vol. 38(3), May 1999, pp. 225-235, DOI: 10.1006/cryo.1999.2162.

Ghaithi et al., "Evaluation of the Total Thrombus-Formation System (T-TAS): application to human and mouse blood analysis", Platelets, vol. 30, Issue 7, 2019, pp. 893-900, doi: 10.1080/09537104.2018.1535704.

Gilbert et al., "Platelet-derived microparticles express high affinity receptors for factor VIII.", I.Biol.Chem., 1991, 266:17261-17268.

Giles et al., "A combination of factor Xa and phosphatidylcholine-phosphatidylserine vesicles bypasses factor VIII in vivo", Br. J., Haematol., 1988, 69(4):491-497.

Godier et al., "Management of antiplatelet therapy for non elective invasive procedures of bleeding complications: proposals from the French working group on perioperative haemostasis (GIHP), in collaboration with the French Society of Anaesthesia and Intensive Care Medicine (SFAR)" Anaesthesia, Critical Care and Pain Medicine, vol. 38, Issue 3, Jun. 2019, pp. 289-302, doi: 10.1016/j.accpm.2018.10.004.

Goggs, et. al., "Lyophilized Platelets Versus Cryopreserved Platelets for Management of Bleeding in Thrombocytopenic Dogs: A Multicenter Randomized Clinical Trial", Journal of Veterinary Internal Medicine, Nov. 2020, vol. 34, Issue 6, pp. 2384-2397, doi: 10.1111/jvim.15922.

Greene, et. al., "Chapter 9: Component Preparation and Manufacturing", Transfusion Medicine and Hemostasis, Elsevier Science, 1st edition, 2009, pp. 45-50, doi:10.1016/B978-0-12-374432-6.00009-9, XP009527060.

Grosset et al., "Rapid presymptomatic detection of PrPSc via conformationally responsive palindromic PrP peptides", Peptides, vol. 26, Issue 11, Nov. 2005, pp. 2193-2200, doi: 10.1016/j.peptides.2005.03.006.

Gybel-Brask et al., "Freeze-dried platelets (Thrombosomes®) reverses CPB-induced platelet dysfunction ex-vivo", RegionH, Rigshospitalet, The Center of Diagnostic Investigations, 2023, 1 page, poster.

Hagedorn, et. al., "Factor XIIa Inhibitor Recombinant Human Albumin Infestin-4 Abolishes Occlusive Arterial Thrombus Formation Without Affecting Bleeding", Circulation, vol. 121, Issue 13, Apr. 6, 2010, pp. 1510-1517, DOI: 10.1161/Circulationaha.109.924761.

Hale et al., "A Novel Use of the NOD SCID Mouse Model for Hemostatic Efficacy", Cellphire, Inc., 2019, 1 page.

Healthline.com [online], "How Many Cells Are in the Human Body? Fast Facts," Jul. 18, 2018, retrieved on May 17, 2021, retrieved from URL, 11 pages.

Heitmeier et al., "Pharmacological profile of asundexian, a novel, orally bioavailable inhibitor of factor XIa", Journal of Thrombosis and Haemostasis, vol. 20, No. 6, Jun. 2022, pp. 1400-1411, https://doi.org/10.1111/jth.15700.

Heitz et al., "Twenty years of cell-penetrating peptides: from molecular mechanisms to therapeutics," British Journal of Pharmacology, 2009, 157:195-206.

helena.com [online], "Ristocetin Cofactor Assay," retrieved on Feb. 18, 2021, retrieved from URL , 2 pages.

Hemker et al., "Calibrated automated thrombin generation measurement in clotting plasma," Pathophvsiol. Haemost. Thromb., 2003, 33:4-15.

Hoffman et al., "Coagulation Factor IXa Binding to Activated Platelets and Platelet-Derived Microparticles: A Flow Cytometric Study," Thromb. Haemost., 1992, 68:74-78.

Holcomb et al., "Optimal fluid therapy for traumatic hemorrhagic shock," Crit. Care Clin., 2017, 33(1):15-36.

Holme et al., "Platelet-derived microvesicles and activated platelets express factor Xa activity," Blood Coae:ul. Fibrinolysis, 1995, 6:302-310.

Holmes et. al., "Combining Antiplatelet and Anticoagulant Therapies", Journal of the American College of Cardiology, vol. 54, No. 2, Jul. 7, 2009, pp. 95-109.

Homepage.haemonetics.com [online], "TEG® 5000 Thrombelastograph® Hemostasis Analyzer System," retrieved Feb. 18, 2021, retrieved from 5000>, 3 pagesURL.

Hong et al., "Transfection of human platelets with short interfering RNA", Clinical and Translational Science, vol. 4, Issue 5, Jun. 2011, pp. 180-182, doi: 10.1111/j.1752-8062.2011.00279.x.

Hrachovinova et al., "Interaction of P-selectin and PSGL-1 generates microparticles that correct hemostasis in a mouse model of hemophilia A," Nat Med., 2003, 9(8): 1020-1025.

Huebner et al., "Freeze-dried plasma enhances clot formation and inhibits fibrinolysis in the presence of tissue plasminogen activator similar to pooled liquid plasma", Transfusion, vol. 57, Issue 8, Aug. 2017, pp. 2007-2015, DOI:10.1111/trf.14149.

Inaba et al., "Dried platelets in a swine model of liver injury", Shock, vol. 41, Issue 5, May 2014, pp. 429-434, doi: 10.1097/SHK.0000000000000141.

International Partial Search Report and Provisional Opinion in International Appln No. PCT/US2022/079280, mailed Feb. 20, 2023, 14 pages.

International Partial Search Report in International Appln No. PCT/US2022/016866, mailed May 11, 2022, 13 pages.

International Preliminary Report on Patentability in International Appln. No. PCT/US2005/028559, dated May 8, 2007,5 pages.

International Preliminary Report on Patentability in International Appln. No. PCT/US2016/036657, mailed Dec. 12, 2017, 6 pages.

International Preliminary Report on Patentability in International Appln. No. PCT/US2016/048846, mailed Mar. 6, 2018, 5 pages.

International Preliminary Report on Patentability in International Appln. No. PCT/US2016/065681, dated Jun. 11, 2019, 7 pages.

International Preliminary Report on Patentability in International Appln. No. PCT/US2017/012836, dated Jul. 17, 2018, 7 pages.

International Preliminary Report on Patentability in International Appln. No. PCT/US2018/050924, dated Mar. 26, 2020, 17 pages.

International Preliminary Report on Patentability in International Appln. No. PCT/US2019/043723, dated Feb. 11, 2021, 14 pages.

International Preliminary Report on Patentability in International Appln. No. PCT/US2019/050624, dated Mar. 25, 2021, 10 pages.

International Preliminary Report on Patentability in International Appln. No. PCT/US2019/063549, mailed Jun. 10, 2021, 9 pages.

International Preliminary Report on Patentability in International Appln. No. PCT/US2019/063650, mailed Jun. 10, 2021, 9 pages.

International Preliminary Report on Patentability in International Appln. No. PCT/US2019/063736, mailed Jun. 10, 2021, 8 pages.

International Preliminary Report on Patentability in International Appln. No. PCT/US2019/063750, mailed Jun. 10, 2021, 8 pages.

(56) References Cited

OTHER PUBLICATIONS

International Search Report and Written Opinion in International Appln No. PCT/US2022/079280, mailed date Apr. 21, 2023, 27 pages.
International Search Report and Written Opinion in International Appln. No. PCT/US2005/028559, mailed Mar. 23, 2007, 8 pages.
International Search Report and Written Opinion in International Appln. No. PCT/US2015/060553, mailed Jan. 28, 2016, 7 pages.
International Search Report and Written opinion in International Appln. No. PCT/US2016/036657, mailed Aug. 29, 2016, 7 pages.
International Search Report and Written Opinion in International Appln. No. PCT/US2016/048846, mailed Nov. 16, 2016, 2 pages.
International Search Report and Written Opinion in International Appln. No. PCT/US2016/065681, mailed Feb. 17, 2017, 2 pages.
International Search Report and Written Opinion in International Appln. No. PCT/US2017/012836, mailed Apr. 7, 2017, 8 pages.

* cited by examiner

PLATELETS AS DELIVERY AGENTS

CROSS-REFERENCE TO RELATED APPLICATIONS

This application is a Continuation of U.S. patent application Ser. No. 16/697,401, filed on Nov. 27, 2019; U.S. patent application Ser. No. 16/697,401 claims priority to U.S. Provisional Patent Application No. 62/773,931, filed on Nov. 30, 2018, U.S. Provisional Patent Application No. 62/775,141, filed on Dec. 4, 2018, and U.S. Provisional Patent Application No. 62/828,043, filed on Apr. 2, 2019. The contents of each of these applications are incorporated herein by reference in their entireties.

TECHNICAL FIELD

Provided herein are compositions and methods for use of platelets, platelet derivatives, or thrombosomes (e.g., freeze-dried platelet derivatives) as biological carriers of cargo, such as RNA agents, also referred to herein as RNA agent-loaded platelets, platelet derivatives, or thrombosomes. Also provided herein are methods of preparing platelets, platelet derivatives, or thrombosomes loaded with the RNA agent of interest.

RNA agent-loaded platelets described herein can be stored under typical ambient conditions, refrigerated, cryopreserved, for example with dimethyl sulfoxide (DMSO), and/or lyophilized after stabilization (e.g., to form thrombosomes).

DESCRIPTION OF RELATED ART

Blood is a complex mixture of numerous components. In general, blood can be described as comprising four main parts: red blood cells, white blood cells, platelets, and plasma. The first three are cellular or cell-like components, whereas the fourth (plasma) is a liquid component comprising a wide and variable mixture of salts, proteins, and other factors necessary for numerous bodily functions. The components of blood can be separated from each other by various methods. In general, differential centrifugation is most commonly used currently to separate the different components of blood based on size and, in some applications, density.

Unactivated platelets, which are also commonly referred to as thrombocytes, are small, often irregularly-shaped (e.g., discoidal or ovoidal) megakaryocyte-derived components of blood that are involved in the clotting process. They aid in protecting the body from excessive blood loss due not only to trauma or injury, but to normal physiological activity as well. Platelets are considered crucial in normal hemostasis, providing the first line of defense against blood escaping from injured blood vessels. Platelets generally function by adhering to the lining of broken blood vessels, in the process becoming activated, changing to an amorphous shape, and interacting with components of the clotting system that are present in plasma or are released by the platelets themselves or other components of the blood. Purified platelets have found use in treating subjects with low platelet count (thrombocytopenia) and abnormal platelet function (thrombasthenia). Concentrated platelets are often used to control bleeding after injury or during acquired platelet function defects or deficiencies, for example those occurring during surgery and those due to the presence of platelet inhibitors.

Loading platelets with RNA agents may allow targeted delivery of the RNA agents to sites of interest. Further, RNA agent-loaded platelets may be lyophilized or cryopreserved to allow for long-term storage. In some embodiments, the loading of a RNA agent in the platelets mitigates systemic side effects associated with the RNA agent and lowers the threshold of therapeutic dose necessary by facilitating targeted treatment at site of interest. Hong et al. in www.ncbi.nlm.nih.gov/pmc/articles/PMC3125693/pdf/CTS-4-180.pdf have described short interfering RNA (siRNA)-loaded platelets.

SUMMARY OF THE INVENTION

In some embodiments, provided herein are methods of preparing RNA agent-loaded platelets, RNA agent-loaded platelet derivatives, or RNA agent-loaded thrombosomes (e.g., freeze-dried platelet derivatives), comprising: treating platelets, platelet derivatives, or thrombosomes with a RNA agent, a cationic transfection reagent and at least one loading agent and optionally one or more plasticizers such as organic solvents, such as organic solvents selected from the group consisting of ethanol, acetic acid, acetone, acetonitrile, dimethylformamide, dimethyl sulfoxide, dioxane, methanol, n-propanol, isopropanol, tetrahydrofuran (THF), N-methyl pyrrolidone, dimethylacetamide (DMAC), or combinations thereof, to form the RNA agent-loaded platelets, RNA agent-loaded platelet derivatives, or RNA agent-loaded thrombosomes.

In some embodiments, the methods of preparing RNA agent-loaded platelets can include treating the platelets, the platelet derivatives, and/or the thrombosomes with the RNA agent and with one loading agent. In some embodiments, the methods of preparing RNA agent-loaded platelets, RNA agent-loaded platelet derivatives, or RNA agent-loaded thrombosomes can include treating the platelets, the platelet derivatives, or the thrombosomes with the RNA agent and with multiple loading agents.

In some embodiments, suitable organic solvents include, but are not limited to alcohols, esters, ketones, ethers, halogenated solvents, hydrocarbons, nitriles, glycols, alkyl nitrates, water or mixtures thereof. In some embodiments, suitable organic solvents include, but are not limited to methanol, ethanol, n-propanol, isopropanol, acetic acid, acetone, methyl ethyl ketone, methyl isobutyl ketone, methyl acetate, ethyl acetate, isopropyl acetate, tetrahydrofuran, isopropyl ether (IPE), tert-butyl methyl ether, dioxane (e.g., 1,4-dioxane), acetonitrile, propionitrile, methylene chloride, chloroform, toluene, anisole, cyclohexane, hexane, heptane, ethylene glycol, nitromethane, dimethylformamide, dimethyl sulfoxide, N-methyl pyrrolidone, dimethylacetamide, and combinations thereof. The presence of organic solvents, such as ethanol, can be beneficial in the processing of platelets, platelet derivatives, and/or thrombosomes. In some embodiments, the organic solvent may open up and/or increase the flexibility of the plasma membrane of the platelets, platelet derivatives, and/or thrombosomes. In some embodiments, the organic solvent can aid in solubilizing molecules to be loaded.

In some embodiments, provided herein is a method of preparing RNA agent-loaded platelets, RNA agent-loaded platelet derivatives, or RNA agent-loaded thrombosomes, comprising: treating platelets, platelet derivatives, or thrombosomes with a RNA agent, a cationic transfection reagent and a loading buffer comprising a base, a loading agent, and optionally at least one organic solvent such as an organic solvent selected from the group consisting of ethanol, acetic acid, acetone, acetonitrile, dimethylformamide, dimethyl sulfoxide, dioxane, methanol, n-propanol, isopropanol, tetrahydrofuran (THF), N-methyl pyrrolidone, dimethylacetamide (DMAC), or combinations thereof, to form the RNA agent-loaded platelets, the RNA agent-loaded platelet derivatives, or the RNA agent-loaded thrombosomes.

In some embodiments, provided herein is a method of preparing RNA agent-loaded platelets, RNA agent-loaded platelet derivatives, or RNA agent-loaded thrombosomes, comprising: treating platelets, platelet derivatives, or thrombosomes with a RNA agent, a cationic transfection reagent and a loading buffer comprising a salt, a base, a loading agent, and optionally at least one organic solvent to form the RNA agent-loaded platelets, RNA agent-loaded platelet derivatives, or the RNA agent-loaded thrombosomes.

In some embodiments, provided herein is a method of preparing RNA agent-loaded platelets, RNA agent-loaded platelet derivatives, or RNA agent-loaded thrombosomes, comprising: treating platelets, platelet derivatives, or thrombosomes with a RNA agent and with a loading agent and optionally at least one organic solvent to form the RNA agent-loaded platelets, the RNA agent-loaded platelet derivatives, or the RNA agent-loaded thrombosomes.

In some embodiments, provided herein is a method of preparing RNA agent-loaded platelets, RNA agent-loaded platelet derivatives, or RNA agent-loaded thrombosomes, comprising: treating platelets, platelet derivatives, or thrombosomes with a RNA agent, a cationic transfection reagent, and a loading buffer comprising a base, a loading agent, and optionally at least one organic solvent to form the RNA agent-loaded platelets, the RNA agent-loaded platelet derivatives, or the RNA agent-loaded thrombosomes.

In some embodiments, provided herein is a method of preparing RNA agent-loaded platelets, RNA agent-loaded platelet derivatives, or RNA agent-loaded thrombosomes, comprising: treating platelets, platelet derivatives, or thrombosomes with a RNA agent, a cationic transfection reagent, and a loading buffer comprising a salt, a base, a loading agent, and optionally at least one organic solvent to form the RNA agent-loaded platelets, the RNA agent-loaded platelet derivatives, or the RNA agent-loaded thrombosomes.

In some embodiments, provided herein is a method of preparing RNA agent-loaded platelets, RNA agent-loaded platelet derivatives, or RNA agent-loaded thrombosomes, comprising: step (a) providing platelets, platelet derivatives, or thrombosomes; and step (b) treating the platelets, the platelet derivatives, or the thrombosomes with a RNA agent, a cationic transfection reagent, and a loading buffer comprising a salt, a base, a loading agent, and optionally at least one organic solvent to form the RNA agent-loaded platelets, RNA agent-loaded platelet derivatives, or the RNA agent-loaded thrombosomes. In some embodiments, the methods further include cryopreserving the RNA agent-loaded platelets, RNA agent-loaded platelet derivatives, or the RNA agent-loaded thrombosomes. In some embodiments, the methods further include cold storing the RNA agent-loaded platelets, RNA agent-loaded platelet derivatives, or the RNA agent-loaded thrombosomes. In some embodiments, the methods further include drying the RNA agent-loaded platelets or the RNA agent-loaded platelet derivatives. In some embodiments, the methods further include freeze-drying the RNA agent-loaded platelets or the RNA agent-loaded platelet derivatives. In such embodiments, the methods may further include rehydrating the RNA agent-loaded platelets, RNA agent-loaded platelet derivatives, or RNA agent-loaded thrombosomes obtained from the drying step. In some embodiments, the methods that further include drying the RNA agent-loaded platelets or RNA agent-loaded platelet derivatives and rehydrating the RNA agent-loaded platelets or the RNA agent-loaded platelet derivatives obtained from the drying step provides rehydrated platelets or platelet derivatives comprising at least 10% of the amount of the RNA agent of step (b). In some embodiments, the methods that further include drying the RNA agent-loaded platelets or the RNA agent-loaded platelet derivatives and rehydrating the RNA agent-loaded platelets or the RNA agent-loaded platelet derivatives obtained from the drying step provides rehydrated platelets or platelet derivatives comprising from about 0.1 nM to about 10 µM, such as about 1 nM to about 1 µM, such as about 10 nM to 10 µM, such as about 100 nM of the RNA agent.

In some embodiments, the platelets, platelet derivatives, or thrombosomes are treated with the RNA agent and with the buffer sequentially, in either order.

In some embodiments, provided herein is a method of preparing RNA agent-loaded platelets, RNA agent-loaded platelet derivatives, or RNA agent-loaded thrombosomes, comprising: step (1) treating platelets, platelet derivatives, or thrombosomes with a RNA agent to form a first composition; and step (2) treating the first composition with a buffer comprising a salt, a base, a loading agent, and optionally at least one organic solvent to form the RNA agent-loaded platelets, RNA agent-loaded platelet derivatives, or RNA agent-loaded thrombosomes. In some embodiments, the methods further include treating the first composition with a cationic transfection reagent to form a second composition. In some embodiments, the second composition is treated with a buffer comprising a salt, a base, a loading agent, and optionally at least one organic solvent to form the RNA agent-loaded platelets, RNA agent-loaded platelet derivatives, or RNA agent-loaded thrombosomes. In some embodiments, the first composition is treated with a cationic transfection agent prior to the treating step (2). In some embodiments, the first composition is treated with a cationic transfection agent during the treating step (2). In some embodiments, the first composition is treated with a cationic transfection agent both prior to and during the treating step (2). In some embodiments, the methods further include drying the RNA agent-loaded platelets or the RNA agent-loaded platelet derivatives obtained in step (2). In some embodiments, the methods further include cryopreserving, lyopreserving (e.g., freeze-drying) the RNA agent-loaded platelets or the RNA agent-loaded platelet derivatives. In some embodiments, the methods further include cold storing the RNA agent-loaded platelets, the RNA agent-loaded platelet derivatives, the RNA agent-loaded thrombosomes, or compositions containing RNA agent-loaded platelets at suitable storage temperatures, such as standard room temperature storing (e.g., storing at a temperature ranging from about 20 to about 30° C.) or cold storing (e.g., storing at a temperature ranging from about 1 to about 10° C.). In some embodiments, the methods further include cryopreserving, freeze-drying, thawing, rehydrating, and combinations thereof, the RNA agent loaded platelets, the RNA agent-loaded platelet derivatives, or the RNA agent-loaded thrombosomes. For example, in such embodiments, the methods may further include rehydrating the RNA agent-loaded platelets, the RNA agent-loaded platelet derivatives, or the RNA agent-loaded thrombosomes obtained from the drying step. In some embodiments, the methods that further include drying the RNA agent-loaded platelets or RNA agent-loaded platelet derivatives and rehydrating the RNA agent-loaded platelets or the RNA agent-loaded platelet derivatives obtained from the drying step provides rehydrated platelets or platelet derivatives comprising at least 10% of the amount of the RNA agent of step (1). In some embodiments, the methods that further include drying the RNA agent-loaded platelets or the RNA agent-loaded platelet derivatives and rehydrating the RNA agent-loaded platelets or the RNA agent-loaded platelet derivatives obtained from the drying step provides rehydrated platelets or platelet derivatives comprising from about 0.1 nM to about 10 µM, such as about 1 nM to about 1 µM, such as about 10 nM to 10 µM, such as about 100 nM of the RNA agent of step (1).

In some embodiments provided herein is a method of preparing RNA agent-loaded platelets, RNA agent-loaded platelet derivatives, or RNA agent-loaded thrombosomes, comprising: step (1) treating the platelets, platelet derivatives, or thrombosomes with a buffer comprising a salt, a base, a loading agent, and optionally ethanol, to form a first composition; and step (2) treating the first composition with a RNA agent, to form the RNA agent-loaded platelets, the RNA agent-loaded platelet derivatives, or the RNA agent-loaded thrombosomes. In some embodiments, the methods further include treating the first composition with a cationic transfection reagent to form a second composition. In some embodiments, the second composition is treated with a buffer comprising a salt, a base, a loading agent, and optionally at least one organic solvent to form the RNA agent-loaded platelets, RNA agent-loaded platelet derivatives, or RNA agent-loaded thrombosomes. In some embodiments, the first composition is treated with a cationic transfection agent prior to the treating step (2). In some embodiments, the first composition is treated with a cationic transfection agent during the treating step (2). In some embodiments, the first composition is treated with a cationic transfection agent both prior to and during the treating step (2). In some embodiments, the methods further include drying the RNA agent-loaded platelets, the RNA agent-loaded platelet derivatives, or the RNA agent-loaded thrombosomes obtained in step (2). In some embodiments, the methods further include freeze-drying the RNA agent-loaded platelets or the RNA agent-loaded platelet derivatives. In such embodiments, the methods may further include rehydrating the RNA agent-loaded platelets or the RNA agent-loaded platelet derivatives obtained from the drying step. In some embodiments, the methods that further include drying the RNA agent-loaded platelets or the RNA agent-loaded platelet derivatives and rehydrating the RNA agent-loaded platelets or the RNA agent-loaded platelet derivatives obtained from the drying step provides rehydrated platelets or platelet derivatives comprising at least 10% of the amount of the RNA agent of step (2). In some embodiments, the methods that further include drying the RNA agent-loaded platelets or the RNA agent-loaded platelet derivatives and rehydrating the RNA agent-loaded platelets or the RNA agent-loaded platelet derivatives obtained from the drying step provides rehydrated platelets or thrombosomes comprising from about 0.1 nM to about 10 µM, such as about 1 nM to about 1 µM, such as about 10 nM to 10 µM, such as about 100 nM of the RNA agent of step (2).

In some embodiments, the platelets or thrombosomes are treated with the RNA agent and with the buffer concurrently.

Thus, in some embodiments provided herein is a method of preparing RNA agent-loaded platelets, the RNA agent-loaded platelet derivatives, or the RNA agent-loaded thrombosomes, comprising: treating the platelets, the platelet derivatives, or the thrombosomes with a RNA agent and a cationic transfection reagent in the presence of a buffer comprising a salt, a base, a loading agent, and optionally ethanol, to form the RNA agent-loaded platelets, the RNA agent-loaded platelet derivatives, or the RNA agent-loaded thrombosomes.

In some embodiments, the methods further include drying the RNA agent-loaded platelets or the RNA agent-loaded platelet derivatives. In some embodiments, the methods further include freeze-drying the RNA agent-loaded platelets or the RNA agent-loaded platelet derivatives. In such embodiments, the methods further include rehydrating the RNA agent-loaded platelets or the RNA agent-loaded platelet derivatives obtained from the drying step.

In some embodiments, the methods that further include drying the RNA agent-loaded platelets or the RNA agent-loaded platelet derivatives and rehydrating the RNA agent-loaded platelets or the RNA agent-loaded platelet derivatives obtained from the drying step provides rehydrated platelets or the thrombosomes comprising at least 10% of the amount of the RNA agent prior to loading.

In some embodiments, the methods that further include drying the RNA agent-loaded platelets or the RNA agent-loaded platelet derivatives and rehydrating the RNA agent-loaded platelets or the RNA agent-loaded platelet derivatives obtained from the drying step provides rehydrated platelets or thrombosomes comprising from about 0.1 nM to about 10 µM, such as about 1 nM to about 1 µM, such as about 10 nM to 10 µM, such as about 100 nM of the RNA agent.

In some embodiments of the methods of preparing cargo-loaded platelets, such as RNA agent-loaded platelets, as provided herein, the methods do not comprise treating platelets, platelet derivatives, or thrombosomes with ethanol.

In some embodiments of the methods of preparing cargo-loaded platelets, such as RNA agent-loaded platelets, as provided herein, the methods do not comprise treating platelets, platelet derivatives, or thrombosomes with a solvent selected from the group consisting of ethanol, acetic acid, acetone, acetonitrile, dimethylformamide, dimethyl sulfoxide, dioxane, methanol, n-propanol, isopropanol, tetrahydrofuran (THF), N-methyl pyrrolidone, dimethylacetamide (DMAC), or combinations thereof.

In some embodiments of the methods of preparing cargo-loaded platelets, such as RNA agent-loaded platelets, as provided herein, the methods do not comprise treating platelets, platelet derivatives, or thrombosomes with an organic solvent.

In some embodiments of the methods of preparing cargo-loaded platelets, such as RNA agent-loaded platelets, as provided herein, the methods do not comprise treating platelets, platelet derivatives, or thrombosomes with a solvent.

In some embodiments of the methods of preparing cargo-loaded platelets, such as RNA agent-loaded platelets, as provided herein, the methods comprise treating platelets, platelet derivatives, or thrombosomes with a solvent, such as an organic solvent, such as organic solvent selected from the group consisting of ethanol, acetic acid, acetone, acetonitrile, dimethylformamide, dimethyl sulfoxide, dioxane, methanol, n-propanol, isopropanol, tetrahydrofuran (THF), N-methyl pyrrolidone, dimethylacetamide (DMAC), or combinations thereof, such as ethanol.

In some embodiments, platelets, platelet derivatives, or thrombosomes are pooled from a plurality of donors. Such platelets, platelet derivatives, and thrombosomes pooled from a plurality of donors may be also referred herein to as pooled platelets, platelet derivatives, or thrombosomes. In some embodiments, the donors are more than 5, such as more than 10, such as more than 20, such as more than 50, such as up to about 100 donors. In some embodiments, the donors are from about 5 to about 100, such as from about 10 to about 50, such as from about 20 to about 40, such as from about 25 to about 35.

Thus, provided herein in some embodiments is a method of preparing RNA agent-loaded platelets, RNA agent-loaded platelet derivatives, or RNA agent-loaded thrombosomes comprising: step (A) pooling platelets, platelet derivatives, or thrombosomes from a plurality of donors; and step (B) treating the platelets, platelet derivatives, or thrombosomes from step (A) with a RNA agent, a cationic transfection reagent, and with a loading buffer comprising a salt, a base, a loading agent, and optionally ethanol, to form the RNA agent-loaded platelets, the RNA agent-loaded platelet derivatives, or the RNA agent-loaded thrombosomes. In some embodiments, the methods further include drying the RNA agent-loaded platelets or the RNA agent-loaded platelet derivatives obtained in step (B). In some embodiments, the methods further include freeze-drying the RNA agent-loaded platelets or the RNA agent-loaded platelet derivatives. In such embodiments, the methods may further include rehydrating the RNA agent-loaded platelets or the RNA agent-loaded platelet derivatives obtained from the drying step. In some embodiments, the methods that further include drying the RNA agent-loaded platelets or the RNA agent-loaded platelet derivatives and rehydrating the RNA agent-loaded platelets or the RNA agent-loaded platelet derivatives obtained from the drying step provides rehydrated platelets or rehydrated platelet derivatives comprising at least 10% of the amount of the RNA agent of step (B). In some embodiments, the methods that further include drying the RNA agent-loaded platelets or the RNA agent-loaded platelet derivatives and rehydrating the RNA agent-loaded platelets or the RNA agent-loaded platelet derivatives obtained from the drying step provides rehydrated platelets or rehydrated platelet derivatives comprising from about 0.1 nM to about 10 µM, such as about 1 nM to about 1 µM, such as about 10 nM to 10 µM, such as about 100 nM of the RNA agent of step (B).

In some embodiments, the pooled platelets, platelet derivatives, or thrombosomes are treated with the RNA agent and with the buffer sequentially, in either order.

Thus, provided herein in some embodiments is a method of preparing RNA agent-loaded platelets, RNA agent-loaded platelet derivatives, or RNA agent-loaded thrombosomes comprising: step (A) pooling platelets, platelet derivatives, or thrombosomes from a plurality of donors; and step (B) (1) treating the platelets, platelet derivatives, or thrombosomes from step (A) with a RNA agent to form a first composition; and step (B) (2) treating the first composition with a buffer comprising a salt, a base, a loading agent, and optionally ethanol, to form the RNA agent-loaded platelets, RNA agent-loaded platelet derivatives, or RNA agent-loaded thrombosomes. In some embodiments, the methods further include treating the first composition with a cationic transfection reagent to form a second composition. In some embodiments, the second composition is treated with a buffer comprising a salt, a base, a loading agent, and optionally at least one organic solvent to form the RNA agent-loaded platelets, RNA agent-loaded platelet derivatives, or RNA agent-loaded thrombosomes. In some embodiments, the first composition is treated with a cationic transfection agent prior to the treating step (B) (2). In some embodiments, the first composition is treated with a cationic transfection agent during the treating step (B) (2). In some embodiments, the first composition is treated with a cationic transfection agent both prior to and during the treating step (B) (2). In some embodiments, the methods further include drying the RNA agent-loaded platelets or the RNA agent-loaded platelet derivatives obtained in step (B) (2). In some embodiments, the methods further include freeze-drying the RNA agent-loaded platelets or the RNA agent-loaded platelet derivatives. In such embodiments, the methods may further include rehydrating the RNA agent-loaded platelets or the RNA agent-loaded platelet derivatives obtained from the drying step. In some embodiments, the methods that further include drying the RNA agent-loaded platelets or the RNA agent-loaded platelet derivatives and rehydrating the RNA agent-loaded platelets or the RNA agent-loaded platelet derivatives obtained from the drying step provides rehydrated platelets or rehydrated platelet derivatives comprising at least 10% of the amount of the RNA agent of step (B) (1). In some embodiments, the methods that further include drying the RNA agent-loaded platelets or the RNA agent-loaded platelet derivatives and rehydrating the RNA agent-loaded platelets or the RNA agent-loaded platelet derivatives obtained from the drying step provides rehydrated platelets or platelet derivatives comprising from about 0.1 nM to about 10 µM, such as about 1 nM to about 1 µM, such as about 10 nM to 10 µM, such as about 100 nM of the RNA agent of step (B) (1).

Thus, provided herein in some embodiments is a method of preparing RNA agent-loaded platelets, RNA agent-loaded platelet derivatives, or RNA agent-loaded thrombosomes comprising: step (A) pooling platelets, platelet derivatives, or thrombosomes from a plurality of donors; and (B) (1) treating the platelets, the platelet derivatives, or the thrombosomes from step (A) with a buffer comprising a salt, a base, a loading agent, and optionally ethanol, to form a first composition; and (B) (2) treating the first composition with a RNA agent to form the RNA agent-loaded platelets, the RNA agent-loaded platelet derivatives, or the RNA agent-loaded thrombosomes. In some embodiments, the methods further include treating the first composition with a cationic transfection reagent to form a second composition. In some embodiments, the second composition is treated with a buffer comprising a salt, a base, a loading agent, and optionally at least one organic solvent to form the RNA agent-loaded platelets, RNA agent-loaded platelet derivatives, or RNA agent-loaded thrombosomes. In some embodiments, the first composition is treated with a cationic transfection agent prior to the treating step (B) (2). In some embodiments, the first composition is treated with a cationic transfection agent during the treating step (B) (2). In some embodiments, the first composition is treated with a cationic transfection agent both prior to and during the treating step (B) (2). In some embodiments, the methods further include drying the RNA agent-loaded platelets or the RNA agent-loaded platelet derivatives obtained in step (B) (2). In some embodiments, the methods further include freeze-drying the RNA agent-loaded platelets or the RNA agent-loaded platelet derivatives. In such embodiments, the methods may further include rehydrating the RNA agent-loaded platelets or the RNA agent-loaded platelet derivatives obtained from the drying step. In some embodiments, the methods that further include drying the RNA agent-loaded platelets or the RNA agent-loaded platelet derivatives and rehydrating the RNA agent-loaded platelets or the RNA agent-loaded platelet derivatives obtained from the drying step provides rehydrated platelets or thrombosomes comprising at least 10% of the amount of the RNA agent of step (B) (2). In some embodiments, the methods that further include drying the RNA agent-loaded platelets or the RNA agent-loaded platelet derivatives and rehydrating the RNA agent-loaded platelets or the RNA agent-loaded platelet derivatives obtained from the drying step provides rehydrated platelets or thrombosomes comprising from about 0.1 nM to about 10 µM, such as about 1 nM to about 1 µM, such as about 10 nM to 10 µM, such as about 100 nM of the RNA agent of step (B) (2).

In some embodiments, the pooled platelets, platelet derivatives, or thrombosomes are treated with the RNA agent and with the buffer concurrently.

Thus, in some embodiments provided herein is a method of preparing RNA agent-loaded platelets, RNA agent-loaded platelet derivatives, or RNA agent-loaded thrombosomes, comprising: step (A) pooling platelets, platelet derivatives, or thrombosomes from a plurality of donors; and step (B) treating the platelets, the platelet derivatives, or the thrombosomes with a RNA agent and a cationic transfection reagent in the presence of a buffer comprising a salt, a base, a loading agent, and optionally ethanol, to form the RNA agent-loaded platelets, the RNA agent-loaded platelet derivatives, or the RNA agent-loaded thrombosomes. In some embodiments, the methods further include drying the RNA agent-loaded platelets or the RNA agent-loaded platelet derivatives obtained in step (B). In some embodiments, the methods further include freeze-drying the RNA agent-loaded platelets or the RNA agent-loaded platelet derivatives. In such embodiments, the methods may further include rehydrating the RNA agent-loaded platelets or the RNA agent-loaded platelet derivatives obtained from the drying step. In some embodiments, the methods that further include drying the RNA agent-loaded platelets or the RNA agent-loaded platelet derivatives and rehydrating the RNA agent-loaded platelets or the RNA agent-loaded platelet derivatives obtained from the drying step provides rehydrated platelets or thrombosomes comprising at least 10% of the amount of the RNA agent of step (B). In some embodiments, the methods that further include drying the RNA agent-loaded platelets or the RNA agent-loaded platelet derivatives and rehydrating the RNA agent-loaded platelets or the RNA agent-loaded platelet derivatives obtained from the drying step provides rehydrated platelets or thrombosomes comprising from about 0.1 nM to about 10 µM, such as about 1 nM to about 1 µM, such as about 10 nM to 10 µM, such as about 100 nM of the RNA agent of step (B).

In some embodiments, the methods of preparing RNA agent-loaded platelets, RNA agent-loaded platelet derivatives, or RNA agent-loaded thrombosomes that include pooling platelets, platelet derivatives, or thrombosomes from a plurality of donors include a viral inactivation step.

In some embodiments, the methods of preparing RNA agent-loaded platelets, RNA agent-loaded platelet derivatives, or RNA agent-loaded thrombosomes that include pooling platelets, platelet derivatives, or thrombosomes from a plurality of donors do not include a viral inactivation step.

In some embodiments, the platelets, the platelet derivatives, or the thrombosomes are loaded with the RNA agent in a period of time of about less than 1 minute to 48 hours, such as 5 minutes to 24 hours, such as 20 minutes to 12 hours, such as 30 minutes to 6 hours, such as 1 hour to 3 hours, such as about 2 hours. In some embodiments, platelets, platelet derivatives, or thrombosomes are loaded with the RNA agent for a time of about 1 minute, 2 minutes, 3 minutes, 4 minutes, 5 minutes, 6 minutes, 7 minutes, 8 minutes, 9 minutes, 10 minutes, 15 minutes, 20 minutes, 25 minutes, 30 minutes, 35 minutes, 40 minutes, 45 minutes, 50 minutes, minutes, 1 hour, 2 hours, 3 hours, 4 hours, 5 hours, 6 hours, 7 hours, 8 hours, 9 hours 10 hours, 11 hours, 12 hours, 13 hours, 14 hours, 15 hours, 16 hours, 17 hours, 18 hours, 19 hours, hours, 21 hours, 22 hours, 23 hours, 24 hours, or longer, or any time period range therein. In some embodiments, platelets, platelet derivatives, or thrombosomes are loaded with the RNA agent for a time of less than one minute. In some embodiments, a concentration of RNA agent from about 0.1 nM to about 10 µM, such as about 1 nM to about 1 µM, such as about 10 nM to µM, such as about 100 nM is loaded in a period of time of about less than 1 minute to 48 hours, such as 5 minutes to 24 hours, such as 20 minutes to 12 hours, such as 30 minutes to 6 hours, such as 1 hour minutes to 3 hours, such as about 2 hours.

In some embodiments, provided herein are RNA agent-loaded platelets, RNA agent-loaded platelet derivatives, or RNA agent-loaded thrombosomes prepared according to any of the variety of methods disclosed herein. In some embodiments provided herein are rehydrated platelets, platelet derivatives, or thrombosomes prepared as according to any of the variety of methods disclosed herein.

In some embodiments, RNA agent-loaded platelets, RNA agent-loaded platelet derivatives, or RNA agent-loaded thrombosomes protect the RNA agent from metabolic degradation or inactivation. RNA agent delivery with RNA agent-loaded platelets, RNA agent-loaded platelet derivatives, or RNA agent-loaded thrombosomes may therefore be advantageous in treatment of diseases such as cancer, since RNA agent-loaded platelets, RNA agent-loaded platelet derivatives, or RNA agent-loaded thrombosomes facilitate targeting of cancer cells while mitigating systemic side effects. RNA agent-loaded platelets, RNA agent-loaded platelet derivatives, or RNA agent-loaded thrombosomes may be used in any therapeutic setting in which expedited healing process is required or advantageous.

Accordingly, in some embodiments, provided herein is a method of treating a disease (e.g., any of the variety of diseases disclosed herein), comprising administering any of the variety of RNA agent-loaded platelets, RNA agent-loaded platelet derivatives, or RNA agent-loaded thrombosomes disclosed herein. Accordingly, in some embodiments, provided herein is a method of treating a disease (e.g., any of the variety of diseases disclosed herein), comprising administering cold stored, room temperature stored, cryopreserved thawed, rehydrated, and/or lyophilized platelets, platelet derivatives, or thrombosomes as disclosed herein. In some embodiments, the disease is cancer. In some embodiments, the disease is, Traumatic Brain injury. In some embodiments, the disease is ITP. In some embodiments, the disease is TTP. In some embodiments, the disease is hemophilia. In some embodiments, the disease is inherited disorders. In some embodiments, the disease is heart disease. In some embodiments, the disease is kidney disease. In some embodiments, the disease is a nervous system development disease. In some embodiments, the disease is hemostasis. In some embodiments, the disease is obesity.

DETAILED DESCRIPTION

Figure 1:
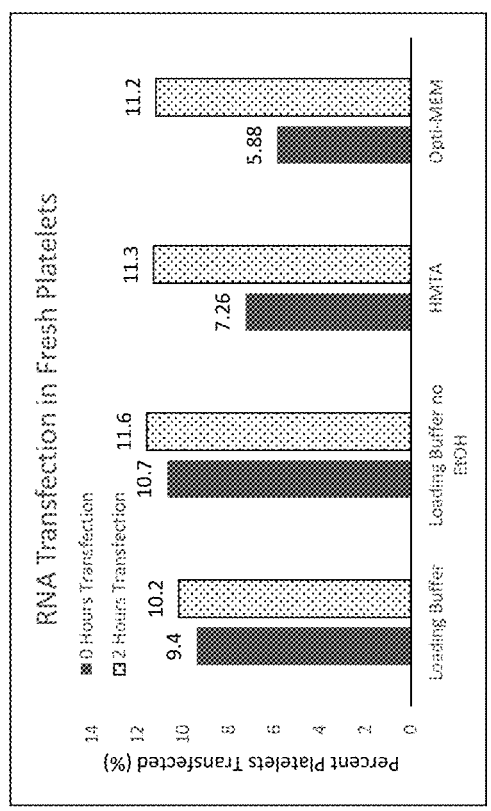
FIG. 1 shows percent transfection of fresh platelets with fluorescent siRNA incubated for 2 hours in different liquid transfection media. HMTA=HEPES-buffered Tryode's Solution. Opti-MEM=Opti-MEM™ (ThermoSci). EtOH=Ethanol.

It is to be understood that the terminology used herein is for the purpose of describing particular embodiments only and is not intended to be limiting. Further, where a range of values is disclosed, the skilled artisan will understand that all other specific values within the disclosed range are inherently disclosed by these values and the ranges they represent without the need to disclose each specific value or range herein. For example, a disclosed range of 1-10 includes 1-9,1-5, 2-10, 3.1-6, 1, 2, 3, 4, 5, and so forth. In addition, each disclosed range includes up to 5% lower for the lower value of the range and up to 5% higher for the higher value of the range. For example, a disclosed range of 4-10 includes 3.8-10.5. This concept is captured in this document by the term "about".

Unless defined otherwise, all technical and scientific terms used herein have the same meaning as commonly understood by one of ordinary skill in the art to which the term belongs. Although any methods and materials similar or equivalent to those described herein can be used in the practice or testing of the present disclosure, the preferred methods and materials are now described. All publications mentioned herein are incorporated herein by reference to disclose and describe the methods and/or materials in connection with which the publications are cited. The present disclosure is controlling to the extent it conflicts with any incorporated publication.

As used herein and in the appended claims, the term "platelet" can include whole platelets, fragmented platelets, platelet derivatives, or thrombosomes. Thus, for example, reference to "RNA agent-loaded platelets" may be inclusive of RNA agent-loaded platelets as well as RNA agent-loaded platelet derivatives or RNA agent-loaded thrombosomes, unless the context clearly dictates a particular form.

As used herein, "thrombosomes" (sometimes also herein called "Tsomes" or "Ts", particularly in the Examples and Figures) are platelet derivatives that have been treated with an incubating agent (e.g., any of the incubating agents described herein) and lyopreserved (e.g., freeze-dried). In some cases, thrombosomes can be prepared from pooled platelets. Thrombosomes can have a shelf life of 2-3 years in dry form at ambient temperature and can be rehydrated with sterile water within minutes for immediate infusion.

As used herein and in the appended claims, the term "fresh platelet" can include day of use platelets.

As used herein and in the appended claims the term "stored platelet" can include platelets stored for approximately 24 hours or longer before use.

As used herein and in the appended claims, the singular forms "a", "an", and "the" include plural referents unless the context clearly dictates otherwise. Thus, for example, reference to "a platelet" includes a plurality of such platelets. Furthermore, the use of terms that can be described using equivalent terms include the use of those equivalent terms. Thus, for example, the use of the term "subject" is to be understood to include the terms "patient", "individual" and other terms used in the art to indicate one who is subject to a treatment.

In some embodiments, rehydrating the RNA agent-loaded platelets includes adding to the platelets an aqueous liquid. In some embodiments, the aqueous liquid is water. In some embodiments, the aqueous liquid is an aqueous solution. In some embodiments, the aqueous liquid is a saline solution. In some embodiments, the aqueous liquid is a suspension.

In some embodiments, the rehydrated platelets have coagulation factor levels showing all individual factors (e.g., Factors VII, VIII and IX) associated with blood clotting at 40 international units (IU) or greater.

In some embodiments, the dried platelets, such as freeze-dried platelets, have less than about 10%, such as less than about 8%, such as less than about 6%, such as less than about 4%, such as less than about 2%, such as less than about 0.5% crosslinking of platelet membranes via proteins and/or lipids present on the membranes. In some embodiments, the rehydrated platelets, have less than about 10%, such as less than about 8%, such as less than about 6%, such as less than about 4%, such as less than about 2%, such as less than about 0.5% crosslinking of platelet membranes via proteins and/or lipids present on the membranes.

In some embodiments, the RNA agent-loaded platelets and the dried platelets, such as freeze-dried platelets, having a particle size (e.g., diameter, max dimension) of at least about 0.2 µm (e.g., at least about 0.3 µm, at least about 0.4 µm, at least about 0.5 µm, at least about 0.6 µm, at least about 0.7 µm, at least about 0.8 µm, at least about 0.9 µm, at least about 1.0 µm, at least about 1.0 µm, at least about 1.5 µm, at least about 2.0 µm, at least about 2.5 µm, or at least about 5.0 µm). In some embodiments, the particle size is less than about 5.0 µm (e.g., less than about 2.5 µm, less than about 2.0 µm, less than about 1.5 µm, less than about 1.0 µm, less than about 0.9 µm, less than about 0.8 µm, less than about 0.7 µm, less than about 0.6 µm, less than about 0.5 µm, less than about 0.4 µm, or less than about 0.3 µm). In some embodiments, the particle size is from about 0.3 µm to about 5.0 µm (e.g., from about 0.4 µm to about 4.0 µm, from about 0.5 µm to about 2.5 µm, from about 0.6 µm to about 2.0 µm, from about 0.7 µm to about 1.0 µm, from about 0.5 µm to about 0.9 µm, or from about 0.6 µm to about 0.8 µm).

In some embodiments, at least 50% (e.g., at least about 55%, at least about 60%, at least about 65%, at least about 70%, at least about 75%, at least about 80%, at least about 85%, at least about 90%, at least about 95%, or at least about 99%) of platelets and/or the dried platelets, such as freeze-dried platelets, have a particle size in the range of about 0.3 µm to about 5.0 µm (e.g., from about 0.4 µm to about 4.0 µm, from about 0.5 µm to about 2.5 µm, from about 0.6 µm to about 2.0 µm, from about 0.7 µm to about 1.0 µm, from about 0.5 µm to about 0.9 µm, or from about 0.6 µm to about 0.8 µm). In some embodiments, at most 99% (e.g., at most about 95%, at most about 80%, at most about 75%, at most about 70%, at most about 65%, at most about 60%, at most about 55%, or at most about 50%) of platelets and/or the dried platelets, such as freeze-dried platelets, are in the range of about 0.3 µm to about 5.0 µm (e.g., from about 0.4 µm to about 4.0 µm, from about 0.5 µm to about 2.5 µm, from about 0.6 µm to about 2.0 µm, from about 0.7 µm to about 1.0 µm, from about 0.5 µm to about 0.9 µm, or from about 0.6 µm to about 0.8 µm). In some embodiments, about 50% to about 99% (e.g., about 55% to about 95%, about 60% to about 90%, about 65% to about 85, about 70% to about 80%) of platelets and/or the dried platelets, such as freeze-dried platelets, are in the range of about 0.3 µm to about 5.0 µm (e.g., from about 0.4 µm to about 4.0 µm, from about 0.5 µm to about 2.5 µm, from about 0.6 µm to about 2.0 µm, from about 0.7 µm to about 1.0 µm, from about 0.5 µm to about 0.9 µm, or from about 0.6 µm to about 0.8 µm).

In some embodiments, platelets are isolated prior to treating the platelets with a RNA agent.

Accordingly, in some embodiments, the methods for preparing RNA agent-loaded platelets includes: step (a) isolating platelets, for example in a liquid medium; and step (b) treating the platelets with a RNA agent, a cationic transfection reagent, and with a loading buffer comprising a salt, a base, a loading agent, and optionally ethanol, to form the RNA agent-loaded platelets, Accordingly, in some embodiments, the methods for preparing RNA agent-loaded platelets includes: step (a) isolating platelets, for example in a liquid medium; step (b) treating the platelets with a RNA agent to form a first composition; and step (c) treating the first composition with a buffer comprising a salt, a base, a loading agent, and optionally at least one organic solvent to form the RNA agent-loaded platelets. In some embodiments, the methods further include treating the first composition with a cationic transfection reagent to form a second composition. In some embodiments, the second composition is treated with a buffer comprising a salt, a base, a loading agent, and optionally at least one organic solvent to form the RNA agent-loaded platelets, RNA agent-loaded platelet derivatives, or RNA agent-loaded thrombosomes. In some embodiments, the first composition is treated with a cationic transfection agent prior to the treating step (c). In some embodiments, the first composition is treated with a cationic transfection agent during the treating step (c). In some embodiments, the first composition is treated with a cationic transfection agent both prior to and during the treating step (c).

In some embodiments, suitable organic solvents include, but are not limited to alcohols, esters, ketones, ethers, halogenated solvents, hydrocarbons, nitriles, glycols, alkyl nitrates, water or mixtures thereof. In some embodiments, suitable organic solvents includes, but are not limited to methanol, ethanol, n-propanol, isopropanol, acetic acid, acetone, methyl ethyl ketone, methyl isobutyl ketone, methyl acetate, ethyl acetate, isopropyl acetate, tetrahydrofuran, isopropyl ether (IPE), tert-butyl methyl ether, dioxane (e.g., 1,4-dioxane), acetonitrile, propionitrile, methylene chloride, chloroform, toluene, anisole, cyclohexane, hexane, heptane, ethylene glycol, nitromethane, dimethylformamide, dimethyl sulfoxide, N-methyl pyrrolidone, dimethylacetamide, and combinations thereof.

Accordingly, in some embodiments, the methods for preparing RNA agent-loaded platelets includes: step (a) isolating platelets, for example in a liquid medium; step (b) treating the platelets with a buffer comprising a salt, a base, a loading agent, and optionally at least one organic solvent, to form a first composition; and step (c)treating the first composition with a RNA agent, to form the RNA agent-loaded platelets. In some embodiments, the methods further include treating the first composition with a cationic transfection reagent to form a second composition. In some embodiments, the second composition is treated with a buffer comprising a salt, a base, a loading agent, and optionally at least one organic solvent to form the RNA agent-loaded platelets, RNA agent-loaded platelet derivatives, or RNA agent-loaded thrombosomes. In some embodiments, the first composition is treated with a cationic transfection agent prior to the treating step (c). In some embodiments, the first composition is treated with a cationic transfection agent during the treating step (c). In some embodiments, the first composition is treated with a cationic transfection agent both prior to and during the treating step (c).

In some embodiments, isolating platelets includes isolating platelets from blood.

In some embodiments, platelets are donor-derived platelets. In some embodiments, platelets are obtained by a process that includes an apheresis step. In some embodiments, platelets are fresh platelets. In some embodiments, platelets are stored platelets.

In some embodiments, platelets are derived in vitro. In some embodiments, platelets are derived or prepared in a culture prior to treating the platelets with a RNA agent. In some embodiments, preparing the platelets includes deriving or growing the platelets from a culture of megakaryocytes. In some embodiments, preparing the platelets includes deriving or growing the platelets (or megakaryocytes) from a culture of human pluripotent stem cells (PCSs), including embryonic stem cells (ESCs) and/or induced pluripotent stem cells (iPSCs).

Accordingly, in some embodiments, the methods for preparing RNA agent-loaded platelets includes: step (a) preparing platelets; and step (b) treating the platelets with a RNA agent, a cationic transfection reagent, and with a loading buffer comprising a salt, a base, a loading agent, and optionally at least one organic solvent, to form the RNA agent-loaded platelets.

Accordingly, in some embodiments, the methods for preparing RNA agent-loaded platelets includes: step (a) preparing platelets; step (b) treating the platelets with a RNA agent to form a first composition; and step (c) treating the first composition with a buffer comprising a salt, a base, a loading agent, and optionally at least one organic solvent, to form the RNA agent-loaded platelets.

Accordingly, in some embodiments, the methods for preparing RNA agent-loaded platelets includes: step (a) preparing platelets; step (b) treating the platelets with a buffer comprising a salt, a base, a loading agent, and optionally at least one organic solvent, to form a first composition; and step (c) treating the first composition with a RNA agent, to form the RNA agent-loaded platelets. In some embodiments, the methods further include treating the first composition with a cationic transfection reagent to form a second composition. In some embodiments, the second composition is treated with a buffer comprising a salt, a base, a loading agent, and optionally at least one organic solvent to form the RNA agent-loaded platelets, RNA agent-loaded platelet derivatives, or RNA agent-loaded thrombosomes. In some embodiments, the first composition is treated with a cationic transfection agent prior to the treating step (c). In some embodiments, the first composition is treated with a cationic transfection agent during the treating step (c). In some embodiments, the first composition is treated with a cationic transfection agent both prior to and during the treating step (c).

In some embodiments, no solvent is used. Thus, in some embodiments, the method for preparing RNA agent-loaded platelets comprises:
a) isolating platelets, for example in a liquid medium;
b) treating the platelets with a RNA agent and with a loading buffer comprising a salt, a base, and a loading agent, to form the RNA agent-loaded platelets,
wherein the method does not comprise treating the platelets with an organic solvent such as ethanol.

Thus, in some embodiments, the method for preparing RNA agent-loaded platelets comprises:
a) isolating platelets, for example in a liquid medium;
b) treating the platelets with a RNA agent to form a first composition; and
c) treating the first composition with a buffer comprising a salt, a base, and a loading agent, to form the RNA agent-loaded platelets,
wherein the method does not comprise treating the platelets with an organic solvent such as ethanol and the method does not comprise treating the first composition with an organic solvent such as ethanol.

Thus, in some embodiments, the method for preparing RNA agent-loaded platelets comprises:
a) isolating platelets, for example in a liquid medium;
b) treating the platelets with a buffer comprising a salt, a base, and a loading agent, to form a first composition; and
c) treating the first composition with a RNA agent, to form the RNA agent-loaded platelets.
wherein the method does not comprise treating the platelets with an organic solvent such as ethanol and the method does not comprise treating the first composition with an organic solvent such as ethanol.

In some embodiments, the method for preparing RNA agent-loaded platelets comprises:
a) preparing platelets; and
b) treating the platelets with a RNA agent-loaded and with a loading buffer comprising a salt, a base, and a loading agent, to form the RNA agent-loaded platelets,
wherein the method does not comprise treating the platelets with an organic solvent such as ethanol.

Thus, in some embodiments, the method for preparing RNA agent-loaded platelets comprises:
a) preparing platelets;
b) treating the platelets with a RNA agent to form a first composition; and
c) treating the first composition with a buffer comprising a salt, a base, and a loading agent, to form the RNA agent-loaded platelets,
wherein the method does not comprise treating the platelets with an organic solvent such as ethanol and the method does not comprise treating the first composition with an organic solvent such as ethanol.

Thus, in some embodiments, the method for preparing RNA agent-loaded platelets comprises:
a) preparing platelets;
b) treating the platelets with a buffer comprising a salt, a base, and a loading agent, to form a first composition; and
c) treating the first composition with a RNA agent, to form the RNA agent-loaded platelets.
wherein the method does not comprise treating the platelets with an organic solvent such as ethanol and the method does not comprise treating the first composition with an organic solvent such as ethanol.

In some embodiments, the loading agent is a saccharide. In some embodiments, the saccharide is a monosaccharide. In some embodiments, the saccharide is a disaccharide. In some embodiments, the saccharide is a non-reducing disaccharide. In some embodiments, the saccharide is sucrose, maltose, trehalose, glucose (e.g., dextrose), mannose, or xylose. In some embodiments, the loading agent is a starch.

In some embodiments, the loading agent is a carrier protein.

As used herein, the term "RNA agent" is any microRNA (also known as miRNA) excluding miRNA23a and/or miRNA27a, and/or any small interfering RNA (also known as siRNA, short interfering RNA, or silencing RNA).

As used herein, the terms "microRNA" and "miRNA" refer to a non-specific non-coding ribonucleic acid duplex that targets and silences multiple RNA molecules, excluding miRNA23a and/or miRNA27a. Many miRNAs are naturally occurring, but miRNAs can also be synthesized by those of ordinary skill in the art. Mature miRNAs are generally 19-25 nucleotides in length, have 3' overhangs of two nucleotides, target multiple mRNAs and are typically only partially complementary to their target mRNAs. miRNAs typically function by repressing translation and facilitating mRNA degradation.

As used herein, the term "small interfering RNA" refers to a double-stranded specific non-coding RNA that targets and silences a single RNA molecule. Many siRNAs are naturally occurring, but siRNAs can also be synthesized by those of ordinary skill in the art. siRNA are generally derived from strands of exogenous growing (originating from outside an organism) RNA, which is taken up by the cell and undergoes further processing. Mature siRNAs are generally 19-27 nucleotides in length, have 3' overhangs of two nucleotides at each end that can be used to "interfere" with the translation of proteins by binding to and promoting the degradation of messenger RNA at specific sequences. Each siRNA strand has a 5' phosphate group and a 3' hydroxyl (OH) group. siRNA can be produced from dsRNA or hairpin looped RNA and processed into siRNAs by the Dicer enzyme. siRNA can also be incorporated into a multi-subunit protein complex called RNA-induced silencing complex (RISC).

miRNAs and siRNAs are distinct from other types of RNA molecules including, without limitation, messenger RNA ("mRNA), ribosomal RNA ("rRNA"), small nuclear RNA ("snRNA"), transfer RNA ("tRNA"), and short hairpin RNA ("shRNA"). mRNA, rRNA, snRNA, and tRNA are canonical classes of RNA molecules, the function and structure of which are well-known to those of ordinary skill in the art.

In some embodiments, the RNA agent is a miRNA (e.g., a single species of miRNA or two or more species of miRNA). In some embodiments, the RNA agent is a siRNA (e.g., a single species of siRNA or two or more species of siRNA). In some embodiments, the RNA agent is a combination of a miRNA (e.g., a single species of miRNA or two or more species of miRNA) and a siRNA (e.g., a single species of siRNA or two or more species of siRNA).

In various methods described herein, platelets are loaded with one or more of a variety of RNA agents. In some embodiments, platelets are loaded with one or more miRNA and/or a siRNA, including but not limited to siRNA targeting IL-13 (interleukin 17), IL-6 (interleukin 6), TNFα (tumor necrosis factor alpha), Braf (v-raf murine sarcoma viral oncogene homolog B), Akt (protein kinase B), Hsp27 (heat shock protein 27), CD44, P-glycoprotein, Bcl-xL (B-cell lymphoma extra large), Mst (myostatin), VEGF (vascular endothelial growth factor), FcγRIII (immunoglobulin type G cell surface Fc receptor), STAT3 (signal transducer and activator of transcription 3), RRM2 (ribonucleotide reductase subunit M2), PLK1 (polo-like kinase), Mcl1 (myeloid cell leukemia sequence 1), PKN3 (protein kinase N3), c-Myc (v-myc avian myelocytomatosis viral oncogene homolog), MDM2 (mouse double minute 2 homolog), polymerase of Ebola virus, XIAP (X-linked inhibitor of apoptosis protein), RAGE (receptor for advanced glycation end-products), KSP (kinesin spindle protein), mutated KRAS (Kirsten rat sarcoma viral oncogene homolog), EphA2 (ephrin type-A receptor 2), RSV nucleocapsid (respiratory syncytial virus nucleocapsid), ADRB2 (beta-2 adrenergic receptor), RTP801 (hypoxia-inducible factor 1 responsive gene), CASP2 (Caspase-2), TRPV1 (transient receptor potential cation channel subfamily V member 1), PCSK9 (proprotein convertase subtilisin/kexin type 9), ApoB (apolipoprotein B), HSP47 (heat shock protein 47), p53, Keratin 6a, AT (antithrombin), TTR (transthyretin), miRNA-145, miRNA-33a, miRNA-7, miRNA-34a, miRNA-16, miRNA-143, miRNA-29b, miRNA-122, miRNA-10b, miRNA-221, miRNA-21, miRNA-33, miRNA-155, miRNA-92, miRNA-15. Lam et. al. in www.ncbi.nlm.nih.gov/pmc/articles/PMC4877448/pdf/mtna201523a.pdf and Christopher et al. in www.ncbi.nlm.nih.gov/pmc/articles/PMC4840794/describe further embodiments of miRNA and/or siRNA platelets can be loaded with and are herein incorporated by reference in their entirety.

In some embodiments, a RNA agent loaded into platelets is modified. For example, a RNA agent can be modified to increase its stability during the platelet loading process, while the RNA agent is loaded into the platelet, and/or after the RNA agent's release from a platelet. In some embodiments, the modified RNA agent's stability is increased with little or no adverse effect on its activity. For example, the modified RNA agent can have at least 70%, 75%, 80%, 85%, 90%, 95%, 96%, 97%, 98%, 99% or more of the activity of the corresponding unmodified RNA agent. In some embodiments, the modified RNA agent has 100% (or more) of the activity of the corresponding unmodified RNA agent. Various modifications that stabilize RNA agents are known in the art. In some embodiments, the RNA agent is stabilized by one or more of a stabilizing oligonucleotide (see, e.g., U.S. Application Publication No. 2018/0311176), a backbone/side chain modification (e.g., a 2-sugar modification such as a 2'-fluor, methoxy, or amine substitution, or a 2'-thio(-SH), 2'-azido(-N3), or 2'-hydroxymethyl (-CH2OH) modification), an unnatural nucleic acid substitution (e.g., an S-glycerol, cyclohexenyl, and/or threose nucleic acid substitution, an L-nucleic acid substitution, a locked nucleic acid (LNA) modification (e.g., the ribose moiety of an LNA nucleotide is modified with an extra bridge connecting the 2' oxygen and 4' carbon), conjugation with PEG, a nucleic acid bond modification or replacement (e.g., a phosphorothioate bond, a methylphosphonate bond, or a phosphorodiamidate bond), a reagent or reagents (e.g., intercalating agents such as coralyne, neomycin, and ellipticine; also see US Publication Application Nos. 2018/0312903 and 2017/0198335, each of which are incorporated herein by reference in their entireties, for further examples of stabilizing reagents).

In some embodiments, a RNA agent loaded into platelets is modified to include an imaging agent. For example, a RNA agent can be modified with an imaging agent in order to image the RNA agent loaded platelet in vivo. In some embodiments, a RNA agent can be modified with two or more imaging agents (e.g., any two or more of the imaging agents described herein). In some embodiments, a RNA agent loaded into platelets is modified with a radioactive metal ion, a paramagnetic metal ion, a gamma-emitting radioactive halogen, a positron-emitting radioactive non-metal, a hyperpolarized NMR-active nucleus, a reporter suitable for in vivo optical imaging, or a beta-emitter suitable for intravascular detection. For example, a radioactive metal ion can include, but is not limited to, positron emitters such as $^{54}$Cu, $^{48}$V, $^{52}$Fe, $^{55}$Co, $^{94}$Tc or $^{68}$Ga; or gamma-emitters such as $^{171}$Tc, $^{111}$In, or $^{67}$Ga. For example, a paramagnetic metal ion can include, but is not limited to Gd(III), a Mn(II), a Cu(II), a Cr(III), a Fe(III), a Co(II), a Er(II), a Ni(II), a Eu(III) or a Dy(III), an element comprising an Fe element, a neodymium iron oxide (NdFeO3) or a dysprosium iron oxide (DyFeO3). For example, a paramagnetic metal ion can be chelated to a polypeptide or a monocrystalline nanoparticle. For example, a gamma-emitting radioactive halogen can include, but is not limited to $^{123}$I, $^{131}$I or $^{77}$Br. For example, a positron-emitting radioactive non-metal can include, but is not limited to $^{11}$C, $^{13}$N, $^{15}$O, $^{17}$F, $^{18}$F, $^{75}$Br, $^{76}$Br or $^{124}$I. For example, a hyperpolarized NMR-active nucleus can include, but is not limited to $^{13}$C, $^{15}$N, $^{19}$F, $^{29}$Si and $^{31}$P. For example, a reporter suitable for in vivo optical imaging can include, but is not limited to any moiety capable of detection either directly or indirectly in an optical imaging procedure. For example, the reporter suitable for in vivo optical imaging can be a light scatterer (e.g., a colored or uncolored particle), a light absorber or a light emitter. For example, the reporter can be any reporter that interacts with light in the electromagnetic spectrum with wavelengths from the ultraviolet to the near infrared. For example, organic chromophoric and fluorophoric reporters include groups having an extensive delocalized electron system, e.g. cyanines, merocyanines, indocyanines, phthalocyanines, naphthalocyanines, triphenylmethines, porphyrins, pyrilium dyes, thiapyrilium dyes, squarylium dyes, croconium dyes, azulenium dyes, indoanilines, benzophenoxazinium dyes, benzothiaphenothiazinium dyes, anthraquinones, napthoquinones, indathrenes, phthaloylacridones, tri sphenoquinones, azo dyes, intramolecular and intermolecular charge-transfer dyes and dye complexes, tropones, tetrazines, b/s(dithiolene) complexes, bis(benzene-dithiolate) complexes, iodoaniline dyes, b/stS.O-dithiolene) complexes. For example, the reporter can be, but is not limited to a fluorescent, a bioluminescent, or chemiluminescent polypeptide. For example, a fluorescent or chemiluminescent polypeptide is a green florescent protein (GFP), a modified GFP to have different absorption/emission properties, a luciferase, an aequorin, an obelin, a mnemiopsin, a berovin, or a phenanthridinium ester. For example, a reporter can be, but is not limited to rare earth metals (e.g., europium, samarium, terbium, or dysprosium), or fluorescent nanocrystals (e.g., quantum dots). For example, a reporter may be a chromophore that can include, but is not limited to fluorescein, sulforhodamine 101 (Texas Red), rhodamine B, rhodamine 6G, rhodamine 19, indocyanine green, Cy2, Cy3, Cy3.5, Cy5, Cy5.5, Cy7, Marina Blue, Pacific Blue, Oregon Green 88, Oregon Green 514, tetramethylrhodamine, and Alexa Fluor 350, Alexa Fluor 430, Alexa Fluor 532, Alexa Fluor 546, Alexa Fluor 555, Alexa Fluor 568, Alexa Fluor 594, Alexa Fluor 633, Alexa Fluor 647, Alexa Fluor 660, Alexa Fluor 680, Alexa Fluor 700, and Alexa Fluor 750. For example, a beta-emitter can include, but is not limited to radio metals $^{67}$Cu, $^{89}$Sr, $^{90}$Y, $^{153}$Sm, $^{185}$Re, $^{188}$Re or $^{192}$Ir, and non-metals $^{32}$P, $^{33}$P, $^{38}$S, $^{38}$Cl, $^{39}$Cl, $^{82}$Br and $^{83}$Br. In some embodiments, a RNA agent loaded into platelets can be associated with gold or other equivalent metal particles (such as nanoparticles). For example, a metal particle system can include, but is not limited to gold nanoparticles (e.g., Nanogold™).

In some embodiments, a RNA agent loaded into platelets that is modified with an imaging agent is imaged using an imaging unit. The imaging unit can be configured to image the RNA agent loaded platelets in vivo based on an expected property (e.g., optical property from the imaging agent) to be characterized. For example, imaging techniques (in vivo imaging using an imaging unit) that can be used, are not limited to: computer assisted tomography (CAT), magnetic resonance spectroscopy (MRS), magnetic resonance imaging (MRI), positron emission tomography (PET), single-photon emission computed tomography (SPECT), or bioluminescence imaging (BLI). Chen et al. in the URL at [https://www.ncbi.nlm.nih.gov/pmc/articles/PMC3943245/] have described various imaging techniques and which is incorporated by reference herein in its entirety.

In some embodiments, such as embodiments wherein the platelets are treated with the RNA agent and the buffer sequentially as disclosed herein, the RNA agent may be loaded in a liquid medium that may be modified to change the proportion of media components or to exchange components for similar products, or to add components necessary for a given application.

In some embodiments, the loading buffer and/or the liquid medium include one or more of a) water or a saline solution, b) one or more additional salts, or c) a cationic transfection agent, or d) a base. In some embodiments, the loading buffer, and/or the liquid medium, may include one or more of a) DMSO, b) one or more salts, or c) a cationic transfection agent, or d) a base.

In some embodiments, the loading agent is loaded into the platelets in the presence of an aqueous medium. In some embodiments, the loading agent is loaded in the presence of a medium comprising DMSO. As an example, one embodiment of the methods herein includes treating platelets with a RNA agent and with an aqueous loading buffer comprising a salt, a base, a loading agent, a cationic transfection agent, and optionally at least one organic solvent, to form the RNA agent-loaded platelets. As an example, one embodiment of the methods herein includes treating platelets with a RNA agent and with a loading buffer comprising DMSO and comprising a salt, a base, a loading agent, a cationic transfection agent, and optionally ethanol, to form the RNA agent-loaded platelets.

In some embodiments, the loading buffer and/or the liquid medium, include one or more salts selected from phosphate salts, sodium salts, potassium salts, calcium salts, magnesium salts, and any other salt that can be found in blood or blood products, or that is known to be useful in drying platelets, or any combination of two or more of these.

Preferably, these salts are present in the composition at an amount that is about the same as is found in whole blood.

In some embodiments, the RNA agent-loaded platelets are prepared by incubating the platelets with the RNA agent in the liquid medium for different durations at or at different temperatures from about 15-45° C., or about 22° C. In some embodiments, the RNA agent-loaded platelets are prepared by incubating the platelets with the RNA agent in the liquid medium at a temperature from about 18-42° C., about 20-40° C., about 22-37° C., or about 16° C., about 18° C., about 20° C., about 22° C., about 24° C., about 26° C., about 28° C., about 30° C., about 32° C., about 34° C., about 36° C., about 37° C., about 39° C., about 41° C., about 43° C., or about 45° C. for at least about 5 minutes (mins) (e.g., at least about 20 mins, about 30 mins, about 1 hour (hr), about 2 hrs, about 3 hrs, about 4 hrs, about 5 hrs, about 6 hrs, about 7 hrs, about 8 hrs, about 9 hrs, about 10 hrs, about 12 hrs, about 16 hrs, about 20 hrs, about 24 hrs, about 30 hrs, about 36 hrs, about 42 hrs, about 48 hrs, or at least about 48 hrs. In some embodiments, the RNA agent-loaded platelets are prepared by incubating the platelets with the RNA agent in the liquid medium at a temperature from about 18-42° C., about 20-40° C., about 22-37° C., or about 16° C., about 18° C., about 20° C., about 22° C., about 24° C., about 26° C., about 28° C., about 30° C., about 32° C., about 34° C., about 36° C., about 37° C., about 39° C., about 41° C., about 43° C., or about 45° C. for no more than about 48 hrs (e.g., no more than about 20 mins, about 30 mins, about 1 hour (hr), about 2 hrs, about 3 hrs, about 4 hrs, about 5 hrs, about 6 hrs, about 7 hrs, about 8 hrs, about 9 hrs, about 10 hrs, about 12 hrs, about 16 hrs, about 20 hrs, about 24 hrs, about 30 hrs, about 36 hrs, or no more than about 42 hrs). In some embodiments, the RNA agent-loaded platelets are prepared by incubating the platelets with the RNA agent in the liquid medium from about 10 mins to about 48 hours (e.g., from about 20 mins to about 36 hrs, from about 30 mins to about 24 hrs, from about 1 hr to about 20 hrs, from about 2 hrs to about 16 hours, from about 10 mins to about 24 hours, from about 20 mins to about 12 hours, from about 30 mins to about 10 hrs, or from about 1 hr to about 6 hrs.

In some embodiments, the platelets form a suspension in a liquid medium at a concentration from 10,000 platelets/μL to 10,000,000 platelets/μL, such as 50,000 platelets/μL to 2,000,000 platelets/μL, such as 100,000 platelets/μL to 500,000 platelets/μL, such as 150,000 platelets/μL to 300,000 platelets/μL, such as 200,000 platelets/μL, such as 2,000,000 platelets/μL.

In some embodiments, one or more other components may be introduced into the platelets when the RNA agent is loaded. In some embodiments, the one or more other components are introduced concurrently with loading of the RNA agent. In some embodiments, the one or more other components are introduced into the platelet and the RNA agent is loaded into the platelet sequentially in either order. Exemplary other components that can be introduced into platelets include Prostaglandin E1 or Prostacyclin to prevent platelet aggregation and activation during the loading process. In some embodiments, the one or more other components that are loaded in the platelets comprise Prostaglandin E1 (PGE1) or Prostacyclin. In some embodiments, the one or more other components that are loaded in the platelets do not comprise Prostaglandin E1 or Prostacyclin.

In some embodiments, other components may include imaging agents. For example, an imaging agent can include, but is not limited to a radioactive metal ion, a paramagnetic metal ion, a gamma-emitting radioactive halogen, a positron-emitting radioactive non-metal, a hyperpolarized NMR-active nucleus, a reporter suitable for in vivo optical imaging, or a beta-emitter suitable for intravascular detection. For example, a radioactive metal ion can include, but is not limited to, positron emitters such as 54Cu, 48V, 52Fe, 55Co, 94Tc or 68Ga; or gamma-emitters such as 171Tc, 111In, 113In, or 67Ga. For example, a paramagnetic metal ion can include, but is not limited to Gd(III), a Mn(II), a Cu(II), a Cr(III), a Fe(III), a Co(II), a Er(II), a Ni(II), a Eu(III) or a Dy(III), an element comprising an Fe element, a neodymium iron oxide (NdFeO3) or a dysprosium iron oxide (DyFeO3). For example, a paramagnetic metal ion can be chelated to a polypeptide or a monocrystalline nanoparticle. For example, a gamma-emitting radioactive halogen can include, but is not limited to 123I, 131I or 77Br. For example, a positron-emitting radioactive non-metal can include, but is not limited to 11C, 13N, 15O, 17F, 18F, 75Br, 76Br or 124I. For example, a hyperpolarized NMR-active nucleus can include, but is not limited to 13C, 15N, 19F, 29Si and 31P. For example, a reporter suitable for in vivo optical imaging can include, but is not limited to any moiety capable of detection either directly or indirectly in an optical imaging procedure. For example, the reporter suitable for in vivo optical imaging can be a light scatterer (e.g., a colored or uncolored particle), a light absorber or a light emitter. For example, the reporter can be any reporter that interacts with light in the electromagnetic spectrum with wavelengths from the ultraviolet to the near infrared. For example, organic chromophoric and fluorophoric reporters include groups having an extensive delocalized electron system, e.g. cyanines, merocyanines, indocyanines, phthalocyanines, naphthalocyanines, triphenylmethines, porphyrins, pyrilium dyes, thiapyrilium dyes, squarylium dyes, croconium dyes, azulenium dyes, indoanilines, benzophenoxazinium dyes, benzothiaphenothiazinium dyes, anthraquinones, napthoquinones, indathrenes, phthaloylacridones, trisphenoquinones, azo dyes, intramolecular and intermolecular charge-transfer dyes and dye complexes, tropones, tetrazines, b/s(dithiolene) complexes, bis(benzene-dithiolate) complexes, iodoaniline dyes, b/stS.O-dithiolene) complexes. For example, the reporter can be, but is not limited to a fluorescent, a bioluminescent, or chemiluminescent polypeptide. For example, a fluorescent or chemiluminescent polypeptide is a green florescent protein (GFP), a modified GFP to have different absorption/emission properties, a luciferase, an aequorin, an obelin, a mnemiopsin, a berovin, or a phenanthridinium ester. For example, a reporter can be, but is not limited to rare earth metals (e.g., europium, samarium, terbium, or dysprosium), or fluorescent nanocrystals (e.g., quantum dots). For example, a reporter may be a chromophore that can include, but is not limited to fluorescein, sulforhodamine 101 (Texas Red), rhodamine B, rhodamine 6G, rhodamine 19, indocyanine green, Cy2, Cy3, Cy3.5, Cy5, Cy5.5, Cy7, Marina Blue, Pacific Blue, Oregon Green 88, Oregon Green 514, tetramethylrhodamine, and Alexa Fluor 350, Alexa Fluor 430, Alexa Fluor 532, Alexa Fluor 546, Alexa Fluor 555, Alexa Fluor 568, Alexa Fluor 594, Alexa Fluor 633, Alexa Fluor 647, Alexa Fluor 660, Alexa Fluor 680, Alexa Fluor 700, and Alexa Fluor 750. For example, a beta-emitter can include, but is not limited to radio metals 67Cu, 89Sr, 90Y, 153 Sm, 185Re, 188Re or 192Ir, and non-metals 32P, 33P, 38S, 38Cl, 39Cl, 82Br and 83Br. In some embodiments, a RNA agent loaded into platelets can be associated with gold or other equivalent metal particles (such as nanoparticles). For example, a metal particle system can include, but is not limited to gold nanoparticles (e.g., Nanogold™).

In some embodiments, the RNA agent-loaded platelets are prepared by incubating the platelets with the RNA agent in the liquid medium for different durations. The step of incubating the platelets to load one or more RNA agent(s), includes incubating the platelets for a time suitable for loading, as long as the time, taken in conjunction with the temperature, is sufficient for the RNA agent to come into contact with the platelets and, preferably, be incorporated, at least to some extent, into the platelets. For example, in some embodiments, the RNA agent-loaded platelets are prepared by incubating the platelets with the RNA agent in the liquid medium for at least about 5 minutes (mins) (e.g., at least about 20 mins, about 30 mins, about 1 hour (hr), about 2 hrs, about 3 hrs, about 4 hrs, about 5 hrs, about 6 hrs, about 7 hrs, about 8 hrs, about 9 hrs, about 10 hrs, about 12 hrs, about 16 hrs, about 20 hrs, about 24 hrs, about 30 hrs, about 36 hrs, about 42 hrs, about 48 hrs, or at least about 48 hrs. In some embodiments, the RNA agent-loaded platelets are prepared by incubating the platelets with the RNA agent in the liquid medium for no more than about 48 hrs (e.g., no more than about 20 mins, about 30 mins, about 1 hour (hr), about 2 hrs, about 3 hrs, about 4 hrs, about 5 hrs, about 6 hrs, about 7 hrs, about 8 hrs, about 9 hrs, about 10 hrs, about 12 hrs, about 16 hrs, about 20 hrs, about 24 hrs, about 30 hrs, about 36 hrs, or no more than about 42 hrs). In some embodiments, the RNA agent-loaded platelets are prepared by incubating the platelets with the RNA agent in the liquid medium from about 10 mins to about 48 hours (e.g., from about 20 mins to about 36 hrs, from about 30 mins to about 24 hrs, from about 1 hr to about 20 hrs, from about 2 hrs to about 16 hours, from about 10 mins to about 24 hours, from about 20 mins to about 12 hours, from about 30 mins to about 10 hrs, or from about 1 hr to about 6 hrs.

In some embodiments, the RNA agent-loaded platelets are prepared by incubating the platelets with the RNA agent in the liquid medium at different temperatures. The step of incubating the platelets to load one or more RNA agent(s), includes incubating the platelets with the RNA agent in the liquid medium at a temperature that, when selected in conjunction with the amount of time allotted for loading, is suitable for loading. In general, the platelets with the RNA agent in the liquid medium are incubated at a suitable temperature (e.g., a temperature above freezing) for at least a sufficient time for the RNA agent to come into contact with the platelets. In some embodiments, incubation is conducted at 22° C. In certain embodiments, incubation is performed at 4° C. to 45° C., such as 15° C. to 42° C. For example, in some embodiments, incubation is performed from about 18-42° C., about 20-40° C., about 22-37° C., or about 16° C., about 18° C., about 20° C., about 22° C., about 24° C., about 26° C., about 28° C., about 30° C., about 32° C., about 34° C., about 36° C., about 37° C., about 39° C., about 41° C., about 43° C., or about 45° C. for 110 to 130 (e.g., 120) minutes and for as long as 24-48 hours.

In some embodiments of the methods of preparing RNA agent-loaded platelets disclosed herein, the methods further include acidifying the platelets, or pooled platelets, to a pH of about 6.0 to about 7.4, prior to a treating step disclosed herein. In some embodiments, the methods include acidifying the platelets to a pH of about 6.5 to about 6.9. In some embodiments, the methods include acidifying the platelets to a pH of about 6.6 to about 6.8. In some embodiments, the acidifying includes adding to the pooled platelets a solution comprising Acid Citrate Dextrose.

In some embodiments, the platelets are isolated prior to a treating step. In some embodiments, the methods further include isolating platelets by using centrifugation. In some embodiments, the centrifugation occurs at a relative centrifugal force (RCF) of about 800 g to about 2000 g. In some embodiments, the centrifugation occurs at relative centrifugal force (RCF) of about 1300 g to about 1800 g. In some embodiments, the centrifugation occurs at relative centrifugal force (RCF) of about 1500 g. In some embodiments, the centrifugation occurs for about 1 minute to about 60 minutes. In some embodiments, the centrifugation occurs for about 10 minutes to about 30 minutes. In some embodiments, the centrifugation occurs for about 20 minutes.

In some embodiments, the platelets are at a concentration from about 10,000 platelets/µl to about 500,000 platelets/µl. In some embodiments, the platelets are at a concentration from about 50,000 platelets/µl to about 500,000 platelets/µl. In some embodiments, the platelets are at a concentration from about 100,000 platelets/µl to about 400,000 platelets/µl. In some embodiments, the platelets are at a concentration of about 200,000 platelets/µl. In some embodiments, the platelets are at a concentration of about 2,000,000 platelets/µl.

In some embodiments, the buffer is a loading buffer comprising the components as listed in Table X herein. In some embodiments, the loading buffer includes one or more salts, such as phosphate salts, sodium salts, potassium salts, calcium salts, magnesium salts, and any other salt that can be found in blood or blood products. Exemplary salts include sodium chloride (NaCl), potassium chloride (KCL), and combinations thereof. In some embodiments, the loading buffer includes from about 0.5 mM to about 100 mM of the one or more salts. In some embodiments, the loading buffer includes from about 1 mM to about 100 mM (e.g., about 2 mM to about 90 mM, about 2 mM to about 6 mM, about 50 mM to about 100 mM, about 60 mM to about 90 mM, about 70 to about 85 mM) about of the one or more salts. In some embodiments, the loading buffer includes about 5 mM, about 75 mM, or about 80 mM of the one or more salts.

In some embodiments, the loading buffer includes one or more buffers, e.g., N-2-hydroxyethylpiperazine-N'-2-ethanesulfonic acid (HEPES), and/or sodium-bicarbonate (NaHCO$_3$). In some embodiments, the loading buffer includes from about 5 to about 100 mM of the one or more buffers. In some embodiments, the loading buffer includes from about 5 to about 50 mM (e.g., from about 5 mM to about 40 mM, from about 8 mM to about 30 mM, about 10 mM to about 25 mM) about of the one or more buffers. In some embodiments, the loading buffer includes about 10 mM, about 20 mM, about 25 mM, or about 30 mM of the one or more buffers.

In some embodiments, the loading buffer includes one or more saccharides, such as monosaccharides and disaccharides, including sucrose, maltose, trehalose, glucose, mannose, dextrose, and xylose. In some embodiments, the loading buffer includes from about 10 mM to about 1,000 mM of the one or more saccharides. In some embodiments, the loading buffer includes from about 50 to about 500 mM of the one or more saccharides. In embodiments, one or more saccharides is present in an amount of from 10 mM 10 to 500 mM. In some embodiments, one or more saccharides is present in an amount of from 50 mM to 200 mM. In embodiments, one or more saccharides is present in an amount from 100 mM to 150 mM.

In some embodiments, the loading buffer includes adding an organic solvent, such as ethanol, to the loading solution. In such a loading buffer, the solvent can range from about 0.1% (v/v) to about 5.0% (v/v), such as from about 0.3% (v/v) to about 3.0% (v/v), or from about 0.5% (v/v) to about 2% (v/v).

In some embodiments, the RNA agent includes one or more siRNAs.

In some embodiments, the RNA agent includes one or more miRNAs.

In some embodiments, the RNA agent includes one or more siRNAs and one or more miRNAs.

In some embodiments, the methods further include incubating the RNA agent in the presence of the loading buffer prior to the treatment step. In some embodiments, the methods further include incubating the loading buffer and a solution comprising the RNA agent and water at about 37° C. using different incubation periods. In some embodiments, the solution includes a concentration of about 0.1 nM to about 10 µM of the RNA agent. In some embodiments, the solution includes a concentration of about 1 nM to about 1 µM of the RNA agent. In some embodiments, the solution includes a concentration of about 10 nM to 10 µM of the RNA agent. In some embodiments, the solution includes a concentration of about 100 nM of the RNA agent. In some embodiments, the incubation of the RNA agent in the presence of the loading buffer is performed from about 1 minute to about 2 hours. In some embodiments, the incubation is performed at an incubation period of from about 5 minutes to about 1 hour. In some embodiments, the incubation is performed at an incubation period of from about 10 minutes to about 30 minutes. In some embodiments, the incubation is performed at an incubation period of about 20 minutes.

In some embodiments, the methods further include incubating the RNA agent in the presence of a cationic transfection reagent and the loading buffer prior to the treatment step. In some embodiments, the concentration of the cationic transfection reagent is from about 0.01% v/v to about 10% v/v. In some embodiments, the concentration of the cationic transfection reagent is from about 0.5% v/v to about 8% v/v. In some embodiments, the concentration of the cationic transfection reagent is from about 1% v/v to about 5% v/v. In some embodiments, the concentration of the cationic transfection reagent is from about 2% v/v to about 3% v/v.

In some embodiments, the methods further include mixing the platelets and the complexed cationic lipid and RNA agent (cationic lipid-RNA agent) in the presence of the loading buffer at 22° C., using a platelet to cationic lipid- RNA agent volume ratio of 1:1. In some embodiments, the cationic lipid is lipofectamine. In some embodiments, the methods further include incubating the platelets and the cationic lipid-RNA agent in the presence of the loading buffer at 22° C. using a platelet to cationic lipid-RNA agent volume ratio of 1:1, using different incubation periods. In some embodiments, the incubation is performed at an incubation period of from about 5 minutes to about 12 hours. In some embodiments, the incubation is performed at an incubation period of from about 10 minutes to about 6 hours. In some embodiments, the incubation is performed at an incubation period of from about 15 minutes to about 3 hours. In some embodiments, the incubation is performed at an incubation period of about 2 hours. In some embodiments, the final product includes platelets and the cationic lipid-RNA agent at a volume ratio of 1:1, with a range in volume ratio of about 1 to about 50.

In some embodiments, the concentration of RNA agent in the RNA agent-loaded platelets is from about 0.1 nM to about 10 μM. In some embodiments, the concentration of RNA agent in the RNA agent-loaded platelets is from about 1 nM to about 1 μM. In some embodiments, the concentration of RNA agent in the RNA agent-loaded platelets is from about 10 nM to 10 μM. In some embodiments, the concentration of RNA agent in the RNA-loaded platelets is about 100 nM.

In some embodiments, the methods further include drying the RNA agent-loaded platelets. In some embodiments, the drying step includes freeze-drying the RNA agent-loaded platelets. In some embodiments, the methods further include rehydrating the RNA agent-loaded platelets obtained from the drying step.

In some embodiments, RNA agent-loaded platelets are prepared by using any of the variety of methods provided herein.

In some embodiments, rehydrated RNA agent-loaded platelets are prepared by any one method comprising rehydrating the RNA agent-loaded platelets provided herein.

The RNA agent-loaded platelets may be used, for example, in therapeutic applications as disclosed herein. Additionally or alternatively, the RNA agent-loaded platelets may be employed in functional assays. In some embodiments, the RNA agent-loaded platelets are cold stored, cryopreserved, or lyophilized (to produce thrombosomes) prior to use in therapy or in functional assays.

Any known technique for drying platelets can be used in accordance with the present disclosure, as long as the technique can achieve a final residual moisture content of less than 5%. Preferably, the technique achieves a final residual moisture content of less than 2%, such as 1%, 0.5%, or 0.1%. Non-limiting examples of suitable techniques are freeze-drying (lyophilization) and spray-drying. A suitable lyophilization method is presented in Table A. Additional exemplary lyophilization methods can be found in U.S. Pat. Nos. 7,811,558, 8,486,617, and 8,097,403. An exemplary spray-drying method includes: combining nitrogen, as a drying gas, with a loading buffer according to the present disclosure, then introducing the mixture into GEA Mobile Minor spray dryer from GEA Processing Engineering, Inc. (Columbia MD, USA), which has a Two-Fluid Nozzle configuration, spray drying the mixture at an inlet temperature in the range of 150° C. to 190° C., an outlet temperature in the range of 65° C. to 100° C., an atomic rate in the range of 0.5 to 2.0 bars, an atomic rate in the range of 5 to 13 kg/hr, a nitrogen use in the range of 60 to 100 kg/hr, and a run time of 10 to 35 minutes. The final step in spray drying is preferentially collecting the dried mixture. The dried composition in some embodiments is stable for at least six months at temperatures that range from −20° C. or lower to 90° C. or higher.

TABLE A

Exemplary Lyophilization Protocol

| | Step | Temp. Set | Type | Duration | Pressure Set |
|---|---|---|---|---|---|
| FreezingStep | F1 | −50° C. | Ramp | Var | N/A |
| | F2 | −50° C. | Hold | 3 Hrs | N/A |
| Vacuum Pulldown | F3 | −50° | Hold | Var | N/A |
| Primary Dry | P1 | −40° | Hold | 1.5 Hrs | 0 mT |
| | P2 | −35° | Ramp | 2 Hrs | 0 mT |
| | P3 | −25° | Ramp | 2 Hrs | 0 mT |
| | P4 | −17° C. | Ramp | 2 Hrs | 0 mT |
| | P5 | 0° C. | Ramp | 1.5 Hrs | 0 mT |
| | P6 | 27° C. | Ramp | 1.5 Hrs | 0 mT |
| | P7 | 27° C. | Hold | 16 Hrs | 0 mT |
| Secondary Dry | S1 | 27° C. | Hold | >8 Hrs | 0 mT |

In some embodiments, the step of drying the RNA agent-loaded platelets that are obtained as disclosed herein, such as the step of freeze-drying the RNA agent-loaded platelets that are obtained as disclosed herein, includes incubating the platelets with a lyophilizing agent. In some embodiments, the lyophilizing agent is polysucrose. In some embodiments, the lyophilizing agent is a non-reducing disaccharide. Accordingly, in some embodiments, the methods for preparing RNA agent-loaded platelets further include incubating the RNA agent-loaded platelets with a lyophilizing agent. In some embodiments, the lyophilizing agent is a saccharide. In some embodiments, the saccharide is a disaccharide, such as a non-reducing disaccharide.

In some embodiments, the platelets are incubated with a lyophilizing agent for a sufficient amount of time and at a suitable temperature to load the platelets with the lyophilizing agent. Non-limiting examples of suitable lyophilizing agents are saccharides, such as monosaccharides and disaccharides, including sucrose, maltose, trehalose, glucose (e.g., dextrose), mannose, and xylose. In some embodiments, non-limiting examples of lyophilizing agent include serum albumin, dextran, polyvinyl pyrrolidone (PVP), starch, and hydroxyethyl starch (HES). In some embodiments, exemplary lyophilizing agents can include a high molecular weight polymer, into the loading composition. By "high molecular weight" it is meant a polymer having an average molecular weight of about or above 70 kDa. Non-limiting examples are polymers of sucrose and epichlorohydrin. In some embodiments, the lyophilizing agent is polysucrose. Although any amount of high molecular weight polymer can be used as a lyophilizing agent, it is preferred that an amount be used that achieves a final concentration of about 3% to 10% (w/v), such as 3% to 7%, for example 6%.

In some embodiments, the process for preparing a composition includes adding an organic solvent, such as ethanol, to the loading solution. In such a loading solution, the solvent can range from 0.1% to 5.0% (v/v).

Within the process provided herein for making the compositions provided herein, addition of the lyophilizing agent can be the last step prior to drying. However, in some embodiments, the lyophilizing agent is added at the same time or before the RNA agent, the cryoprotectant, or other components of the loading composition. In some embodiments, the lyophilizing agent is added to the loading solution, thoroughly mixed to form a drying solution, dispensed into a drying vessel (e.g., a glass or plastic serum vial, a lyophilization bag), and subjected to conditions that allow for drying of the solution to form a dried composition.

An exemplary saccharide for use in the compositions disclosed herein is trehalose. Regardless of the identity of the saccharide, it can be present in the composition in any suitable amount. For example, it can be present in an amount of 1 mM to 1 M. In embodiments, it is present in an amount of from 10 mM 10 to 500 mM. In some embodiments, it is present in an amount of from 20 mM to 200 mM. In embodiments, it is present in an amount from 40 mM to 100 mM. In various embodiments, the saccharide is present in different specific concentrations within the ranges recited above, and one of skill in the art can immediately understand the various concentrations without the need to specifically recite each herein. Where more than one saccharide is present in the composition, each saccharide can be present in an amount according to the ranges and particular concentrations recited above.

The step of incubating the platelets to load them with a cryoprotectant or as a lyophilizing agent includes incubating the platelets for a time suitable for loading, as long as the time, taken in conjunction with the temperature, is sufficient for the cryoprotectant or lyophilizing agent to come into contact with the platelets and, preferably, be incorporated, at least to some extent, into the platelets. In embodiments, incubation is carried out for about 1 minute to about 180 minutes or longer.

The step of incubating the platelets to load them with a cryoprotectant or lyophilizing agent includes incubating the platelets and the cryoprotectant at a temperature that, when selected in conjunction with the amount of time allotted for loading, is suitable for loading. In general, the composition is incubated at a temperature above freezing for at least a sufficient time for the cryoprotectant or lyophilizing agent to come into contact with the platelets. In embodiments, incubation is conducted at 37° C. In certain embodiments, incubation is performed at 20° C. to 42° C. For example, in embodiments, incubation is performed at 35° C. to 40° C. (e.g., 37° C.) for 110 to 130 (e.g., 120) minutes.

In various embodiments, the bag is a gas-permeable bag configured to allow gases to pass through at least a portion or all portions of the bag during the processing. The gas-permeable bag can allow for the exchange of gas within the interior of the bag with atmospheric gas present in the surrounding environment. The gas-permeable bag can be permeable to gases, such as oxygen, nitrogen, water, air, hydrogen, and carbon dioxide, allowing gas exchange to occur in the compositions provided herein. In some embodiments, the gas-permeable bag allows for the removal of some of the carbon dioxide present within an interior of the bag by allowing the carbon dioxide to permeate through its wall. In some embodiments, the release of carbon dioxide from the bag can be advantageous to maintaining a desired pH level of the composition contained within the bag.

In some embodiments, the container of the process herein is a gas-permeable container that is closed or sealed. In some embodiments, the container is a container that is closed or sealed and a portion of which is gas-permeable. In some embodiments, the surface area of a gas-permeable portion of a closed or sealed container (e.g., bag) relative to the volume of the product being contained in the container (hereinafter referred to as the "SA/V ratio") can be adjusted to improve pH maintenance of the compositions provided herein. For example, in some embodiments, the SA/V ratio of the container can be at least about 2.0 mL/cm$^2$ (e.g., at least about 2.1 mL/cm$^2$, at least about 2.2 mL/cm$^2$, at least about 2.3 mL/cm$^2$, at least about 2.4 mL/cm$^2$, at least about 2.5 mL/cm$^2$, at least about 2.6 mL/cm$^2$, at least about 2.7 mL/cm$^2$, at least about 2.8 mL/cm$^2$, at least about 2.9 mL/cm$^2$, at least about 3.0 mL/cm$^2$, at least about 3.1 mL/cm$^2$, at least about 3.2 mL/cm$^2$, at least about 3.3 mL/cm$^2$, at least about 3.4 mL/cm$^2$, at least about 3.5 mL/cm$^2$, at least about 3.6 mL/cm$^2$, at least about 3.7 mL/cm$^2$, at least about 3.8 mL/cm$^2$, at least about 3.9 mL/cm$^2$, at least about 4.0 mL/cm$^2$, at least about 4.1 mL/cm$^2$, at least about 4.2 mL/cm$^2$, at least about 4.3 mL/cm$^2$, at least about 4.4 mL/cm$^2$, at least about 4.5 mL/cm$^2$, at least about 4.6 mL/cm$^2$, at least about 4.7 mL/cm$^2$, at least about 4.8 mL/cm$^2$, at least about 4.9 mL/cm$^2$, or at least about 5.0 mL/cm 2. In some embodiments, the SA/V ratio of the container can be at most about 10.0 mL/cm$^2$ (e.g., at most about 9.9 mL/cm$^2$, at most about 9.8 mL/cm$^2$, at most about 9.7 mL/cm$^2$, at most about 9.6 mL/cm$^2$, at most about 9.5 mL/cm$^2$, at most about 9.4 mL/cm$^2$, at most about 9.3 mL/cm$^2$, at most about 9.2 mL/cm$^2$, at most about 9.1 mL/cm$^2$, at most about 9.0 mL/cm$^2$, at most about 8.9 mL/cm$^2$, at most about 8.8 mL/cm$^2$, at most about 8.7 mL/cm$^2$, at most about 8.6, mL/cm$^2$ at most about 8.5 mL/cm$^2$, at most about 8.4 mL/cm$^2$, at most about 8.3 mL/cm$^2$, at most about 8.2 mL/cm$^2$, at most about 8.1 mL/cm$^2$, at most about 8.0 mL/cm$^2$, at most about 7.9 mL/cm$^2$, at most about 7.8 mL/cm$^2$, at most about 7.7 mL/cm$^2$, at most about 7.6 mL/cm$^2$, at most about 7.5 mL/cm$^2$, at most about 7.4 mL/cm$^2$, at most about 7.3 mL/cm$^2$, at most about 7.2 mL/cm$^2$, at most about 7.1 mL/cm$^2$, at most about 6.9 mL/cm$^2$, at most about 6.8 mL/cm$^2$, at most about 6.7 mL/cm$^2$, at most about 6.6 mL/cm$^2$, at most about 6.5 mL/cm$^2$, at most about 6.4 mL/cm$^2$, at most about 6.3 mL/cm$^2$, at most about 6.2 mL/cm$^2$, at most about 6.1 mL/cm$^2$, at most about 6.0 mL/cm$^2$, at most about 5.9 mL/cm$^2$, at most about 5.8 mL/cm$^2$, at most about 5.7 mL/cm$^2$, at most about 5.6 mL/cm$^2$, at most about 5.5 mL/cm$^2$, at most about 5.4 mL/cm$^2$, at most about 5.3 mL/cm$^2$, at most about 5.2 mL/cm$^2$, at most about 5.1 mL/cm$^2$, at most about 5.0 mL/cm$^2$, at most about 4.9 mL/cm$^2$, at most about 4.8 mL/cm$^2$, at most about 4.7 mL/cm$^2$, at most about 4.6 mL/cm$^2$, at most about 4.5 mL/cm$^2$, at most about 4.4 mL/cm$^2$, at most about 4.3 mL/cm$^2$, at most about 4.2 mL/cm$^2$, at most about 4.1 mL/cm$^2$, or at most about 4.0 mL/cm$^2$. In some embodiments, the SA/V ratio of the container can range from about 2.0 to about 10.0 mL/cm$^2$ (e.g., from about 2.1 mL/cm$^2$ to about 9.9 mL/cm$^2$, from about 2.2 mL/cm$^2$ to about 9.8 mL/cm$^2$, from about 2.3 mL/cm$^2$ to about 9.7 mL/cm$^2$, from about 2.4 mL/cm$^2$ to about 9.6 mL/cm$^2$, from about 2.5 mL/cm$^2$ to about 9.5 mL/cm$^2$, from about 2.6 mL/cm$^2$ to about 9.4 mL/cm$^2$, from about 2.7 mL/cm$^2$ to about 9.3 mL/cm$^2$, from about 2.8 mL/cm$^2$ to about 9.2 mL/cm$^2$, from about 2.9 mL/cm$^2$ to about 9.1 mL/cm$^2$, from about 3.0 mL/cm$^2$ to about 9.0 mL/cm$^2$, from about 3.1 mL/cm$^2$ to about 8.9 mL/cm$^2$, from about 3.2 mL/cm$^2$ to about 8.8 mL/cm$^2$, from about 3.3 mL/cm$^2$ to about 8.7 mL/cm$^2$, from about 3.4 mL/cm$^2$ to about 8.6 mL/cm$^2$, from about 3.5 mL/cm$^2$ to about 8.5 mL/cm$^2$, from about 3.6 mL/cm$^2$ to about 8.4 mL/cm$^2$, from about 3.7 mL/cm$^2$ to about 8.3 mL/cm$^2$, from about 3.8 mL/cm$^2$ to about 8.2 mL/cm$^2$, from about 3.9 mL/cm$^2$ to about 8.1 mL/cm$^2$, from about 4.0 mL/cm$^2$ to about 8.0 mL/cm$^2$, from about 4.1 mL/cm$^2$ to about 7.9 mL/cm$^2$, from about 4.2 mL/cm$^2$ to about 7.8 mL/cm$^2$, from about 4.3 mL/cm$^2$ to about 7.7 mL/cm$^2$, from about 4.4 mL/cm$^2$ to about 7.6 mL/cm$^2$, from about 4.5 mL/cm$^2$ to about 7.5 mL/cm$^2$, from about 4.6 mL/cm$^2$ to about 7.4 mL/cm$^2$, from about 4.7 mL/cm$^2$ to about 7.3 mL/cm², from about 4.8 mL/cm² to about 7.2 mL/cm², from about 4.9 mL/cm² to about 7.1 mL/cm², from about 5.0 mL/cm² to about 6.9 mL/cm², from about 5.1 mL/cm² to about 6.8 mL/cm², from about 5.2 mL/cm² to about 6.7 mL/cm², from about 5.3 mL/cm² to about 6.6 mL/cm², from about 5.4 mL/cm² to about 6.5 mL/cm², from about 5.5 mL/cm² to about 6.4 mL/cm², from about 5.6 mL/cm² to about 6.3 mL/cm², from about 5.7 mL/cm² to about 6.2 mL/cm², or from about 5.8 mL/cm² to about 6.1 mL/cm².

Gas-permeable closed containers (e.g., bags) or portions thereof can be made of one or more various gas-permeable materials. In some embodiments, the gas-permeable bag can be made of one or more polymers including fluoropolymers (such as polytetrafluoroethylene (PTFE) and perfluoroalkoxy (PFA) polymers), polyolefins (such as low-density polyethylene (LDPE), high-density polyethylene (HDPE)), fluorinated ethylene propylene (FEP), polystyrene, polyvinylchloride (PVC), silicone, and any combinations thereof.

In some embodiments, the lyophilizing agent as disclosed herein may be a high molecular weight polymer. By "high molecular weight" it is meant a polymer having an average molecular weight of about or above 70 kDa and up to 1,000,000 kDa. Non-limiting examples are polymers of sucrose and epichlorohydrin (polysucrose). Although any amount of high molecular weight polymer can be used, it is preferred that an amount be used that achieves a final concentration of about 3% to 10% (w/v), such as 3% to 7%, for example 6%. Other non-limiting examples of lyoprotectants are serum albumin, dextran, polyvinyl pyrrolidone (PVP), starch, and hydroxyethyl starch (HES).

In some embodiments, the loading buffer includes an organic solvent, such as an alcohol (e.g., ethanol). In such a loading buffer, the amount of solvent can range from 0.1% to 5.0% (v/v).

In some embodiments, the RNA agent-loaded platelets prepared as disclosed herein have a storage stability that is at least about equal to that of the platelets prior to the loading of the RNA agent.

In some embodiments, the RNA agent-loaded platelets incubated with a lyophilizing agent as described herein retain at least about 90% of the RNA agent, such as at least about 95% of the RNA agent, such as at least about 99% of the RNA agent, after storage. In some embodiments, the RNA agent-loaded platelets incubated with a lyophilizing agent as described herein retain at least about 90% of the RNA agent, such as at least about 95% of the RNA agent, such as at least about 99% of the RNA agent, after storage at low temperature, such as a temperature of about −20° C. or lower, such as a temperature of about −80° C. In some embodiments, the RNA agent-loaded platelets incubated with a lyophilizing agent as described herein retain at least about 90% of the RNA agent, such as at least about 95% of the RNA agent, such as at least about 99% of the RNA agent, after storage at low temperature, such as a temperature of about −20° C. or lower, such as a temperature of about −80° C., for a period of at least three days, such as at least one week, such as at least one month, such as at least three months, such as at least six months. In some embodiments, the RNA agent-loaded platelets incubated with a lyophilizing agent as described herein retain at least about 90% of channel occlusion in a T-TAS (Total Thrombus-formation Analysis System) analysis, such as at least about 95% of channel occlusion in a T-TAS analysis, such as at least about 99% of channel occlusion in a T-TAS analysis, after storage. In some embodiments, the RNA agent-loaded platelets incubated with a lyophilizing agent as described herein retain at least about 90% of channel occlusion in a T-TAS (Total Thrombus-formation Analysis System) analysis, such as at least about 95% of channel occlusion in a T-TAS analysis, such as at least about 99% of channel occlusion in a T-TAS analysis, after storage at low temperature, such as a temperature of about −20° C. or lower, such as a temperature of about −80° C. In some embodiments, the RNA agent-loaded platelets incubated with a lyophilizing agent as described herein retain at least about 90% of channel occlusion in a T-TAS (Total Thrombus-formation Analysis System) analysis, such as at least about 95% of channel occlusion in a T-TAS analysis, such as at least about 99% of channel occlusion in a T-TAS analysis, after storage at low temperature, such as a temperature of about −20° C. or lower, such as a temperature of about −80° C., for a period of at least three days, such as at least one week, such as at least one month, such as at least three months, such as at least six months.

The loading buffer may be any buffer that is non-toxic to the platelets and provides adequate buffering capacity to the solution at the temperatures at which the solution will be exposed during the process provided herein. Thus, the buffer may include any of the known biologically compatible buffers available commercially, such as phosphate buffers, such as phosphate buffered saline (PBS), bicarbonate/carbonic acid, such as sodium-bicarbonate buffer, N-2-hydroxyethylpiperazine-N'-2-ethanesulfonic acid (HEPES), and tris-based buffers, such as tris-buffered saline (TBS). Likewise, it may include one or more of the following buffers: propane-1,2,3-tricarboxylic (tricarballylic); benzenepentacarboxylic; maleic; 2,2-dimethyl succinic; EDTA; 3,3-dimethylglutaric; bis(2-hydroxyethyl)imino-tris(hydroxymethyl)-methane (BIS-TRIS); benzenehexacarboxylic (mellitic); N-(2-acetamido)imino-diacetic acid (ADA); butane-1,2,3,4-tetracarboxylic; pyrophosphoric; 1,1-cyclopentanediacetic (3,3 tetramethylene-glutaric acid); piperazine-1,4-bis-(2-ethanesulfonic acid) (PIPES); N-(2-acetamido)-2-amnoethanesulfonic acid (ACES); 1,1-cyclohexanediacetic; 3,6-endomethylene-1,2,3,6-tetrahydrophthalic acid (EMTA; ENDCA); imidazole; 2-(aminoethyl)trimethylammonium chloride (CHOLAMINE); N,N-bis(2-hydroxyethyl)-2-aminoethanesulfonic acid (BES); 2-methylpropane-1,2,3-triscarboxylic (beta-methyltricarballylic); 2-(N-morpholino)propanesulfonic acid (MOPS); phosphoric; and N-tris(hydroxymethyl)methyl-2-amminoethane sulfonic acid (TES).

Flow cytometry can be used to obtain a relative quantification of loading efficiency by measuring the mean fluorescence intensity of the RNA agent in the RNA agent-loaded platelets. Platelets can be evaluated for functionality by adenosine diphosphate (ADP), collagen, arachidonic acid, and/or thrombin receptor activating peptide (TRAP) stimulation post-loading.

In some embodiments, the RNA agent-loaded platelets are lyophilized. In some embodiments, the RNA agent-loaded platelets are cryopreserved.

In some embodiments, the RNA agent-loaded platelets retain the loaded RNA agent upon rehydration and release the RNA agent upon stimulation by endogenous platelet activators.

In some embodiments, the dried platelets (such as freeze-dried platelets) retain the loaded RNA agent upon rehydration and release the RNA agent upon stimulation by endogenous platelet activators. In some embodiments, at least about 10%, such as at least about 20%, such as at least about 30% of the RNA agent is retained. In some embodiments, from about 10% to about 20%, such as from about 20% to about 30% of the RNA agent is retained.

Examples of a RNA agents that may be loaded in a platelet include, but are not limited to, BLOCK-iT™ fluorescent oligo and siGLO green transfection indicator.

Various agents and/or procedures may be used to load the platelets with a RNA agent. In some embodiments, the platelets are loaded with a RNA agent previously incubated with a cationic lipid such as, without limitation, lipofectamine.

In some embodiments, the platelets are loaded by a process comprising electroporation.

In some embodiments, the platelets are loaded by a process comprising transduction.

In some embodiments, the platelets are loaded by a process comprising osmotic hypertonic/hypotonic loading.

Exemplary protocols that employ the foregoing agents or procedures are shown below:

Lipofectamine Transfection

Background

Lipofectamine is a cationic lipid; the Lipofectamine positively charged head group interacts with the negatively charged phosphate backbone of nucleic acids to facilitate transfection. Cellular internalization of the nucleic acid is achieved by incubating cells with the complexed Lipofectamine and nucleic acid.

Protocol

Prepare the Lipofectamine and RNA agent in aqueous buffer at room temperature. Incubate the complexed Lipofectamine and RNA agent with platelets for 2-3 hours. Transfected platelets may be lyophilized to create Thrombosomes. Fluorescently labeled RNA agent can be detected via flow cytometry and visualized using fluorescence microscopy. This method of loading is applicable to both siRNA and miRNA.

Background

Saponin is a detergent which can be used, under optimal concentration, to remove cholesterol from cell membrane and thereby increase the permeability of plasma membranes. Cells treated with saponin are permeable to molecules that would otherwise be excluded by the plasma membrane.

Protocol

Incubate platelets with 1-20 µg/ml of saponin at 37° C. to permeabilize platelet cell membranes. Incubate saponin permeabilized platelets with RNA agent at 37° C. for 2-4 hours to allow for loading. Loaded platelets may be lyophilized to make Thrombosomes. RNA agent can be detected using flow cytometry or fluorescence microscopy if fluorescently tagged. In order to confirm that saponin treatment permeabilized platelet membrane, stimulate platelets with inositol 1, 4, 5-triphosphate (IP3). IP3 stimulation of platelets lead to a cascade of reactions that generate phosphorylated substrates for protein kinase C, and this ultimately leads to release of 5-HT from dense granules.

Electroporation

Background

An electroporation machine generates electrical pulses which facilitate formation of transient openings in plasma membranes. The increased plasma membrane permeability allows entry of large and/or charged RNA agent that would otherwise not enter the cell due to membrane barrier.

Protocol

Perform electroporation of platelets in the presence of desired RNA agent. RNA agents of interest can be detected by flow cytometry and fluorescence microscopy if they are fluorescently tagged.

Osmotic Hypertonic/Hypotonic Loading

Background

The influx cell loading strategy harnesses osmosis to load cells with water soluble, polar compounds. Cells are initially placed in a hypertonic solution containing RNA agent of interest. In this hypertonic solution, water will move out of the cell into solution while RNA agent will move into the cell via pinocytosis. Following that, cells are placed in a hypotonic solution in which water will enter the cell, lysing the pinocytic vesicles and thereby releasing RNA agent into the cytosol.

Protocol

Incubate platelets in hypertonic loading medium containing RNA agent compound at 37° C. for at least 1 hour. Isolate loaded platelets from solution via centrifugation, resuspend platelets in hypotonic lysis medium, and incubate at 37° C. Pinocytic vesicles will burst and release RNA agent into the cytosol. Fluorescently labeled RNA agent can be visualized using fluorescence microscopy to confirm internalization. Flow cytometry may be performed to quantify RNA agent load per cell for fluorescent RNA agent.

In some embodiments, RNA agent-loaded platelets, RNA agent-loaded platelet derivatives, or RNA agent-loaded thrombosomes may shield the RNA agent from exposure in circulation, thereby reducing or eliminating systemic toxicity (e.g. cardiotoxicity) associated with the RNA agent. In some embodiments, RNA agent-loaded platelets, RNA agent-loaded platelet derivatives, or RNA agent-loaded thrombosomes may also protect the RNA agent from metabolic degradation or inactivation. In some embodiments, RNA agent delivery with RNA agent-loaded platelets, RNA agent-loaded platelet derivatives, or RNA agent-loaded thrombosomes may therefore be advantageous in treatment of diseases such as cancer, since RNA agent-loaded platelets, RNA agent-loaded platelet derivatives, or RNA agent-loaded thrombosomes facilitate targeting of cancer cells while mitigating systemic side effects. In some embodiments, RNA agent-loaded platelets, RNA agent-loaded platelet derivatives, or RNA agent-loaded thrombosomes may be used in any therapeutic setting in which expedited healing process is required or advantageous.

In some embodiments, provided herein is a method of treating a disease as disclosed herein, comprising administering RNA agent-loaded platelets, RNA agent-loaded platelet derivatives, or RNA agent-loaded thrombosomes as disclosed herein. In some embodiments, provided herein is a method of treating a disease as disclosed herein, comprising administering cold stored, room temperature stored, cryopreserved thawed, rehydrated, and/or lyophilized platelets, platelet derivatives, or thrombosomes as disclosed herein. In some embodiments, the disease is cancer. In some embodiments, the disease is Traumatic Brain injury. In some embodiments, the disease is idiopathic thrombocytomenic purpura (ITP). In some embodiments, the disease is thrombotic thrombocytopenic purpura (TTP). In some embodiments, the disease is hemophilia. In some embodiments, the disease is an inherited disorder. In some embodiments, the disease is heart disease. In some embodiments, the disease is kidney disease. In some embodiments, the disease is a nervous system development disease. In some embodiments, the disease is hemostasis. In some embodiments, the disease is obesity.

Examples of diseases (therapeutic indications) that may be treated with the RNA agent-loaded platelets are as follows:

Therapeutic Indications
Acute lymphoblastic leukemia (ALL)
Acute myeloid leukemia (AML)
Breast cancer (can also be used as an adjuvant therapy for metastasized breast cancer post surgery)
Gastric cancer
Hodgkin lymphoma
Neuroblastoma
Non-Hodgkin lymphoma
Ovarian cancer
Cervical cancer
Small cell lung cancer
Non-small cell lung cancer (NSCLC)
Soft tissue and bone sarcomas
Thyroid cancer
Transitional cell bladder cancer
Wilms tumor
Neuroendocrine tumors
Pancreatic cancer
Multiple myeloma
Renal cancer
Glioblastoma
Prostate cancer
Sarcoma
Colon cancer
Melanoma
Colitis
Chronic inflammatory demyelinating polyneuropathy
Guillain-Barre syndrome
Immune Thrombocytopenia
Kawasaki disease
Lupus
Multiple Sclerosis
Myasthenia gravis
Myositis
Angioplasty clot prevention
Crohn's
Burns (>30% body surface area, after first 24 hours)
Asthma
Cirrhosis with refractory ascites
Haemorrhagic shock (when patient not responsive to crystalloids/colloids)
Hepatorenal syndrome (used in combination with vasoconstrictive drugs)
Nephrotic syndrome (for patient with albumin<2 g/dL with hypovolemia and/or pulmonary edema)
Organ transplantation
Paracentesis
Hypovolemia
Aneurysms
Atherosclerosis
Cancer
Cardiovascular diseases (post-myocardial infarction remodeling, cardiac regeneration, cardiac fibrosis, viral myocarditis, cardiac hypertrophy, pathological cardiac remodeling)
Genetic disorders
Metabolic diseases
Neoangiogenesis
Opthalmic conditions (retinal angiogenesis, ocular hypertension, glaucoma, diabetic macular edema, diabetic retinopathy, macular degeneration)
Hypercholesterolemia
Pulmonary hypertension Examples of RNA agent and therapeutic indications for RNA agent(s) to be loaded into platelets are as follows:

| RNA Agent | Therapeutic indications |
|---|---|
| miRNA and/or siRNA | Aneurysms |
| | Atherosclerosis |
| | Cancer |
| | Cardiovascular diseases (post - myocardial infarction remodeling, cardiac regeneration, cardiac fibrosis, viral myocarditis, cardiac hypertrophy, pathological cardiac remodeling) |
| | Genetic disorders |
| | Infectious diseases |
| | Metabolic diseases |
| | Neoangiogenesis |
| | Opthalmic conditions (retinal angiogenesis) |
| | Pulmonary hypertension |

In some embodiments, incubation is performed at 22° C. using a platelet to cationic lipid-RNA agent volume ratio of 1:1, using different incubation periods.

While the embodiments of the invention are amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

Example 1 siRNA-Loaded Platelets

Stored and fresh platelets were used to test siRNA loading. Stored platelets were collected via the apheresis method in an acid-citrate-dextrose (ACD) solution and stored in blood bags for 24 hours before use. Fresh platelets were collected on the day-of-use in an ACD solution in BD Vacutainer® tubes and isolated from whole blood by centrifugal blood fractionation.

A FITC-conjugated siRNA control (BLOCK-iT™ Fluorescent Oligo, ThermoSci Cat. # 2013) was used to assay siRNA-loading in both stored and fresh platelets. The siRNA was loaded into the platelets using a cationic lipid transfection agent (Lipofectamine™ RNAiMAX, ThermoSci) in FIBS buffer (Table 1).

Liquid transfection media conditions were tested to assay siRNA-loading. Four different liquid transfection media conditions were tested on fresh platelets: Loading Buffer (Table 2), Loading Buffer without ethanol (Table 3), HEPES-buffered Tyrode's solution (HMTA, Table 4), and Opti-MEM™ (ThermoSci, commonly used cell growth and transfection medium). Stored platelets were tested with Loading Buffer supplemented with or without Opti-MEM™ (Table 5). The components of each buffer are shown in their respective tables. The siRNA-loaded platelets were prepared by incubating either the stored or fresh platelets with the BLOCK-iT™ Fluorescent Oligo (0.377 µM) and cationic transfection reagent (0.24% v/v) in one of the indicated buffers. Protocol 1 (described below) was used, except where otherwise indicated.

The platelet concentration in the various liquid transfection media conditions was $6.35 \times 10^7$ platelets/mL.

TABLE 1

| HBS: | |
|---|---|
| Component | Concentration (mg/mL) |
| NaCl | 8.77 |
| HEPES | 2.38 |
| pH | 6.6-6.8 |

TABLE 2

| Loading Buffer: | |
|---|---|
| Component | Concentration (mg/mL, except where otherwise indicated) |
| NaCl | 4.38 |
| KCl | 0.36 |
| HEPES | 2.26 |
| NaHCO₃ | 1.01 |
| Dextrose | 0.54 |
| Trehalose | 34.23 |
| Ethanol | 1.00% (v/v) |
| pH | 6.6-6.8 |

TABLE 3

| Loading Buffer without ethanol: | |
|---|---|
| Component | Concentration (mg/mL, except where otherwise indicated) |
| NaCl | 4.38 |
| KCl | 0.36 |
| HEPES | 2.26 |
| NaHCO₃ | 1.01 |
| Dextrose | 0.54 |
| Trehalose | 34.23 |
| pH | 6.6-6.8 |

TABLE 4

| HTMA: | |
|---|---|
| Component | Concentration (mM, except where otherwise indicated) |
| CaCl$_2$ | 1.8 |
| MgCl$_2$ | 1.1 |
| KCl | 2.7 |
| NaCl | 137 |
| NaH$_2$PO$_4$ | 0.4 |
| HEPES | 10 |
| D-glucose | 5.6 |
| pH | 6.5 |

TABLE 5

| Loading Buffer with Opti-MEM ™: | |
|---|---|
| Component | Concentration (mg/mL, except where otherwise indicated) |
| NaCl | 4.38 |
| KCl | 0.36 |
| HEPES | 2.26 |
| NaHCO$_3$ | 1.01 |
| Dextrose | 0.54 |
| Trehalose | 34.23 |
| Ethanol | 1.00% (v/v) |
| Opti-MEM ™ | 24% (v/v) |
| pH | 6.6-6.8 | siRNA-loading for fresh and stored platelets was evaluated by flow cytometry to obtain a relative quantification of loading efficiency as well as a geometric mean fluorescence intensity (gMFI) of the BLOCK-iT™ Fluorescent Oligo in siRNA-loaded platelets in each buffer condition specified in the figures.

Figure 2:
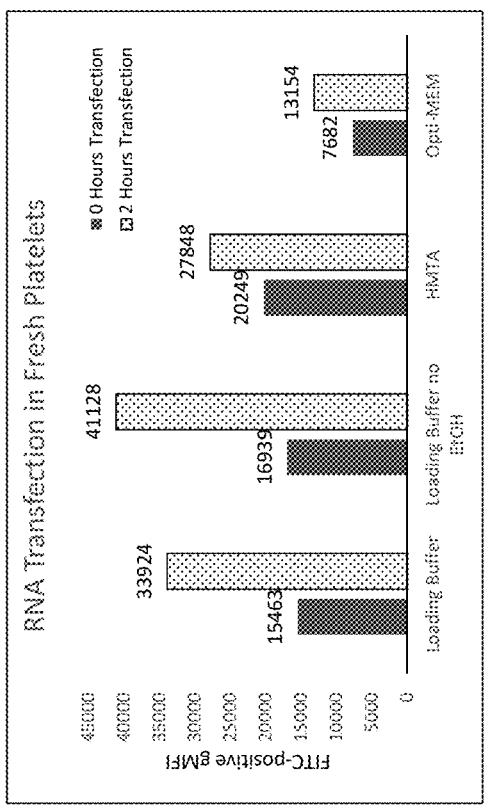
FIG. 2 shows geometric mean fluorescence intensity of fresh platelets incubated in different liquid transfection media containing fluorescent siRNA. HMTA=HEPES-buffered Tryode's Solution. Opti-MEM=Opti-MEM™ (ThermoSci). EtOH=Ethanol.

A comparison of fresh platelets incubated for two hours, at room temperature, in different liquid transfection media conditions is depicted in FIG. 1. Transfection efficiency, as a percentage of FITC-positive platelet events by flow cytometry was similar in all conditions at two hours, though an uptake of fluorescent siRNA appeared to occur more rapidly in Loading Buffer (with and without ethanol) than in HMTA or Opti-MEM™. Fluorescence intensity (gMFI) of platelet events positive for fluorescent siRNA was greater in Loading Buffer (with and without ethanol) than when platelets were incubated in HMTA or Opti-MEM™, as shown in FIG. 2. A higher gMFI suggests a greater copy number of fluorescent siRNAs was incorporated into the platelets when the Loading Buffer was used as the liquid transfection medium. N=1.

Figure 3:
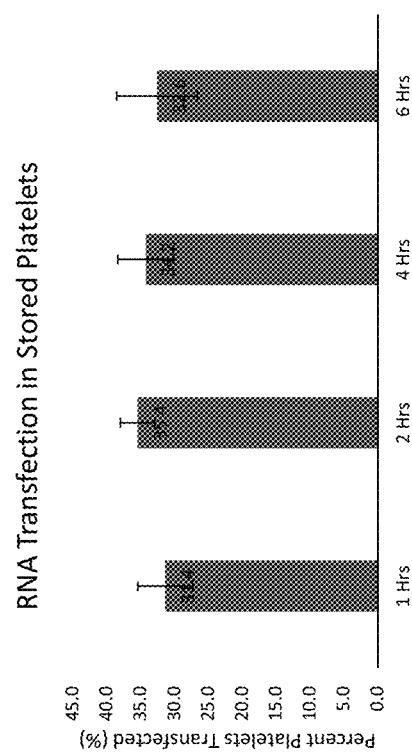
FIG. 3 shows percent transfection of stored platelets incubated in liquid transfection media containing fluorescent siRNA at different time points indicated on the X axis.

Transfection efficiency for stored platelets was evaluated over the course of six hours by flow cytometry, as shown in FIG. 3. The stored platelets were incubated at room temperature, for the indicated times, in Loading Buffer supplemented with Opti-MEM™ at room temperature. The percentage of platelet events that were positive for fluorescent siRNA reached a maximum at two hours. N=2. Error bars indicate standard deviation (SD). The percentage of fluorescent siRNA-positive platelet events was greater for stored platelets as compared to fresh platelets (see 10.2% shown in FIG. 1 compared to 35.4% shown in FIG. 3). Stored platelets were also incubated in Loading Buffer alone, without Opti-MEM™, at room temperature. The percentage of platelet events that were positive for fluorescent siRNA at two hours was 47.9%, as shown in Table 6 below. Stored platelets incubated in Loading Buffer without Opti-MEM™ had a higher percentage of fluorescent siRNA-positive platelet events as compared to stored platelets incubated in Loading Buffer with Opti-MEM™ (35.4% as shown in FIG. 3 compared to 47.9% shown in Table 6.

TABLE 6

| Transfection Duration | Mean percent platelet events transfected (%) | Standard Deviation (%) |
|---|---|---|
| 2 Hours | 47.9 | 4.0 |

Figure 4:
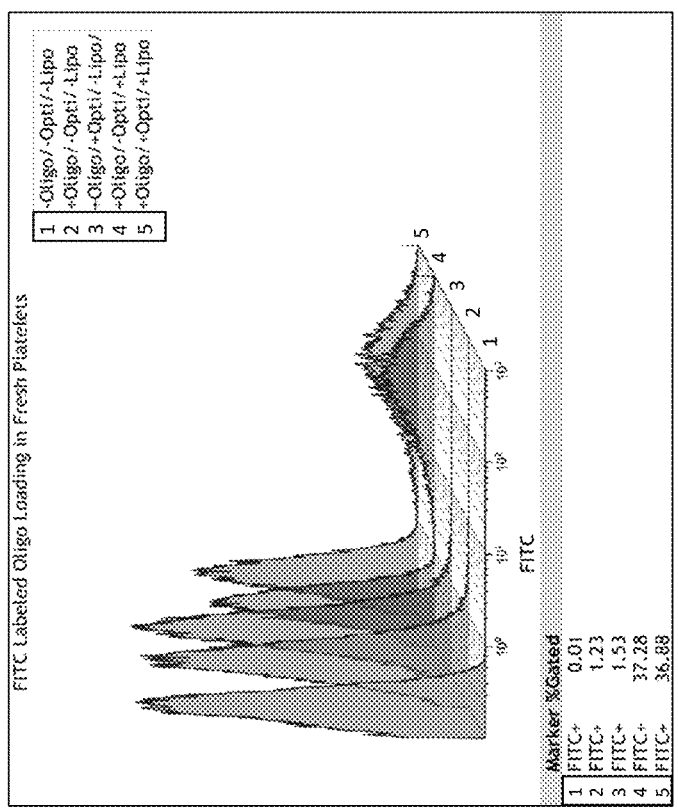
FIG. 4 shows flow cytometry data of percent transfection of stored platelets when incubated under indicated conditions. Oligo=BLOCK-iT™ Fluorescent oligo (ThermoSci). Opti=Opti-MEM™ (ThermoSci). Lipo=Lipofectamine™ RNAiMAX (ThermoSci).

Transfection efficiency of stored platelets was further analyzed in Loading Buffer by maintaining or omitting the Opti-MEM™, fluorescent siRNA, or cationic transfection reagent, as shown in FIG. 4. Stored platelets were incubated at room temperature for one hour under the conditions shown in FIG. 4. The flow cytometer was gated on stored platelets incubated without the Opti-MEM™, fluorescent siRNA, and cationic transfection reagent. Sufficient transfection (as measured by percentage of platelet events that were positive for fluorescent siRNA) was observed when the cationic transfection reagent was present, and this transfection did not appear to be the result of non-specific association of the fluorescent siRNA with the stored platelets. Oligo=BLOCK-iT™ Fluorescent siRNA. Opti=Opti-MEM™. Lipo=Lipofectamine™ RNAiMAX.

Figure 5:
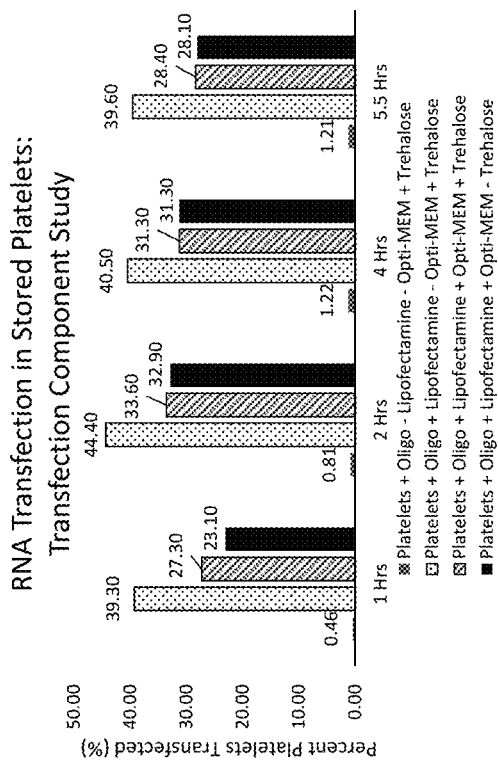
FIG. 5 shows percent transfection of stored platelets when incubated under indicated conditions. Oligo=BLOCK-iT™ Fluorescent oligo (ThermoSci). Opti=Opti-MEM™ (ThermoSci). Lipo=Lipofectamine™ RNAiMAX (ThermoSci).

In addition, transfection efficiency of stored platelets was analyzed in Loading Buffer by maintaining or omitting the Opti-MEM™, cationic transfection reagent, or Trehalose, as shown in FIG. 5. The stored platelets were incubated at room temperature for the times and under the conditions shown in FIG. 5. The percentage of platelet events that were positive for fluorescent siRNA appeared to increase when the cationic transfection reagent was maintained and the Opti-MEM™ was omitted. Trehalose did not substantially impact the transfection efficiency. Oligo=BLOCK-iT™ Fluorescent siRNA. Lipofectamine=Lipofectamine™ RNAiMAX.

Protocol 1. Loading Platelets with siRNA

The starting apheresis platelet material was pooled and characterized. The platelet pool was acidified to pH 6.6-6.8 with ACD solution. Platelets were isolated by centrifugation at ~1470 g for 20 minutes, with slow acceleration and braking. The supernatant plasma was aspirated and disposed.

The cationic transfection reagent (Lipofectamine™ RNAiMAX, 0.24% v/v Final) was diluted in HBS and the pH was adjusted to 6.6-6.8 with hydrochloric acid. The transfection period was 2 hours. The concentration of lipofectamine was 0.002% v/v. The fluorescent siRNA (BLOCK-iT™ Fluorescent siRNA, 0.377 μM Final) was diluted in HBS in a separate container as compared to the cationic transfection reagent. Both the cationic transfection reagent in FIBS and fluorescent siRNA in FIBS were incubated separately for 5 minutes at room temperature, after which time, they were combined and incubated together for an additional 10 minutes at room temperature. The platelets were resuspended in Loading Buffer and mixed with the combined cationic transfection reagent/fluorescent siRNA in FIBS mixture. The platelets were transferred to an air-permeable bag (e.g. FEP bag) and incubated at room temperature (~22° C.) with gentle agitation (e.g. 20 RPM on an orbital shaker). The resulting siRNA-loaded platelets were then analyzed further, as described herein.

Example 2

Response to Agonists by siRNA-Loaded Platelets

Figure 6:
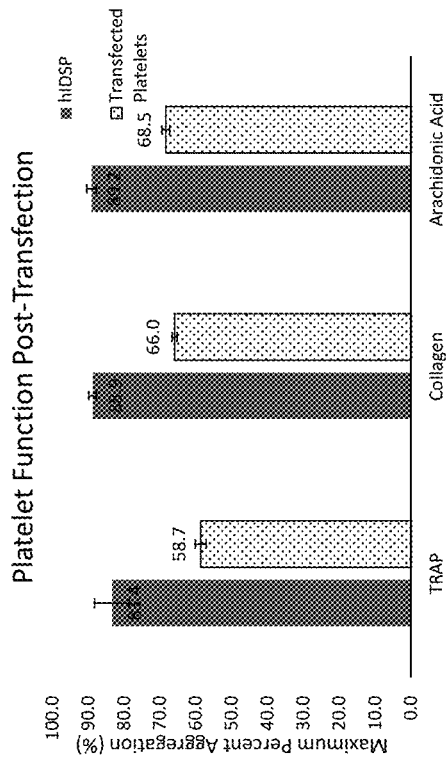
FIG. 6 shows maximum percent aggregation, when incubated for 5 hours, of siRNA-loaded stored platelets after exposure to platelet aggregation agonists Thrombin Receptor Agonist Peptide (TRAP), collagen, or arachidonic acid. hIDSP=originating stored platelets.

Multiple platelet aggregation agonists were tested for their effect on siRNA-loaded stored platelets. siRNA-loaded stored platelets were prepared as described in Protocol 1. Platelet aggregation agonists were incubated for 5 minutes at room temperature with the platelets, under gentle agitation, and washed by centrifugation (centrifugation at ~1470 g for 20 minutes, supernatant aspirated and disposed). The agonists tested were: thrombin receptor activating peptide (TRAP) at 20 μM, collagen at 10 μg/mL, and arachidonic acid at 50 μg/mL.) Light transmission aggregometry was used to evaluate each agonist's effect, as shown in FIG. 6. Although the aggregation response of siRNA-loaded stored platelets was lower as compared to non-loaded stored platelets, siRNA-loaded stored platelets still retained a strong aggregation response to all of the agonists tested.

hIDSP=originating stored platelets. Transfected platelets=siRNA-loaded platelets.

Figure 7:
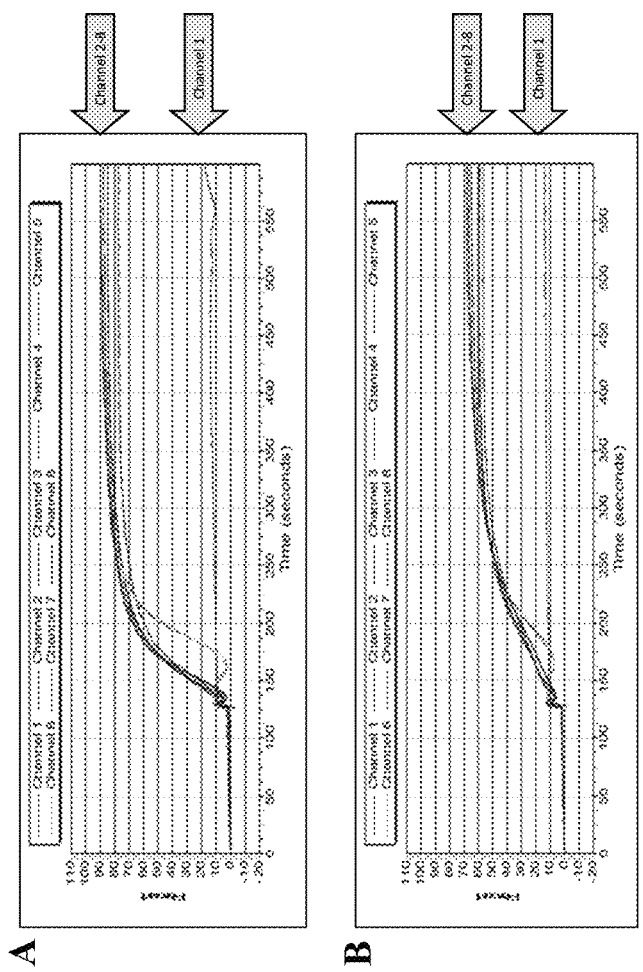
FIG. 7 provides raw aggregometry data for siRNA-loaded stored platelets incubated with platelet aggregation agonists. Channel 1=Negative Control. Channels 2-4=TRAP incubated. Channels 5-6=collagen incubated. Channels 7-8—arachidonic acid incubated.

Raw aggregometry results, as shown in FIG. 7, indicated siRNA-loaded stored platelets began to aggregate immediately after each agonist was added (~120 seconds). Channel 1=negative control where stored platelets were incubated in Loading Buffer alone. Channels 2-4=TRAP. Channels 5-6=collagen. Channels 7-8=arachidonic acid.

Example 3

Agonist Activation Increased Loading of siRNA to Fresh Platelets

Figure 8:
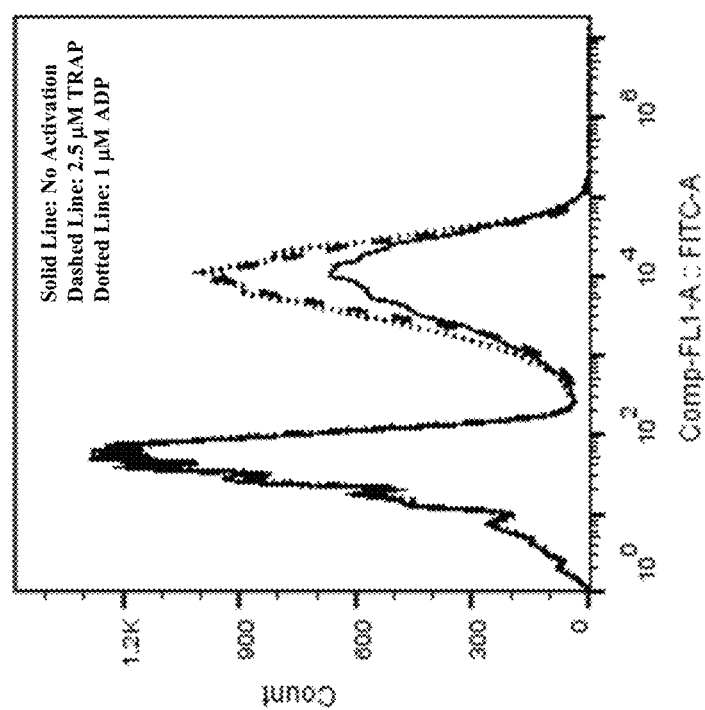
FIG. 8 shows flow cytometry data for siRNA-loaded fresh platelets after 5 minute exposure to platelet aggregation agonists adenosine diphosphate (ADP) and TRAP as compared to an unexposed control.

Platelet aggregation agonists were tested for their effect on loading of siRNA to fresh platelets, FIG. 8 and Table 7. Fresh platelets were exposed to adenosine diphosphate (ADP, 1 μM) and/or TRAP (2.5 μM) for 5 minutes followed by siRNA-loading with fluorescent siRNA (BLOCK-iT™ Fluorescent Oligo). Fresh platelets treated with platelet aggregation agonists prior to siRNA-loading demonstrated higher transfection efficiency as compared to an untreated control (52% (ADP) and 48% (TRAP) as compared to 44% (untreated)).

TABLE 7

| Agonist | Mean percent platelet events transfected (%) |
|---|---|
| None | 44 |
| ADP (1 μM) | 52 |
| TRAP (2.5 μM) | 48 |

Example 4

Figure 9:
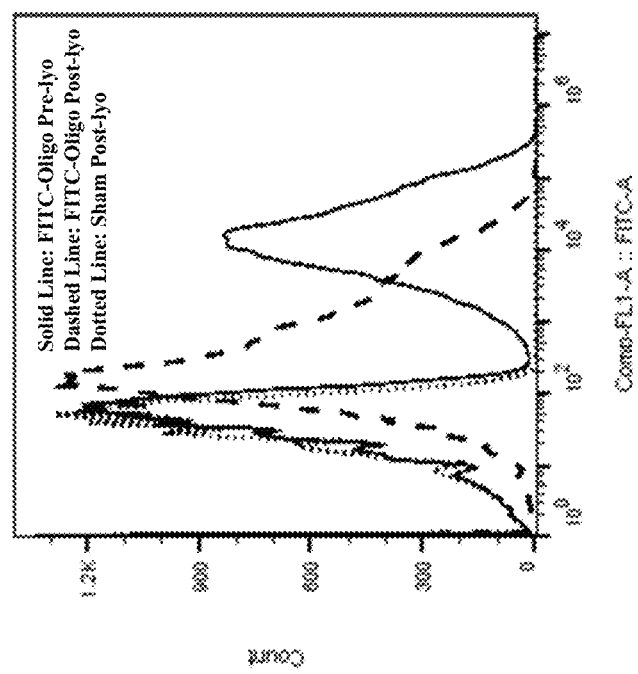
FIG. 9 shows flow cytometry data for siRNA retention in rehydrated Thrombosomes. Sham Post-Lyo=Negative Control Thrombosomes. FITC-Oligo Post-lyo=BLOCK-iT™ Fluorescent Oligo transfected post-lyophilization. FITC-Oligo Pre-lyo=BLOCK-iT™ Fluorescent Oligo transfected pre-lyophilization.

Retention of siRNA in Thrombosomes Derived from siRNA-Loaded Platelets siRNA-loaded stored platelets were prepared, following Protocol 1, and lyophilized to produce Thrombosomes. The Thrombosomes were then rehydrated and analyzed for retention of siRNA, as shown in Table 8 below and FIG. 9.

TABLE 8

| Parameter | Pre-lyophilization | Post-rehydration |
|---|---|---|
| Platelet count (*10⁶/mL) | 235 | 155 |
| Percent platelet events transfected (%) | 52 | 58 |
| gMFI of transfected platelet events | 1194 | 12394 |

A comparison of pre-lyophilization and post-rehydration siRNA-loaded stored platelets for both percentage of fluorescent siRNA positive platelet events and gMFI of platelet events indicated that a substantial amount of fluorescent siRNA was retained in the rehydrated Thrombosomes. Sham Post-lyo=negative control stored platelets post-lyophilization and rehydration. FITC-Oligo Post-lyo=BLOCK-iT™ Fluorescent siRNA transfected stored platelets post-lyophilization and rehydration. FITC-Oligo Pre-lyo=BLOCK-iT™ Fluorescent siRNA transfected stored platelets pre-lyophilization.

Example 5

Figure 10:
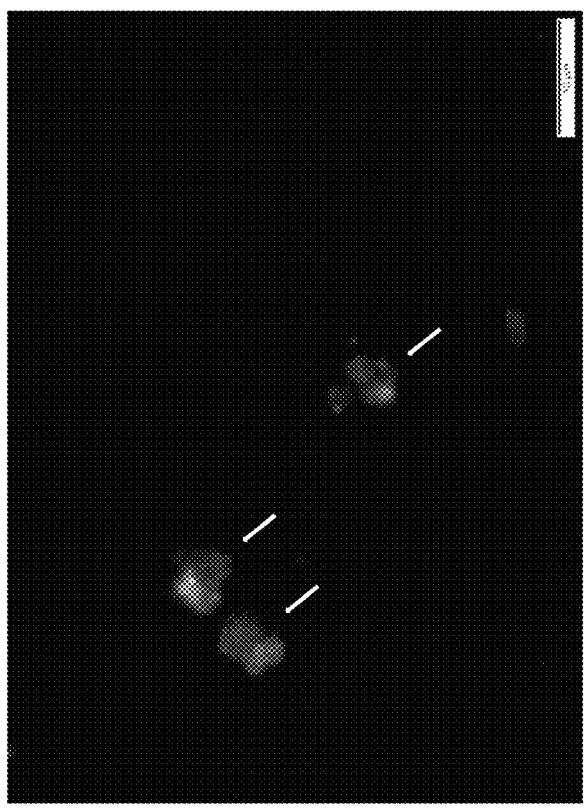
FIG. 10 shows fluorescence microscopy data for siRNA retention in rehydrated Thrombosomes transfected with fluorescent siRNA. Image is shown at 100× magnification. Scale bar is 10 μm.

Internalization of siRNA in Thrombosomes siRNA-loaded stored platelets were prepared according to Protocol 1, and lyophilized to form Thrombosomes. The Thrombosomes were analyzed after rehydration using fluorescence microscopy. FITC signal from the fluorescent siRNA was observed in the cytosol, with some punctate accumulation, as shown in FIG. 10. This signal indicated retention of the internalized fluorescent siRNA in Thrombosomes after rehydration. Arrows indicate individual fluorescent Thrombosomes.

Example 6

Figure 11:
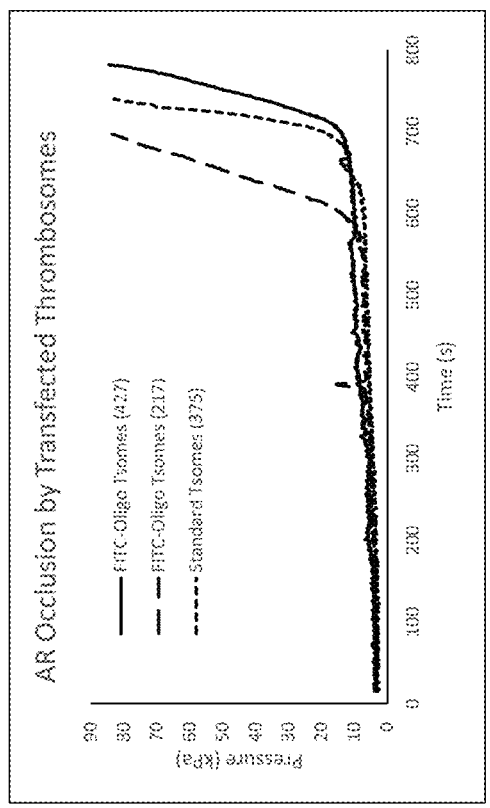
FIG. 11 provides raw occlusion time course data for Thrombosomes transfected with or without fluorescent siRNA.
Figure 12:
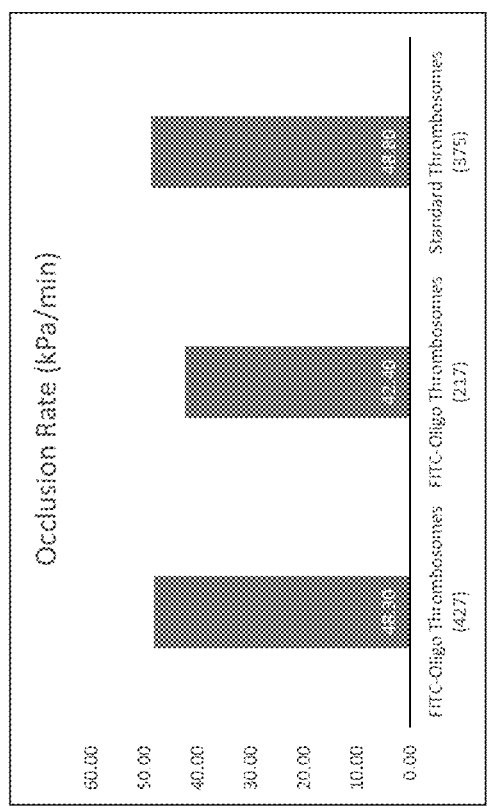
FIG. 12 shows occlusion rates for Thrombosomes transfected with or without fluorescent siRNA.

Occlusion of Collagen-Coated Microchannels by Thrombosomes Derived from siRNA-loaded Platelets siRNA-loaded platelets were prepared, following Protocol 1, and lyophilized to produce Thrombosomes. The Thrombosomes were then rehydrated and analyzed for occlusion of a collagen-coated microchannel via T-TAS®, as shown in Table 9 below and FIGS. 11 and 12. The occlusion experiment via T-TAS® was conducted following Protocol 2.

siRNA-loaded Thrombosomes were able to produce a rate of occlusion similar to that of non-loaded Thrombosomes.

TABLE 9

| Sample | Thrombosome Count in GK PPP (*10³/μL) | T10 | T80 | Rate of occlusion (kPa/min) | Area under curve |
|---|---|---|---|---|---|
| siRNA-loaded Thrombosomes (Run 1) | 427 | 11:35 | 13:02 | 48.3 | 1457.1 |
| siRNA-loaded Thrombosomes (Run 2) | 217 | 9:58 | 11:37 | 42.4 | 1566.4 |
| Non-loaded Thrombosomes | 375 | 10:54 | 12:20 | 48.8 | 1479.8 |

Protocol 2. T-TAS® Occlusion Rate Measurement

The T-TAS® was prepared for use according to the manufacturer's instructions. Briefly, the calcium corn trypsin inhibitor (CaCTI, Diapharma TR0101) and AR chip (containing collagen and tissue factor, Diapharma TC0101) were allowed to warm to room temperature prior to use. Sufficient mineral oil was pumped into the reservoir on the instrument (~2 mL as each 30-minute run requires ~400 μL mineral oil). Ethylenediaminetetraacetic acid (EDTA) was loaded into the water/EDTA line of the instrument and was primed for at least 15 seconds to flush any water or bubbles out of the EDTA lines. The dispensed liquid was cleaned from the chip stage with a kimwipe. Finally, a systems check was run to ensure pressure readings were within specification.

A vial of approximately 3×10⁸ Thrombosomes were rehydrated by a 10 minute room temperature incubation in 1.2 mL sterile water. The vial was centrifuged (~3900 g for 10 minutes) to pellet the Thrombosomes. The Thrombosomes were then resuspended in George King (GK) pooled normal human plasma to a concentration of 300,000 Thrombosomes/μL. The final Thrombosome concentration was confirmed by a hematology analyzer (AcT diff2, Beckman Coulter). Thrombosomes in GK plasma (480 μL) were then mixed with 20 μL CaCTI by gentle pipetting.

The AR chip was docked onto the T-TAS® stage and a waste reservoir was mounted onto the instrument. The sample injector was prepared by carefully adding (so as not to introduce bubbles) ~450 μL of the Thrombosome/GK plasma/CaCTI mixture. The T-TAS® instrument was run and data were recorded according to manufacturer's instructions.

Example 7

Platelet Transfection with miRNA
Methods
Transfection was conducted in a manner analogous to that used for siRNA in Protocol 1, except that the initial transfection period was 30 minutes instead of 2 hours. Two groups, Test Group A (also referred to as Subset A or as "A") and Test Group B (also referred to as Subset B or as "B") were tested. In group A, the concentration of lipofectamine was 0.002% v/v. In group B, the concentration of lipofectamine was 0.004% v/v. The starting platelet concentration was of about ~58,000/μL for both "A" and "B".
Results
After a 30 minute transfection period, no difference in platelet concentration was observed between "A" and "B" (the platelet concentration was ~58,000/μL in both cases). After a two hour transfection period, an 18% reduction in platelet count was observed for "B" and only a 3% reduction in platelet count was observed for "A." Thus, for short (30 minutes or less) transfection times the platelet count is not substantially affected by an increase in lipofectamine concentration in the transfection mixture.

| All Counts *10³/μL by AcT diff 2 | | | |
|---|---|---|---|
| | 30 Minutes | 120 Minutes | % reduction in platelet count from 30 to 120 minutes |
| Group A | 59 | 57 | 3% |
| Group B | 58 | 47 | 18% |

Figure 13:
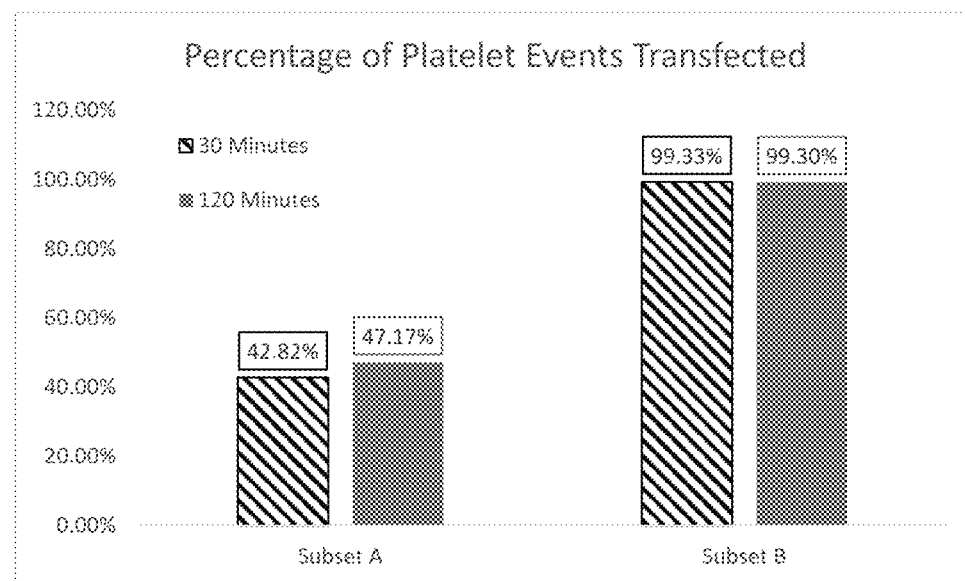
FIG. 13 shows the percentage of platelets in Test Groups A and B that are transfected under the conditions described in Example 7.

As shown in FIG. 13, in "A", only ~43% of platelets contain transfected miRNA after 30 minutes, compared to >99% of platelets in "B." These values do not change substantially in either group after 2 hours transfection (after 2 hours the percentage of transfected platelets in "A" is 47%, while in "B" it is >99%)—see FIG. 13. This suggests that most of the loading occurs within 30 minutes of exposure to the transfection components.

Figure 14:
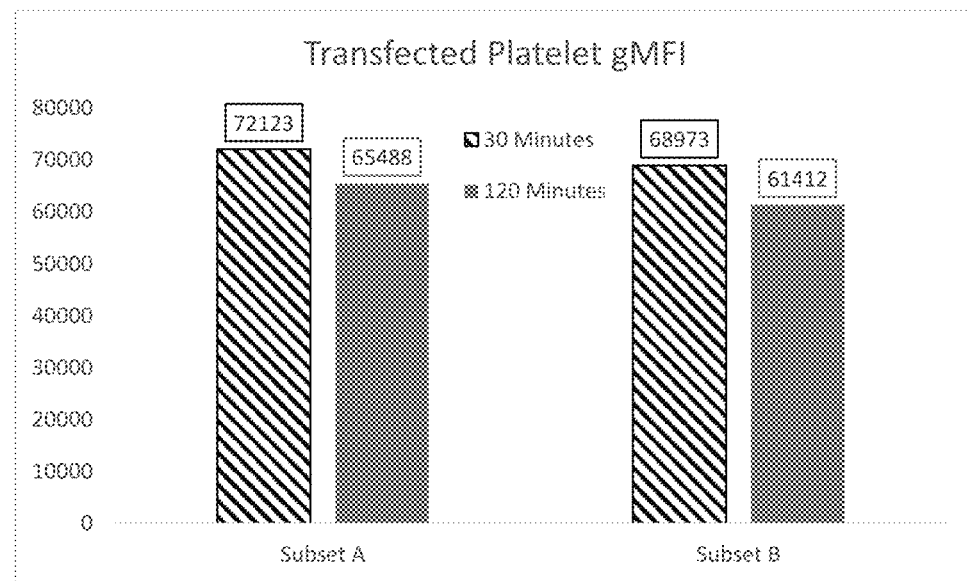
FIG. 14 shows the fluorescence intensity of platelets in Test Groups A and B that are transfected under the conditions described in Example 7.

Fluorescence intensity of the transfected platelets was nearly identical for "A" and "B" after 30 minutes (~72,000 and ~69,000 gMFI for "A" and "B," respectively, as shown in FIG. 14), suggesting that a similar amount of miRNA is loaded into each platelet for both "A" and "B." Decreases in fluorescence intensity over time (e.g., after 2 hours, as shown in FIG. 14) are likely due in part to FITC photobleaching.

Figure 15:
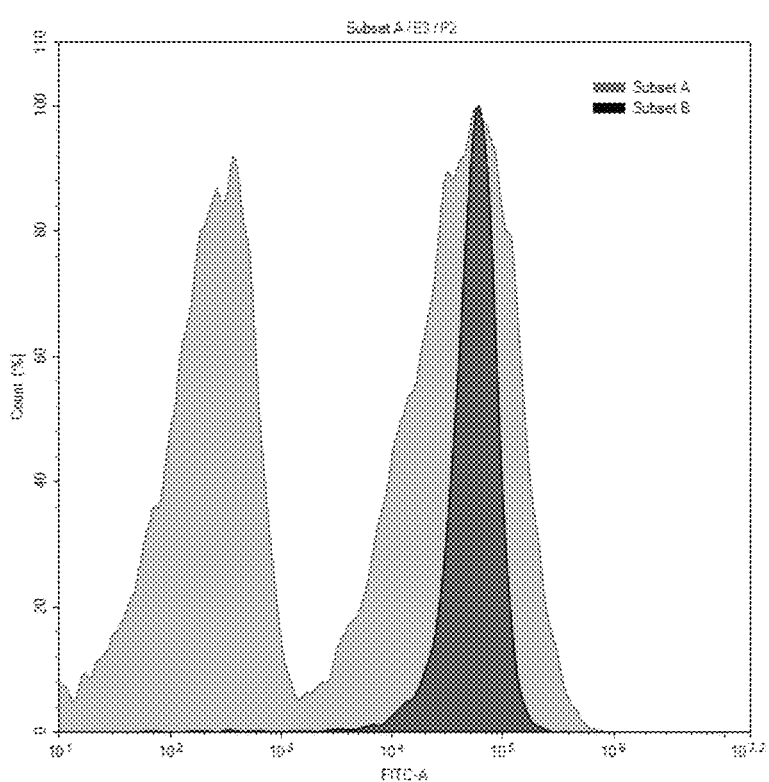
FIG. 15 shows a normalized histogram of fluorescence intensity in FITC for all single platelet events collected for Test Groups A and B that are transfected under the conditions described in Example 7.

FIG. 15 is a normalized histogram of fluorescence intensity in FITC for all single platelet events collected for "A" (gray) and "B" (black). The bimodal distribution for "A", in contrast with the unimodal distribution for "B", indicates a more consistent loading of RNA material in each platelet in "B." As used herein, "single platelet events" are particles that have been detected by the cytometer, curated to include only platelets and only singlets (that is, excluding two platelets detected simultaneously).

The above results are reproducible across a range of platelet concentrations from about 50,000 platelets/µL to about 100,000 platelets/µL. The above results are reproducible for apheresis "stored" platelets, random donor "stored" platelets (prepared from stored whole blood by fractional centrifugation), and fresh drawn platelets.

Example 8

Cryopreservation of Platelets Transfected with miR-34a miR-34a is an anti-oncogenic miRNA found in healthy tissues that downregulates >30 oncogenes and is deficient in many cancers. In this experiment miR-34a with an Alexa Fluor 647 conjugate was used in order to facilitate fluorescent detection.

Platelets were transfected at ~76,000 platelets/uL (concentration after dilution with transfection components) using 30 nM miR-34a Alexa Fluor 647 and 0.004% (v/v) Lipofectamine RNAiMAX, using the procedure described in Example 7 and a transfection time of 30 minutes.

Figure 16:
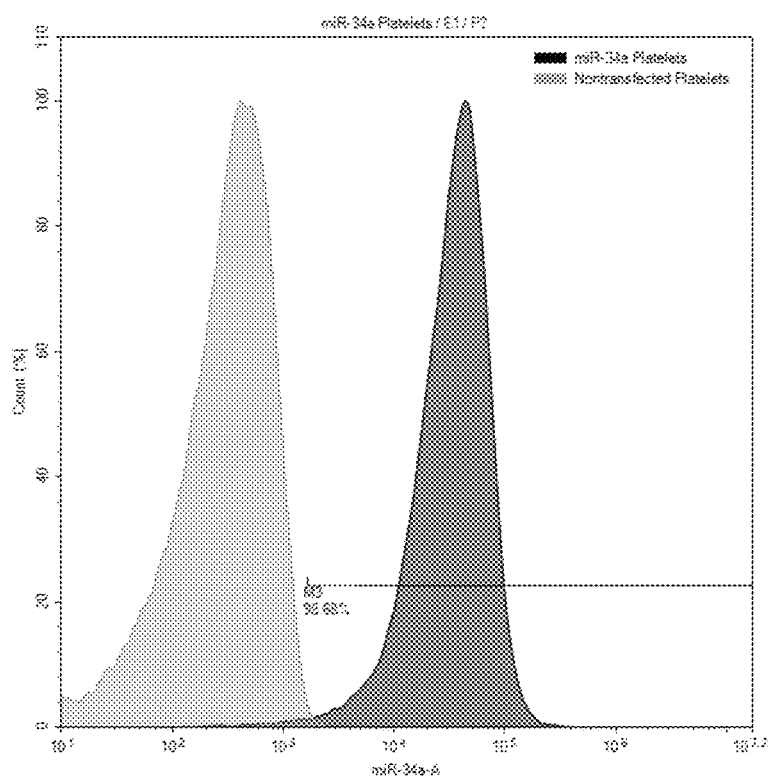
FIG. 16 shows flow cytometry plots for platelets transfected with fluorescently labeled miR-34a under the conditions described in Example 8.

After 30 minutes exposure of the platelets to the miRNA and Lipofectamine complex, platelets were washed by centrifugation (1470 g×20 minutes) and resuspended in the loading buffer of Table 2 to a concentration of approximately 1,200 platelets/uL. Transfected platelets were evaluated by flow cytometry and showed >98% platelets transfected with the fluorescently labeled miR-34a, as shown in FIG. 16.

Thrombosomes were prepared by cryopreservation of transfected platelets supplemented with 6% (w/v) polysucrose 400 and 1% (v/v) DMSO. The platelet suspension was divided into 1 mL aliquots in 1.5 mL cryogenic vials, and rapidly frozen in a −80° C. freezer. Storage was maintained at −80° C. until analysis for a minimum of 3 days.

The transfected thrombosomes (cryopreserved platelets) were then thawed for approximately 5 minutes in a 37° C. water bath prior to analysis by AcT count, flow cytometry, and T-TAS.

Figure 17:
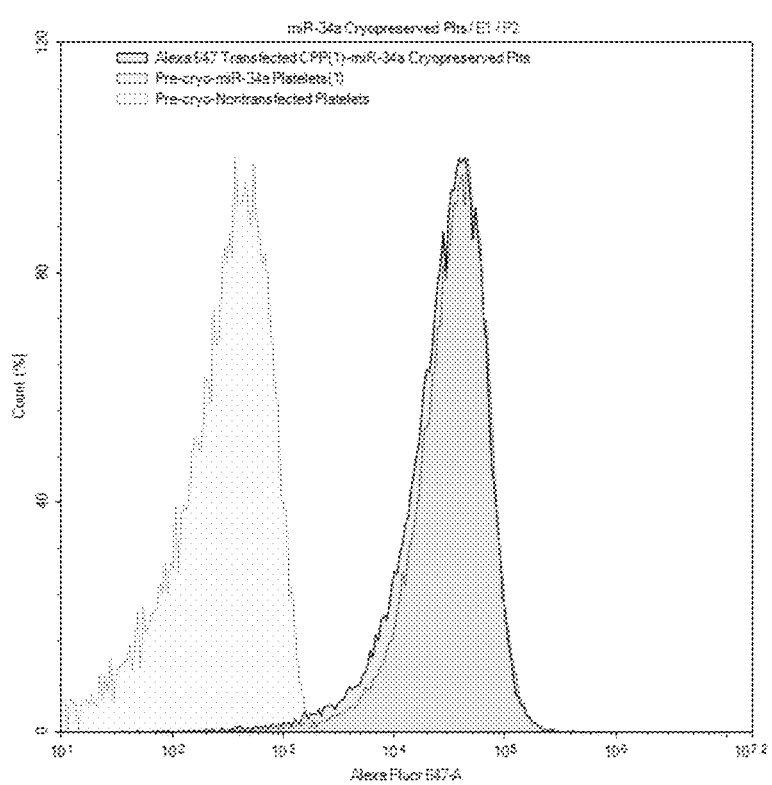
FIG. 17 shows fluorescence plots for non-transfected platelets, transfected platelets, and transfected thrombosomes (cryopreserved platelets).

The transfected thrombosomes (cryopreserved platelets) retained 90% of the fluorescence of the pre-cryopreservation platelet material as evaluated by flow cytometry, as shown in FIG. 17.

Figure 18:
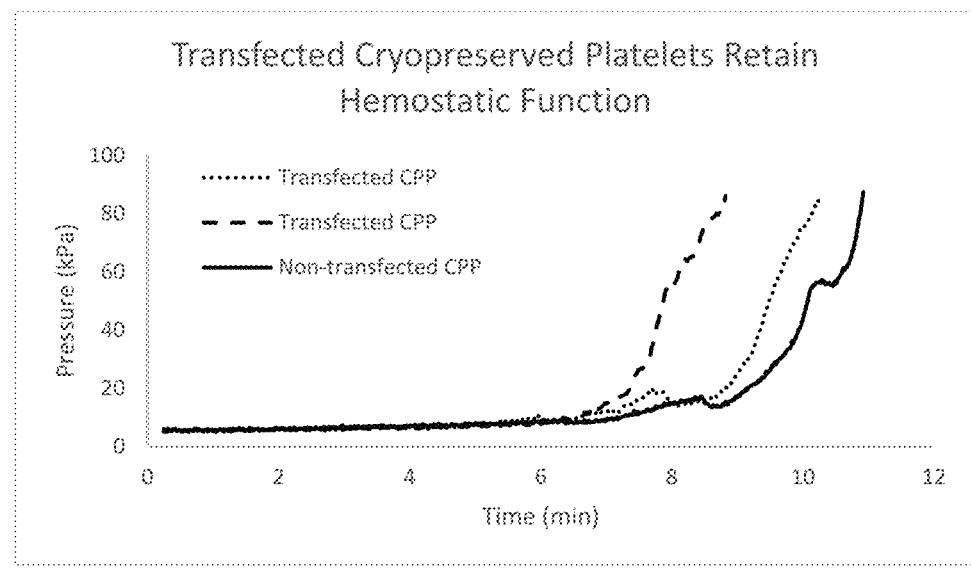
FIG. 18 shows plots of flow pressure vs. time in a channel occlusion test for non-transfected platelets and transfected thrombosomes (cryopreserved platelets).

Transfected thrombosomes (thawed, cryopreserved platelets) were prepared for T-TAS analysis by centrifugation and resuspension of the platelet pellet in citrated platelet-poor plasma to a concentration of approximately 300,000 platelets/uL. The thrombosomes (cryopreserved platelets) in plasma (480 uL) were supplemented with 20 uL CaCTI and flowed across a collagen and tissue factor coated capillary channel under high shear. Clotting and channel occlusion were assessed as a function of flow pressure over time. The results demonstrate that transfected thrombosomes—thawed, cryopreserved, transfected platelets (denoted "transfected CPP" in FIG. 18, which shows plots of flow pressure vs. time in a channel occlusion test for non-transfected platelets and transfected thrombosomes)—retain hemostatic function by rapidly occluding the collagen and tissue factor coated capillary.

EXEMPLARY EMBODIMENTS

1) A method of preparing RNA agent-loaded platelets, comprising:
treating platelets with a RNA agent
a cationic transfection reagent;
and a loading buffer comprising a salt, a base, a loading agent, and optionally at least one organic solvent,
to form the RNA agent-loaded platelets.

2) A method of preparing RNA agent-loaded platelets, comprising:
a) providing platelets; and
b) treating the platelets with a RNA agent; a cationic transfection reagent; and a loading buffer comprising a salt, a base, a loading agent, and optionally at least one organic solvent to form the RNA agent-loaded platelets.

3) The method of any one of the preceding embodiments, wherein the platelets are treated with the RNA agent and with the loading buffer sequentially, in either order.

4) The method of any one of the preceding embodiments, wherein the platelets are treated with the RNA agent and with the cationic transfection reagent sequentially, in either order.

5) A method of preparing RNA agent-loaded platelets, comprising:
(1) treating platelets with an RNA agent to form a first composition; and
(2) treating the first composition with a loading buffer comprising a salt, a base, a loading agent, and optionally at least one organic solvent, to form the RNA agent-loaded platelets.

6) The method of embodiment 5, wherein the first composition is treated with a cationic transfection reagent.

7) The method of embodiment 6, wherein the first composition treated with the cationic transfection reagent is treated with a loading buffer comprising a salt, a base, a loading agent, and optionally at least one organic solvent, to form the RNA agent-loaded platelets.

8) A method of preparing RNA agent-loaded platelets, comprising:
(1) treating the platelets with a loading buffer comprising a salt, a base, a loading agent, and optionally at least one organic solvent to form a first composition; and
(2) treating the first composition with a RNA agent, to form the RNA agent-loaded platelets.

9) The method of embodiment 8, wherein the first composition is treated with a cationic transfection reagent.

10) The method of embodiment 9, wherein the first composition treated with the cationic transfection reagent is treated with a RNA agent, to form the RNA agent-loaded platelets.

11) The method of embodiment 1 or 2, wherein the platelets are treated with the RNA agent and with the loading buffer concurrently.

12) The method of embodiment 1 or 2, wherein the platelets are treated with the RNA agent and with the cationic transfection reagent concurrently.

13) A method of preparing RNA agent-loaded platelets, comprising:
treating the platelets with a RNA agent in the presence of a cationic transfection reagent and a loading buffer comprising a salt, a base, a loading agent, and optionally at least one organic solvent to form the RNA agent-loaded platelets.

14) The method of any one of the preceding embodiments, wherein the platelets are pooled from a plurality of donors.

15) A method of preparing RNA agent-loaded platelets comprising
A) pooling platelets from a plurality of donors; and
B) treating the platelets from step (A) with a RNA agent; a cationic transfection reagent; and with a loading buffer comprising a salt, a base, a loading agent, and optionally at least one organic solvent, to form the RNA agent-loaded platelets.

16) A method of preparing RNA agent-loaded platelets comprising
A) pooling platelets from a plurality of donors; and
B)
(1) treating the platelets from step (A) with n RNA agent to form a first composition; and
(2) treating the first composition with a loading buffer comprising a salt, a base, a loading agent, and optionally at least one organic solvent, to form the RNA agent-loaded platelets.

17) The method of embodiment 16, wherein the first composition is treated with a cationic transfection reagent.

18) The method of embodiment 17, wherein the first composition treated with the cationic transfection agent is treated with a loading buffer comprising a salt, a base, a loading agent and optionally at least one organic solvent, to form the RNA agent-loaded platelets.

19) A method of preparing RNA agent-loaded platelets comprising
A) pooling platelets from a plurality of donors; and
B)
(1) treating the platelets from step (A) with a loading buffer comprising a salt, a base, a loading agent, and optionally at least one organic solvent, to form a first composition; and
(2) treating the first composition with a RNA agent to form the RNA agent-loaded platelets.

20) The method of embodiment 19, wherein the first composition is treated with a cationic transfection reagent.

21) The method of embodiment 20, wherein the first composition treated with the cationic transfection agent is treated with a loading buffer comprising a salt, a base, a loading agent, and optionally at least one organic solvent, to form the RNA agent-loaded platelets.

22) A method of preparing RNA agent-loaded platelets comprising
A) pooling platelets from a plurality of donors; and
B) treating the platelets with a RNA agent in the presence of a cationic transfection reagent and a loading buffer comprising a salt, a base, a loading agent, and optionally at least one organic solvent, to form the RNA agent-loaded platelets.

23) The method of any one of the preceding embodiments, wherein the loading buffer comprises optionally at least one organic solvent.

24) The method of any one of the preceding embodiments, wherein the loading agent is a monosaccharide or a disaccharide.

25) The method of any one of the preceding embodiments, wherein the loading agent is sucrose, maltose, dextrose, trehalose, glucose, mannose, or xylose.

26) The method of any one of the preceding embodiments, wherein the platelets are isolated prior to a treating step.

27) The method of any one of the preceding embodiments, wherein the platelets are selected from the group consisting of fresh platelets, stored platelet, and any combination thereof.

28) The method of any one of the preceding embodiments, wherein the cationic transfection reagent is a cationic lipid transfection reagent.

29) The method of any one of the preceding embodiments, wherein the RNA agent comprises siRNA.

30) The method of any one of the preceding embodiments, wherein the RNA agent comprises miRNA.

31) The method of any one of the preceding embodiments, wherein the platelets are loaded with the RNA agent in a period of time of 1 minute to 48 hours.

32) The method of any one of the preceding embodiments, wherein the concentration of RNA agent in the RNA agent-loaded platelets is from about 0.1 nM to about 10 µM.

33) The method of any one of the preceding embodiments, wherein the concentration of RNA agent in the RNA agent-loaded platelets is about 100 nM.

34) The method of any one of the preceding embodiments, wherein the one or more organic solvents selected from the group consisting of ethanol, acetic acid, acetone, acetonitrile, dimethylformamide, dimethyl sulfoxide, dioxane, methanol, n-propanol, isopropanol, tetrahydrofuran (THF), N-methyl pyrrolidone, dimethylacetamide (DMAC), or combinations thereof.

35) The method of any one of the preceding embodiments, further comprising cold storing, cryopreserving, freeze-drying, thawing, rehydrating, and combinations thereof the RNA agent-loaded platelets.

36) The method of embodiment 35, wherein the drying step comprises freeze-drying the RNA agent-loaded platelets.

37) The method of embodiment 35 or 36, further comprising rehydrating the RNA agent-loaded platelets obtained from the drying step.

38) RNA agent-loaded platelets prepared by the method of any one of the preceding embodiments.

39) Rehydrated RNA agent-loaded platelets prepared by a method comprising rehydrating the RNA agent-loaded platelets of embodiment 38.

40) The method of any one of the preceding embodiments, wherein the method does not comprise treating the platelets with an organic solvent.

41) The method of any one of embodiments 5 to 10 or 16 to 21, wherein the method does not comprise treating the first composition with an organic solvent.

42) The method of any one of the preceding embodiments, wherein the method comprises treating the platelets with Prostaglandin E1 (PGE1) or Prostacyclin.

43) The method of any one of embodiments 1 to 41, wherein the method does not comprise treating the platelets with Prostaglandin E1 (PGE1) or Prostacyclin.

44) The method of any one of embodiments 1 to 42, wherein the method comprises treating the first composition with Prostaglandin E1 (PGE1) or Prostacyclin.

45) The method of any one of embodiments 1 to 41 or 43, wherein the method does not comprise treating the first composition with Prostaglandin E1 (PGE1) or Prostacyclin.

The invention claimed is:
1. A method of preparing RNA agent-loaded cryopreserved platelets, comprising:
providing platelets;
treating the platelets with a RNA agent that is a siRNA and/or a miRNA in the presence of a cationic transfection reagent, and a loading buffer comprising a salt, a base, and a loading agent comprising one or more saccharides selected from the group consisting of trehalose, sucrose, maltose, mannose, dextrose, and xylose, for a time period in the range of 5 minutes to 4 hours, and at a temperature in the range of 18-42° C., to form RNA agent-loaded platelets; and
cryopreserving the RNA agent-loaded platelets in the presence of the loading buffer, dimethyl sulfoxide (DMSO), and polysucrose to form the RNA agent-loaded cryopreserved platelets, wherein the RNA agent-loaded cryopreserved platelets after storage at a temperature of about −80° C., upon thawing:
retain at least 90% of the RNA agent, and
retain hemostatic function by displaying the property of occluding a capillary coated with collagen and tissue factor in an in vitro total thrombus-formation analysis system (T-TAS).

2. The method of claim 1, wherein the platelets are pooled from a plurality of donors.

3. The method of claim 1, wherein the loading buffer further comprises at least one organic solvent selected from the group consisting of ethanol, acetic acid, acetone, acetonitrile, dimethylformamide, dioxane, methanol, n-propanol, isopropanol, tetrahydrofuran (THF), N-methyl pyrrolidone, dimethylacetamide (DMAC), or combinations thereof.

4. The method of claim 1, wherein the loading agent comprises dextrose, and trehalose, and DMSO is present in an amount in the range of 0.1% to 5.0% v/v.

5. The method of claim 4, wherein the platelets are selected from the group consisting of fresh platelets, stored platelet, and any combination thereof.

6. The method of claim 4, wherein the cationic transfection reagent is a cationic lipid transfection reagent.

7. The method of claim 6, wherein the RNA agent comprises siRNA.

8. The method of claim 6, wherein the RNA agent comprises miRNA.

9. The method of claim 1, wherein the time period is in the range of 20 minutes to 3 hours, wherein the concentration of RNA agent in the RNA agent-loaded platelets is from about 0.1 nM to about 10 μM, and wherein the RNA agent-loaded cryopreserved platelets after storage, upon thawing retain at least 90% of channel occlusion in an in vitro total thrombus-formation analysis system (T-TAS).

10. The method of claim 9, wherein the concentration of RNA agent in the RNA agent-loaded platelets is from about 10 nM to about 10 μM.

11. The method of claim 7, wherein polysucrose is an amount in the range of 3% to 10% w/v, trehalose is in an amount in the range of 10 mM to 500 mM, DMSO is in an amount in the range of 0.3% to 3.0% v/v, and wherein the organic solvent comprises ethanol in an amount in the range of 0.1% to 5.0% v/v.

12. The method of claim 11, wherein polysucrose is in an amount in the range of 3% to 7% w/v, and trehalose is in an amount in the range of 20 mM to 200 mM, and wherein DMSO is in an amount in the range of 0.5% to 2.0% v/v.

13. The method of claim 11, wherein the RNA agent-loaded cryopreserved platelets are stored for at least 6 months.

14. The method of claim 8, wherein polysucrose is in an amount in the range of 3% to 10% w/v, and trehalose is in an amount in the range of 10 mM to 500 mM, DMSO is in an amount in the range of 0.3% to 3.0% v/v, and wherein the at least one organic solvent comprises ethanol in an amount in the range of 0.1% to 5.0% v/v.

15. The method of claim 14, wherein polysucrose is in an amount in the range of 3% to 7% w/v, and trehalose is in an amount in the range of 20 mM to 200 mM, and wherein DMSO is in an amount in the range of 0.5% to 2.0% v/v.

16. The method of claim 14, wherein the RNA agent-loaded cryopreserved platelets are stored for at least 3 days, and wherein the RNA agent-loaded cryopreserved platelets after storage, upon thawing retain at least 90% of channel occlusion in an in vitro total thrombus-formation analysis system (T-TAS).

17. The method of claim 16, wherein the RNA agent-loaded cryopreserved platelets are stored for at least 6 months.

18. The method of claim 16, wherein the RNA agent-loaded cryopreserved platelets are stored for a time period of 3 days to 6 months.

19. The method of claim 14, wherein the time period is in the range of 20 minutes to 3 hours, and the temperature in the range of 20° C. to 40° C.

20. The method of claim 11, wherein the time period is in the range of 20 minutes to 3 hours, and the temperature in the range of 20° C. to 40° C., wherein the RNA agent-loaded cryopreserved platelets are stored for a time period of 3 days to 6 months, and wherein the RNA agent-loaded cryopreserved platelets after storage, upon thawing retain at least 90% of channel occlusion in an in vitro total thrombus-formation analysis system (T-TAS).

* * * * *